(12) United States Patent
Yamanaka et al.

(10) Patent No.: US 8,927,277 B2
(45) Date of Patent: *Jan. 6, 2015

(54) METHOD OF EFFICIENTLY ESTABLISHING INDUCED PLURIPOTENT STEM CELLS

(75) Inventors: Shinya Yamanaka, Kyoto (JP); Naoki Goshima, Tokyo (JP); Momoko Maekawa, Kyoto (JP); Yoshifumi Kawamura, Tokyo (JP); Hiromi Mochizuki, Tokyo (JP)

(73) Assignees: Kyoto University, Kyoto (JP); National Institute of Advanced Industrial Science and Technology, Tokyo (JP); Japan Biological Informatics Consortium, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/579,234

(22) PCT Filed: Feb. 16, 2011

(86) PCT No.: PCT/JP2011/053874
§ 371 (c)(1),
(2), (4) Date: Oct. 4, 2012

(87) PCT Pub. No.: WO2011/102531
PCT Pub. Date: Aug. 25, 2011

(65) Prior Publication Data
US 2013/0029423 A1    Jan. 31, 2013

Related U.S. Application Data

(60) Provisional application No. 61/305,107, filed on Feb. 16, 2010, provisional application No. 61/379,949, filed on Sep. 3, 2010.

(51) Int. Cl.
*C12N 5/00* (2006.01)
*C12N 5/02* (2006.01)
*C12N 5/074* (2010.01)

(52) U.S. Cl.
CPC .......... *C12N 5/0696* (2013.01); *C12N 2501/60* (2013.01); *C12N 2501/602* (2013.01); *C12N 2501/603* (2013.01); *C12N 2501/604* (2013.01); *C12N 2510/00* (2013.01)
USPC .......................................... 435/377; 435/6.1

(58) Field of Classification Search
USPC ........................................................ 800/377
See application file for complete search history.

(56) References Cited

U.S. PATENT DOCUMENTS

| | | |
|---|---|---|
| 2009/0068742 A1 | 3/2009 | Yamanaka |
| 2011/0231944 A1 | 9/2011 | Watarai et al. |
| 2011/0236362 A1 | 9/2011 | Watarai et al. |

FOREIGN PATENT DOCUMENTS

| | | |
|---|---|---|
| CN | 101613717 A | 12/2009 |
| EP | 1 970 446 A1 | 9/2008 |
| EP | 2 096 169 A1 | 9/2009 |
| WO | WO 2007/069666 A1 | 6/2007 |
| WO | WO 2008/118820 A2 | 10/2008 |
| WO | WO 2009/057831 A1 | 5/2009 |
| WO | WO 2010/027062 A1 | 3/2010 |
| WO | WO 2010/027094 A1 | 3/2010 |
| WO | WO 2010/098419 A1 | 9/2010 |
| WO | WO 2011/016588 A1 | 2/2011 |

OTHER PUBLICATIONS

Djuric and Ellis, 202, Stem Cell Research and Therapy, 2010,1:3, pp. 1-6.*
NIH Stem Cells: Scientific Progress and Future Research Directions, Department of Health and Human Services, Chapter 1, pp. 1-4, Jun. 2001.*
Thomson et al. PNAS, 92:7844-7848 (Aug. 1995).*
Heng et al 2005a, Cell Tissue Res, 321:147-150.*
Heng 2005b, Biomedicine and Pharmacotherapy, 59:132-134.*
Bosnali, 2008, Biol Chem, 389:851-861.*
Aoi et al., *Science*, 321(5889): 699-702 (2008).
Aruga, *Mol. Cell. Neurosci.*, 26(2): 205-221 (2004).
Blelloch et al., *Cell Stem Cell*, 1: 245-247 (2007).
Brambrink et al., *Cell Stem Cell*, 2(2): 151-159 (2008).
Feng et al., *Nature Cell Biology*, 11(2): 197-203 (2009).
Guo et al., *Development*, 136: 1063-1069 (2009).
Hanna et al., *Cell*, 133(2): 250-264 (2008).
Heng et al., *Cell Stem Cell*, 6(2): 167-174 (2010).
Huangfu et al., *Nature Biotechnology*, 26(11): 1269-1275 (2008).
Jiang et al., *Nature Cell Biology*, 10: 353-360 (2008).
Kim et al., *Journal of Biological Chemistry*, 277(34): 30901-30913 (2002).
Kim et al., *Nature*, 454: 646-650 (2008).
Kim et al., *Cell*, 136: 411-419 (2009).
Liao et al., *Cell Research*: 18: 600-603 (2008).
Lyssiotis et al., *Proc. Natl. Acad. Sci. USA*, 106(22): 8912-8917 (2009).
Maekawa et al., *Nature*, 474(7350): 225-229 and supplementary information pp. 1-19 (2011).
Maherali et al., *Cell Stem Cell*, 1: 55-70 (2007).
Mali et al., *Stem Cells*, 26: 1998-2005 (2008).

(Continued)

*Primary Examiner* — Valarie Bertoglio
(74) *Attorney, Agent, or Firm* — Leydig, Voit & Mayer, Ltd.

(57) ABSTRACT

Provided are a method of improving the efficiency of establishment of iPS cells, comprising the step of contacting one or more substances selected from the group consisting of members of the GLIS family (e.g., GLIS1) and nucleic acids that encode the same and one or more substances selected from the group consisting of members of the Klf family and nucleic acids that encode the same, with a somatic cell, an iPS cell comprising an exogenous nucleic acid that encodes a member of the GLIS family or a member of the Klf family, that can be obtained by the method, and a method of producing a somatic cell by inducing the differentiation of the iPS cell.

6 Claims, 21 Drawing Sheets

(56) References Cited

OTHER PUBLICATIONS

Mandayam et al., *Histol. Histopathol.*, 24(10): 1343-1355 (2009).
Markoulaki et al., *Nature Biotechnology*, 27(2): 169-171 (2009).
Meissner et al., *Nature Biotechnology*, 25: 1177-1181 (2007).
McConnell, et al., *Bioassays*, 29: 549-557 (2007).
Nakagawa et al., *Nature Biotechnology*, 26(1): 101-106 (2008).
Nakagawa et al., *Proc. Natl. Acad. Sci. USA*, 107(32): 14152-14157 (2010).
Nakatake et al., *Molecular Cellular Biology*, 26(20): 7772-7782 (2006).
Nandan et al., *Histol Histopathol.*, 24(10): 1343-1355 (2009).
Okita et al., *Nature*, 448: 313-317 (2007).
Ottolenghi et al., *Genomics*, 79(3): 333-343 (2002).
Park et al., *Nature*, 451: 141-146 (2008).
Semina et al., *Nature Genetics*, 14(4): 392-399 (1996).
Shi et al., *Cell Stem Cell*, 2: 525-528 (2008).
Takahashi et al., *Cell*, 126: 663-676 (2006).
Takahashi et al., *Cell*, 131: 861-872 (2007).
Takeuchi et al., *Gene Expression Patterns*, 7(1-2): 51-56 (2006).
Wernig et al., *Nature*, 448: 318-324 (2007).
Wernig et al., *Cell Stem Cell*, 2: 10-12 (2008).
Yu et al., *Science*, 318: 1917-1920 (2007).
Zardo et al., *Leukemia*, 22(8): 1503-1518 (2008).
Zhao et al., *Cell Stem Cell*, 3: 475-479 (2008).
Database DDBJ/EMBL/GenBank [online], Accession No. NM_024335, "*Homo sapiens* Iroquois homeobox protein 6 (IRX6), mRNA" (Feb. 19, 2004).
Sabiosciences: "Induced Pluripotent Stem Cells—Quick Facts", Technical Notes (Jan. 1, 2009) [retrieved on Apr. 17, 2013, from the Internet at http://sabiosciences.com/manuals/iPSCstemCELLS.pdf].
European Patent Office, Supplementary European Search Report in European Patent Application No. EP 10 74 6298 (Jul. 31, 2012).
European Patent Office, European Search Report in European Patent Application No. 13 15 8495 (May 17, 2013).
Japanese Patent Office, International Search Report in International Patent Application No. PCT/JP2010/053034 (May 25, 2010), English translation.
Japanese Patent Office, International Search Report in International Patent Application No. PCT/JP2010/053874 (May 31, 2011), English translation.
Djuric et al., *Stem Cell Research & Therapy*, 1: 3 [doi:10.1186/scrt3] (2010).
Chinese Patent Office, First Office Action in Chinese Patent Application No. 201180009618.9 (Jul. 18, 2013) English translation.
Maekawa et al., *Nature*, 474: 225-229 and accompanying methods (1 page) and supplementary information (19 pages) (Jun. 9, 2011).
Mitrovic, *Medicine and Biology*, 10(3): 101-105 (2003).
Morrison et al., *Developmental Dynamics*, 236: 481-488 (2007).
Yee, *Nature Education*, 3(9): 25 (2010) (as retrieved from http://www.nature.com/scitable/topicpage/turning-somatic-cells-into-pluripotent-stem-cells-14431451 on Mar. 27, 2014).
Kim et al., *The Journal of Biological Chemistry*, 277(34): 30901-30913 (2002).
European Patent Office, Extended European Search Report in European Patent Application No. 11744817.5 (Dec. 13, 2013).

\* cited by examiner

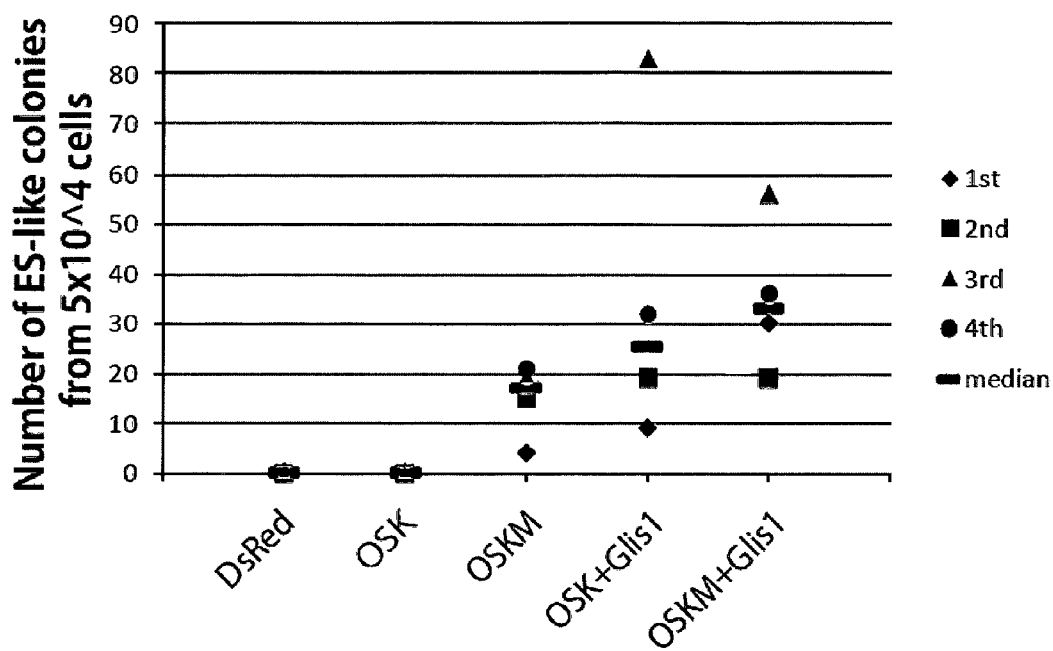
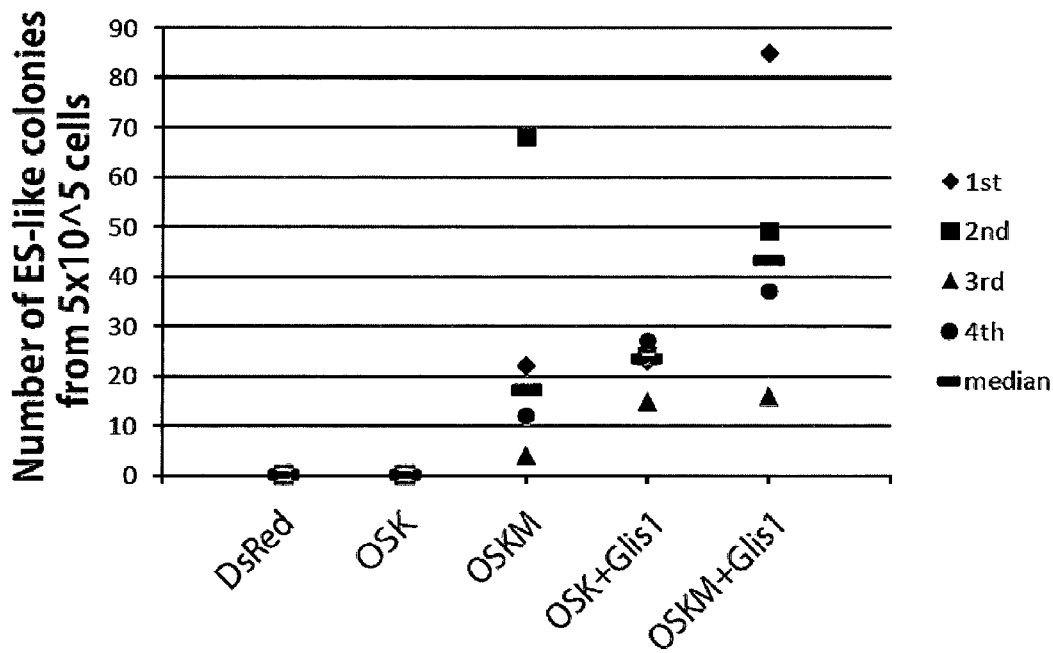
Fig. 19

Fig. 20
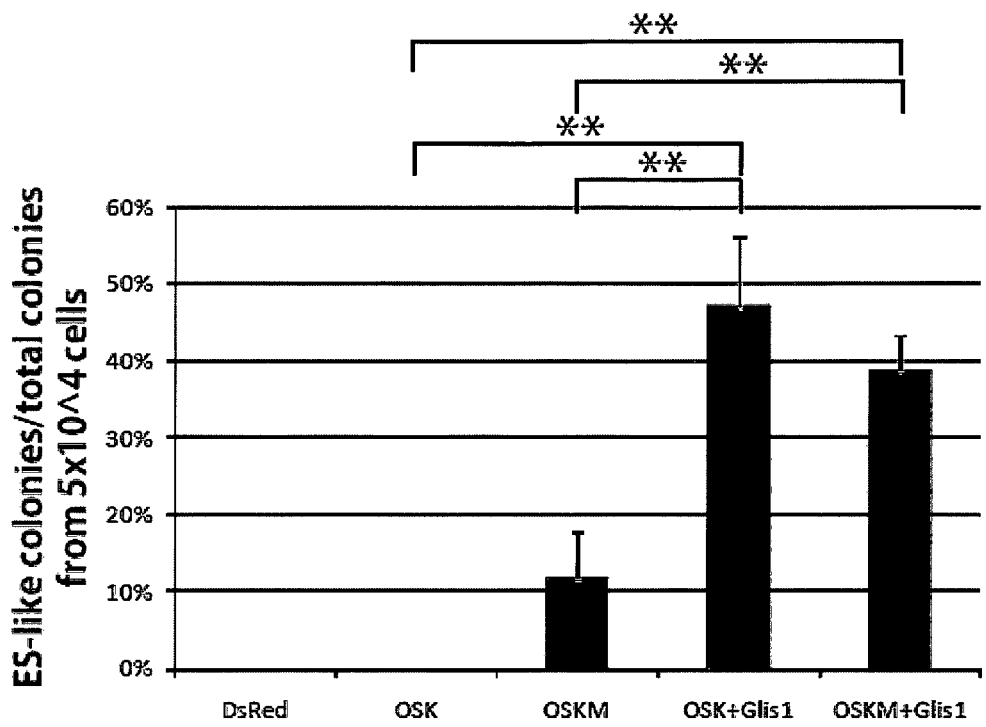
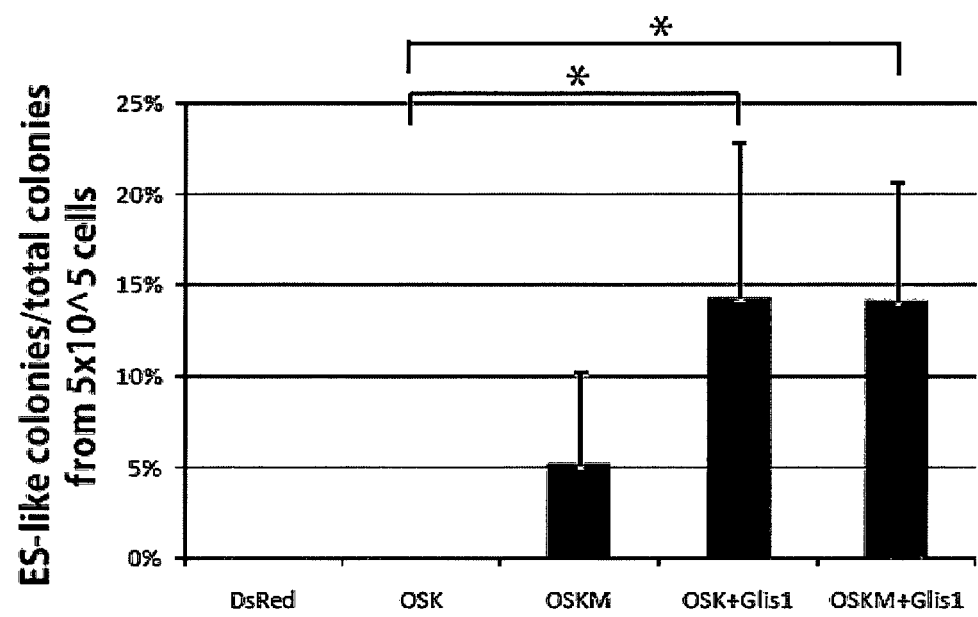

METHOD OF EFFICIENTLY ESTABLISHING INDUCED PLURIPOTENT STEM CELLS

CROSS-REFERENCE TO RELATED APPLICATIONS

This patent application is a U.S. National Phase of PCT/JP2011/053874, filed on Feb. 16, 2011, which claims the benefit of U.S. Provisional Patent Application No. 61/305,107, filed on Feb. 16, 2010, and U.S. Provisional Patent Application No. 61/379,949, filed on Sep. 3, 2010, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 63,516 bytes ASCII (Text) file named "710888SequenceListing.txt," created Aug. 14, 2012.

TECHNICAL FIELD

The present invention relates to a method of improving the efficiency of establishment of induced pluripotent stem cells (hereinafter referred to as iPS cells) and reagents therefor, more specifically to a method of improving the efficiency of establishment of iPS cells using members of the GLIS family and members of the Klf family, and reagents therefor and the like.

BACKGROUND OF THE INVENTION

In recent years, mouse and human iPS cells have been established one after another. Takahashi and Yamanaka induced iPS cells by transferring the Oct3/4, Sox2, Klf4 and c-Myc genes into fibroblasts from a reporter mouse wherein the neomycin resistance gene is knocked-in into the Fbx15 locus, and forcing the cells to express the genes [Takahashi, K. and Yamanaka, S., Cell, 126: 663-676 (2006)]. Okita et al. succeeded in establishing iPS cells (Nanog iPS cells) that show almost the same gene expression and epigenetic modification profiles as those of embryonic stem (ES) cells, by creating a transgenic mouse having the green fluorescent protein (GFP) and puromycin resistance genes integrated into the locus of Nanog, whose expression is more localized in pluripotent cells than the expression of Fbx15, forcing fibroblasts from the mouse to express the above-mentioned four genes, and selecting cells that are puromycin-resistant and GFP-positive cells [Okita, K. et al., Nature, 448: 313-317 (2007)]. Similar results were obtained by other groups [Wernig, M. et al., Nature, 448: 318-324 (2007); Maherali, N. et al., Cell Stem Cell, 1: 55-70 (2007)]. Thereafter, it was revealed that iPS cells could also be produced with 3 factors other than the c-Myc gene [Nakagawa, M. et al., Nat. Biotechnol., 26: 101-106 (2008)].

Furthermore, Takahashi et al. [Takahashi, K. et al., Cell, 131: 861-872 (2007)] succeeded in establishing iPS cells by introducing the same 4 genes as those used in the mouse into human skin fibroblasts. On the other hand, Yu et al. produced human iPS cells using Nanog and Lin28 in place of Klf4 and c-Myc [Yu, J. et al., Science, 318: 1917-1920 (2007)]. Hence, it has been demonstrated that iPS cells comparable to ES cells in terms of pluripotency can be produced in both humans and mice, by transferring defined factors into somatic cells.

Since then, a wide variety of attempts have been made to increase the efficiency of iPS cell establishment, including iPS cells established by transferring TERT and SV40 large T antigen (known as a human cell immortalization genes), along with the four factors Oct3/4, Sox2, Klf4 and c-Myc [Park, I. H. et al., Nature, 451: 141-146 (2008)], iPS cells established with the addition of Nanog and Lin28 to the foregoing four factors [Liao, J. et al., Cell Research, 18: 600-603 (2008)], and iPS cells established with the addition of UTF1 to the foregoing four or three factors other than c-Myc [Zhao, Y. al., Cell Stem Cell, 3: 475-479 (2008)]. However, the situation stands wherein no satisfactory improvement has been achieved.

SUMMARY OF THE INVENTION

The present inventors conducted a comprehensive investigation in search of genes that can be used to establish iPS cells, as substitutes for Klf4, not only out of genes expressed specifically in pluripotent cells such as ES cells, but also from a broader range of gene libraries of transcription factors. The inventors thus succeeded in efficiently establishing iPS cells by transferring a gene belonging to the GLIS family (e.g., GLIS1), a gene belonging to the PTX family (e.g., PITX2), or the DMRT-like family B with proline-rich C-terminal 1 gene (DMRTB1), along with the three genes Oct3/4, Sox2 and c-Myc, to mouse and human dermal fibroblasts, and identified these transcription factors as novel nuclear reprogramming substances capable of functionally substituting for Klf4 (U.S. Provisional Application No. 61/208,853, filed on Feb. 27, 2009 and U.S. Provisional Application No. 61/276,123, filed on Sep. 8, 2009).

Next, the present inventors investigated the effects of these Klf4 substitute factors GLIS1, PITX2 and DMRTB1 used in combination with Klf4 on the establishment of iPS cells. As an unexpected result, PITX2 and DMRTB1 exhibited absolutely no additional effect when combined with Klf4, whereas combined use of GLIS1 and Klf4 produced a dramatic synergistic effect on the establishment of iPS cells in both mouse and human cells. The present inventors conducted further investigations based on these findings, and have developed the present invention.

Accordingly, the present invention provides the following:
[1] A method of improving iPS cell establishment efficiency, comprising contacting the following (1) and (2):
(1) one or more substances selected from the group consisting of members of the GLIS family and nucleic acids that encode the same,
(2) one or more substances selected from the group consisting of members of the Klf family and nucleic acids that encode the same,
with a somatic cell.
[2] The method according to [1] above, wherein the substances (1) above include GLIS family zinc finger 1 (GLIS1) or a nucleic acid that encodes the GLIS1.
[3] The method according to [1] or [2] above, wherein the substances (2) above include Klf4 or a nucleic acid that encodes the Klf4.
[4] An iPS cell establishment efficiency improver comprising the following (1) and (2):
(1) one or more substances selected from the group consisting of members of the GLIS family and nucleic acids that encode the same,
(2) one or more substances selected from the group consisting of members of the Klf family and nucleic acids that encode the same.

[5] The improver according to [4] above, wherein the substances (1) above include GLIS1 or a nucleic acid that encodes the GLIS1.

[6] The improver according to [4] or [5] above, wherein the substances (2) above include Klf4 or a nucleic acid that encodes the Klf4.

[7] A method of producing an iPS cell, comprising contacting the following (1), (2) and (3):
(1) one or more substances selected from the group consisting of members of the GLIS family and nucleic acids that encode the same,
(2) one or more substances selected from the group consisting of members of the Klf family and nucleic acids that encode the same,
(3) a nuclear reprogramming substance capable of inducing an IFS cell from a somatic cell by being combined with the substances (1) and (2) above,
with a somatic cell.

[8] The method according to [7] above, wherein the substances (1) above include GLIS1 or a nucleic acid that encodes the GLIS1.

[9] The method according to [7] or [8] above, wherein the substances (2) above include Klf4 or a nucleic acid that encodes the Klf4.

[10] The method according to any one of [7] to [9] above, wherein the nuclear reprogramming substance (3) above is selected from the group consisting of members of the Oct family, members of the Sox family, members of the Myc family, members of the Lin28 family, Nanog, and nucleic acids that encode the same.

[11] The method according to any one of [7] to [9] above, wherein the nuclear reprogramming substance (3) above includes Oct3/4 or a nucleic acid that encodes the same.

[12] The method according to [11] above, wherein the nuclear reprogramming substance (3) above includes Oct3/4 and Sox2 or nucleic acids that encode the same.

[13] The method according to [11] above, wherein the nuclear reprogramming substance (3) above includes Oct3/4, Sox2 and c-Myc or nucleic acids that encode the same.

[14] An agent for iPS cell induction from a somatic cell, comprising the following (1), (2) and (3):
(1) one or more substances selected from the group consisting of members of the GLIS family and nucleic acids that encode the same,
(2) one or more substances selected from the group consisting of members of the Klf family and nucleic acids that encode the same,
(3) a nuclear reprogramming substance capable of inducing an iPS cell from a somatic cell by being combined with the substances (1) and (2) above.

[15] The agent according to [14] above, wherein the substances (1) above include GLIS1 or a nucleic acid that encodes the GLIS1.

[16] The agent according to [14] or [15] above, wherein the substances (2) above include Klf4 or a nucleic acid that encodes the Klf4.

[17] The agent according to any one of [14] to [16] above, wherein the nuclear reprogramming substance (3) above is selected from the group consisting of members of the Oct family, members of the Sox family, members of the Myc family, members of the Lin28 family, Nanog, and nucleic acids that encode the same.

[18] The agent according to any one of [14] to [16] above, wherein the nuclear reprogramming substance (3) above includes Oct3/4 or a nucleic acid that encodes the same.

[19] The agent according to [18] above, wherein the nuclear reprogramming substance (3) above includes Oct3/4 and Sox2 or nucleic acids that encode the same.

[20] The agent according to [18] above, wherein the nuclear reprogramming substance (3) above includes Oct3/4, Sox2 and c-Myc or nucleic acids that encode the same.

[21] An iPS cell comprising the following (1) and (2):
(1) one or more nucleic acids selected from the group consisting of exogenous nucleic acids that encode members of the GLIS family,
(2) one or more nucleic acids selected from the group consisting of exogenous nucleic acids that encode members of the Klf family.

[22] The iPS cell according to [21] above, wherein the exogenous nucleic acids are integrated in a genome.

[23] A method of producing a somatic cell, comprising treating the iPS cell according to [21] or [22] above to induce it to differentiate into a somatic cell.

[24] A method of producing a somatic cell, comprising the following (1) and (2):
(1) the step of producing an iPS cell by the method according to any one of [7] to [13] above, and
(2) the step of treating the iPS cell obtained through the step (1) above to induce it to differentiate into a somatic cell.

[25] A use of the following (1) and (2) to improve the efficiency of establishment of iPS cells:
(1) one or more substances selected from the group consisting of members of the GLIS family and nucleic acids that encode the same,
(2) one or more substances selected from the group consisting of members of the Klf family and nucleic acids that encode the same.

[26] A use of one or more substances selected from the group consisting of members of the GLIS family and nucleic acids that encode the same to improve the efficiency of establishment of iPS cells, wherein the substances, along with one or more substances selected from the group consisting of members of the Klf family and nucleic acids that encode the same, are contacted with a somatic cell.

[27] A use of the following (1), (2) and (3) to produce an iPS cell:
(1) one or more substances selected from the group consisting of members of the GLIS family and nucleic acids that encode the same,
(2) one or more substances selected from the group consisting of members of the Klf family and nucleic acids that encode the same,
(3) a nuclear reprogramming substance capable of inducing an iPS cell from a somatic cell by being combined with the substances (1) and (2) above.

[28] A use of the following (1) and (2) to produce an iPS cell:
(1) one or more substances selected from the group consisting of members of the GLIS family and nucleic acids that encode the same,
(2) one or more substances selected from the group consisting of members of the Klf family and nucleic acids that encode the same, wherein the factors, along with a nuclear reprogramming substance capable of inducing an iPS cell from a somatic cell by being combined with the substances (1) and (2) above, are contacted with a somatic cell.

[29] A use of (1) one or more substances selected from the group consisting of members of the GLIS family and nucleic acids that encode the same to produce an iPS cell, wherein the substances, along with (2) one or more substances selected from the group consisting of members of the Klf family and nucleic acids that encode the same, and a nuclear reprogramming substance capable of inducing an iPS cell from a somatic cell by being combined with the substances (1) and (2) above, are contacted with a somatic cell.

[30] A use of the iPS cell according to [21] or [22] above in producing a somatic cell.

[31] The iPS cell according to [21] or [22] above, wherein the iPS cell serves as a source of cell in producing a somatic cell.

The iPS cell establishment efficiency improver of the present invention is capable of remarkably improving the efficiency of establishment of an iPS cell from a somatic cell, as stated above, and is therefore useful in, for example, applications to human transplantation medicine by autologous transplantation.

BRIEF DESCRIPTION OF THE DRAWINGS

In FIG. 6, "skin" indicates the fibroblast used as a source of somatic cells, and "plasmid" indicates positive controls prepared by amplifying each gene integrated into pMXs.

FIG. 19 shows the number of ESC-like colonies from indicated factor-transduced human dermal fibroblasts (upper: $5×10^4$ cells, lower: $5×10^5$ cells) approximately 30 days after infection.

FIG. 20 shows the ratio of ESC-like colonies from indicated factor-transduced human dermal fibroblasts (upper: $5×10^4$ cells, lower: $5×10^5$ cells) approximately 30 days after infection. The graphs show the mean of three independent experiments with standard deviation (error bar). *:$p<0.05$; **:$p<0.01$

DETAILED DESCRIPTION OF THE INVENTION

Figure 1:
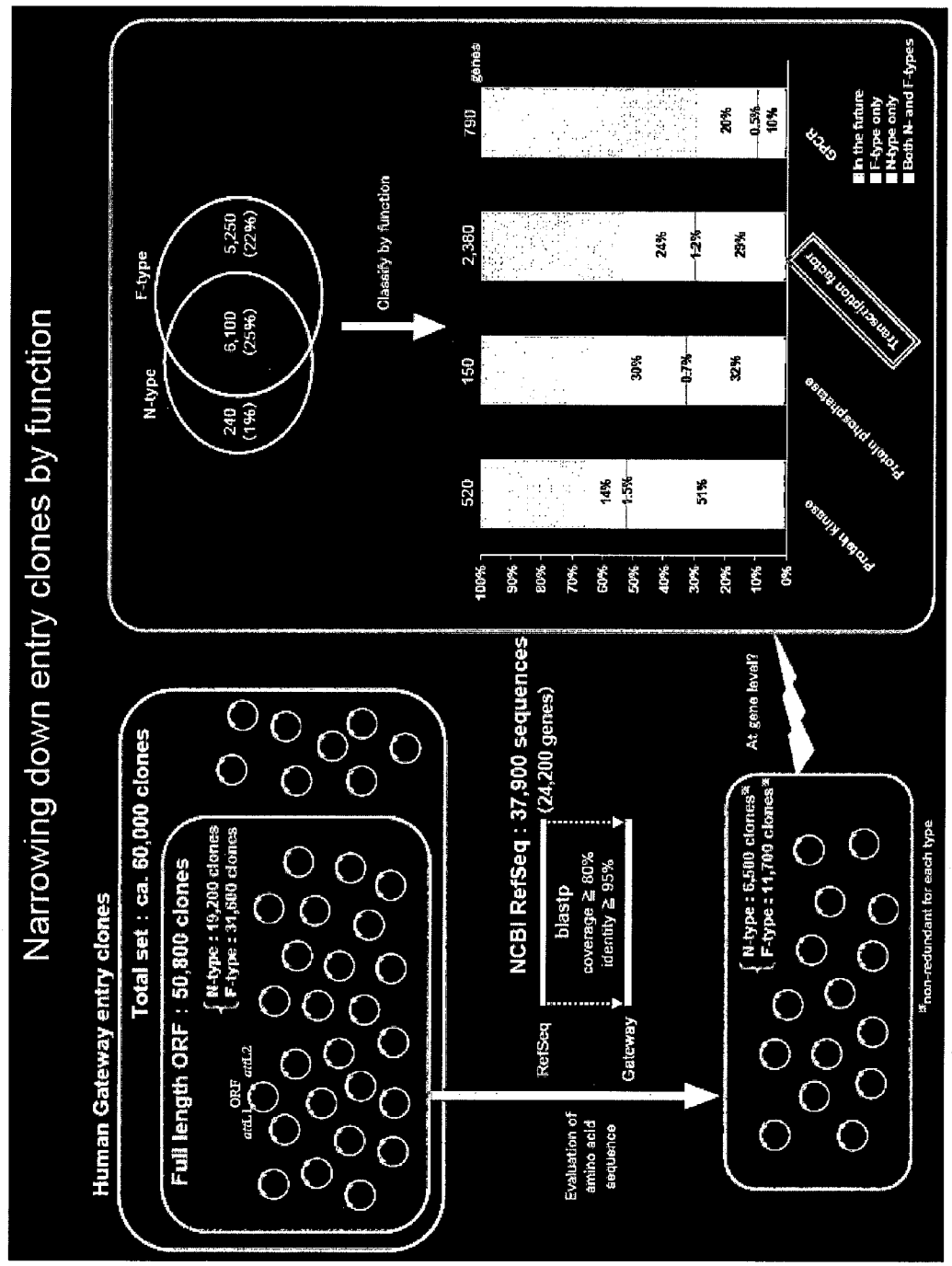
FIG. 1 is a schematic diagram showing the steps for narrowing down entry clones by function from human Gateway® entry clones (N. Goshima et al., Nature methods, 2008).

The present invention provides a method of improving the efficiency of establishment of iPS cells, comprising contacting (1) one or more substances selected from the group consisting of members of the GLIS family and nucleic acids that encode the same, and (2) one or more substances selected from the group consisting of members of the Klf family and nucleic acids that encode the same (hereinafter also referred to as establishment efficiency improving factors of the present invention), with the somatic cell, in the step of nuclear reprogramming of a somatic cell. Because the somatic cell nuclear reprogramming is achieved by contacting a nuclear reprogramming substance with a somatic cell, the present invention also provides a method of producing an iPS cell, comprising contacting (3) a nuclear reprogramming substance capable of inducing an iPS cell from a somatic cell by being combined with the substances (1) and (2) above (hereinafter also simply referred to as a nuclear reprogramming substance), along with the substances (1) and (2) above, with a somatic cell. Herein, a case wherein iPS cells cannot be established with the substance (3) above (nuclear reprogramming substance) alone, but can be established when the nuclear reprogramming substance, along with iPS cell establishment efficiency improving factor of the present invention, is contacted with a somatic cell, is also deemed "an improvement of the efficiency of establishment".

(a) Sources of Somatic Cells

Any cells other than germ cells of mammalian origin (e.g., humans, mice, monkeys, bovines, pigs, rats, dogs etc.) can be used as starting material for the production of iPS cells in the present invention. Examples include keratinizing epithelial cells (e.g., keratinized epidermal cells), mucosal epithelial cells (e.g., epithelial cells of the superficial layer of tongue), exocrine gland epithelial cells (e.g., mammary gland cells), hormone-secreting cells (e.g., adrenomedullary cells), cells for metabolism or storage (e.g., liver cells), intimal epithelial cells constituting interfaces (e.g., type I alveolar cells), intimal epithelial cells of the obturator canal (e.g., vascular endothelial cells), cells having cilia with transporting capability (e.g., airway epithelial cells), cells for extracellular matrix secretion (e.g., fibroblasts), constrictive cells (e.g., smooth muscle cells), cells of the blood and the immune system (e.g., T lymphocytes), sense-related cells (e.g., bacillary cells), autonomic nervous system neurons (e.g., cholinergic neurons), sustentacular cells of sensory organs and peripheral neurons (e.g., satellite cells), nerve cells and glia cells of the central nervous system (e.g., astroglia cells), pigment cells (e.g., retinal pigment epithelial cells), progenitor cells (e.g., tissue progenitor cells) thereof and the like. There is no limitation on the degree of cell differentiation, the age of an animal from which cells are collected and the like; even undifferentiated progenitor cells (including somatic stem cells) and finally differentiated mature cells can be used alike as sources of somatic cells in the present invention. Examples of undifferentiated progenitor cells include tissue stem cells (somatic stem cells) such as nerve stem cells, hematopoietic stem cells, mesenchymal stem cells, and dental pulp stem cells.

The choice of mammal individual as a source of somatic cells is not particularly limited; however, when the iPS cells obtained are to be used for regenerative medicine in humans, it is particularly preferable, from the viewpoint of prevention of graft rejection, to collect the somatic cells from a patient or another person with the same or substantially the same HLA type as that of the patient. "Substantially the same HLA type" as used herein means that the HLA type of donor matches with that of patient to the extent that the transplanted cells, which have been obtained by inducing differentiation of iPS cells derived from the donor's somatic cells, can be engrafted when they are transplanted to the patient with use of immunosuppressant and the like. For example, it includes an HLA type wherein major HLAs (e.g., the three major loci of HLA-A, HLA-B and HLA-DR) are identical (hereinafter the same meaning shall apply) and the like. When the iPS cells obtained are not to be administered (transplanted) to a human, but used as, for example, a source of cells for screening for evaluating a patient's drug susceptibility or adverse reactions, it is likewise desired to collect the somatic cells from the patient or another person with the same genetic polymorphism correlating with the drug susceptibility or adverse reactions.

Somatic cells isolated from a mammal can be pre-cultured using a medium known per se suitable for their cultivation according to the choice of cells before being subjected to the step of nuclear reprogramming. Examples of such media include, but are not limited to, minimal essential medium (MEM) containing about 5 to 20% fetal calf serum (FCS), Dulbecco's modified Eagle medium (DMEM), RPMI1640 medium, 199 medium, F12 medium, and the like. When a transfer reagent such as cationic liposome, for example, is used in bringing the somatic cell into contact with an iPS cell establishment efficiency improving factor of the present invention and a nuclear reprogramming substance (and below-mentioned another iPS cell establishment efficiency improver if required), it is sometimes preferable that the medium have been replaced with a serum-free medium so as to prevent the transfer efficiency from decreasing.

(b) iPS Cell Establishment Efficiency Improving Factors of the Present Invention In the present invention, the GLIS family is a Kruppel-like zinc finger family having five $C_2H_2$ ($Cys_2$-$His_2$-type) Zinc finger regions, which was named after its similarity to Gli transcription factors [Glis=Gli similar, Kim, Y. S. et al., *J. Biol. Chem.*, 277(34), 30901-30913 (2002)]. The GLIS family is membered by transcription factors that positively or negatively control the expression of various genes in the process of embryogenesis. Examples of members of this gene family include, but are not limited to, GLIS family zinc finger 1 (GLIS1), GLIS2, GLIS3 and the like, with preference given to GLIS1. Note that GLIS1 is a gene not expressed in mouse ES cells.

Although the members of the GLIS family used in the present invention may be proteins derived from cells or tissues [e.g., cells or tissues of thymus, bone marrow, spleen, brain, spinal cord, heart, skeletal muscle, kidney, lung, liver, pancreas or prostate, corresponding precursor cells, stem cells or cancer cells thereof, and the like] of optionally chosen mammals (e.g., humans, mice, rats, monkeys, bovines, horses, pigs, dogs and the like) or nucleic acids that encode the same, preference is given to those derived from a human or mouse cell or tissue.

Information on the amino acid sequences and cDNA sequences of members of the GLIS family of human and mouse origin can be acquired with reference to the NCBI accession numbers shown in Table 1. Those skilled in the art are easily able to isolate nucleic acids that encode the respective proteins on the basis of the cDNA sequence information, and to produce recombinant proteins as required.

ment efficiency improving factor of the present invention is contacted with the somatic cell.

Regarding the members of the GLIS family of the present invention and nucleic acids that encode the same, any one of the factors belonging to the family may be used alone, and two or more may be used in combination.

The Klf (Kruppel-like factor) family is membered by transcription factors that control various biological processes such as proliferation, differentiation, genesis, and apoptosis [McConnell, B. B. et al., *Bioassays*, 29: 549-557 (2007)], but their functions remain to be clarified in detail. Examples of members of this gene family include, but are not limited to, Klf1, Klf2, Klf4, Klf5 and the like, with preference given to Klf4. As stated above, the GLIS family has five $C_2H_2$ type Zinc finger regions, whereas the Klf family has three $C_2H_2$ type Zinc finger regions.

Yamanaka et al. hypothesized that the same four genes (Oct3/4, Sox2, Klf4 and c-Myc) could be substituted by other genes belonging to the same respective families, and showed that iPS cells could be established even when Klf4 was replaced with Klf1, Klf2 or Klf5 [WO 2007/069666 A1; Nakagawa, M. et al., Nat. Biotethnol., 26: 101-106 (2008)]. When ES cells are treated with retinoic acid to induce their differentiation, not only Klf4, but also Klf2 and Klf5 decrease their expression. Taking note of this fact, a group of Jiang et al. recently knocked down Klf2, Klf4 and Klf5 simultaneously, and found that differentiation was induced in the ES cells, showing that at least some of the members of the Klf family, such as Klf2 and Klf5, can functionally substitute for Klf4 in ES cells [Jiang, J. et al., Nat. Cell Biol., 10: 353-360 (2008)]. They proceeded to transfer the Klf2 or Klf5 gene, or other transcription factors or epigenetic regulatory factors, along with the three genes Oct3/4, Sox2 and c-Myc, into MEF, confirming that Klf2 and Klf5 can substitute for Klf4, and finding that Esrrb, an orphan nuclear receptor resembling to estrogen receptors, is also capable of substituting for Klf4 [Feng, B. et al., Nat. Cell Biol., 11: 197-203 (2009)]. These findings lead to the notion that Klf1, Klf2, Klf5, and even Esrrb, also possess the effect of Klf4 confirmed in Examples

TABLE 1

| Gene code name | Humans | | Mice | |
|---|---|---|---|---|
| | cDNA | Protein | cDNA | Protein |
| GLIS1 | NM_147193 (SEQ ID NO: 1) | NP_671726 (SEQ ID NO: 2) | NM_147221 (SEQ ID NO: 3) | NP_671754 (SEQ ID NO: 4) |
| GLIS2 | NM_032575 | NP_115964 | NM_031184 | NP_112461 |
| GLIS3 | NM_001042413 | NP_001035878 | NM_175459 | NP_780668 |

A natural or artificial mutant protein having an identity of 90% or more, preferably 95% or more, more preferably 98% or more, particularly preferably 99% or more, to each amino acid sequence shown above, and possessing an iPS cell establishment efficiency improving effect equivalent to that of the wild-type protein, and a nucleic acid that encodes the same, can also be utilized as an iPS cell establishment efficiency improving factor of the present invention. Here, the effect in improving the efficiency of establishment of iPS cells can be verified by comparing the number of emerging iPS cell colonies between a case wherein only specified reprogramming factors (e.g., the 2 factors Oct3/4 and Sox, the 3 factors consisting of the 2 factors and c-Myc, and the like) are transferred to the somatic cell, and a case wherein in addition to transferring the reprogramming factors, an iPS cell establish-given herein (an improvement of the efficiency of establishment of iPS cells with the use in combination with the GLIS family).

Although the members of the Klf family used in the present invention may be proteins derived from cells or tissues [e.g., cells or tissues of thymus, bone marrow, spleen, brain, spinal cord, heart, skeletal muscle, kidney, lung, liver, pancreas or prostate, corresponding precursor cells, stem cells or cancer cells thereof, and the like] of optionally chosen mammals (e.g., humans, mice, rats, monkeys, bovines, horses, pigs, dogs and the like) or nucleic acids that encode the same, preference is given to those of human or mouse origin.

Information on the amino acid sequences and cDNA sequences of members of the Klf family of human and mouse origin can be acquired with reference to the NCBI accession numbers shown in Table 2. Those skilled in the art are easily able to isolate nucleic acids that encode the respective proteins on the basis of the cDNA sequence information, and to produce recombinant proteins as required.

TABLE 2

| Gene code name | Humans | | Mice | |
|---|---|---|---|---|
| | cDNA | Protein | cDNA | Protein |
| Klf1 | NM_006563 | NP_006554 | NM_010635 | NP_034765 |
| Klf2 | NM_016270 | NP_057354 | NM_008452 | NP_032478 |
| Klf4 | NM_004235 | NP_004226 | NM_010637 | NP_034767 |
| | (SEQ ID NO: 5) | (SEQ ID NO: 6) | (SEQ ID NO: 7) | (SEQ ID NO: 8) |
| Klf5 | NM_001730 | NP_001721 | NM_009769 | NP_033899 |

A natural or artificial mutant protein having an identity of 90% or more, preferably 95% or more, more preferably 98% or more, particularly preferably 99% or more, to each amino acid sequence shown above, and possessing an iPS cell establishment efficiency improving effect equivalent to that of the wild-type protein, and a nucleic acid that encodes the same, can also be utilized as an iPS cell establishment efficiency improving factor of the present invention.

Regarding the members of the Klf family of the present invention and nucleic acids that encode the same, any one of the factors belonging to the family may be used alone, and two or more may be used in combination.

Provided that the somatic cell to undergo nuclear reprogramming is endogenously expressing one or more of the constituents of any one of members of the GLIS family, or members of the Klf family, which are the above-described iPS cell establishment efficiency improving factors of the present invention, at a level sufficient to improve the establishment efficiency, a combination of only the remaining constituents excluding the endogenously expressed constituents can also be included in the scope of "iPS cell establishment efficiency improving factor" in the present invention.

Transfer of an iPS cell establishment efficiency improving factor of the present invention in the form of a protein to a somatic cell can be achieved using a method known per se for protein transfer into a cell. Such methods include, for example, the method using a protein transfer reagent, the method using a protein transfer domain (PTD) or cell penetrating peptide (CPP) fusion protein, the microinjection method and the like. Protein transfer reagents are commercially available, including those based on a cationic lipid, such as BioPOTER Protein Delivery Reagent (Gene Therapy Systems), Pro-Ject™ Protein Transfection Reagent (PIERCE) and ProVectin (IMGENEX); those based on a lipid, such as Profect-1 (Targeting Systems); those based on a membrane-permeable peptide, such as Penetrain Peptide (Q biogene) and Chariot Kit (Active Motif), GenomONE (ISHIHARA SANGYO KAISHA, LTD.) utilizing HVJ envelope (inactivated hemagglutinating virus of Japan) and the like. The transfer can be achieved per the protocols attached to these reagents, a common procedure being as described below. A proteinous iPS cell establishment efficiency improving factor of the present invention is diluted in an appropriate solvent (e.g., a buffer solution such as PBS or HEPES), a transfer reagent is added, the mixture is incubated at room temperature for about 5 to 15 minutes to form a complex, this complex is added to cells after exchanging the medium with a serum-free medium, and the cells are incubated at 37° C. for one to several hours. Thereafter, the medium is removed and replaced with a serum-containing medium.

Developed PTDs include those using transcellular domains of proteins such as drosophila-derived AntP, HIV-derived TAT (Frankel, A. et al, Cell 55, 1189-93 (1988) or Green, M. & Loewenstein, P. M. Cell 55, 1179-88 (1988)), Penetratin (Derossi, D. et al, J. Biol. Chem. 269, 10444-50 (1994)), Buforin II (Park, C. B. et al. Proc. Natl. Acad. Sci. USA 97, 8245-50 (2000)), Transportan (Pooga, M. et al. FASEB J. 12, 67-77 (1998)), MAP (model amphipathic peptide) (Oehlke, J. et al. Biochim. Biophys. Acta. 1414, 127-39 (1998)), K-FGF (Lin, Y. Z. et al. J. Biol. Chem. 270, 14255-14258 (1995)), Ku70 (Sawada, M. et al. Nature Cell Biol. 5, 352-7 (2003)), Prion (Lundberg, P. et al. Biochem. Biophys. Res. Commun. 299, 85-90 (2002)), pVEC (Elmquist, A. et al. Exp. Cell Res. 269, 237-44 (2001)), Pep-1 (Morris, M. C. et al. Nature Biotechnol. 19, 1173-6 (2001)), Pep-7 (Gao, C. et al. Bioorg. Med. Chem. 10, 4057-65 (2002)), SynB1 (Rousselle, C. et al. Mol. Pharmacol. 57, 679-86 (2000)), HN-I (Hong, F. D. & Clayman, G L. Cancer Res. 60, 6551-6 (2000)), and HSV-derived VP22. CPPs derived from the PTDs include polyarginines such as 11R (Cell Stem Cell, 4, 381-384 (2009)) and 9R (Cell Stem Cell, 4, 472-476 (2009)).

A fused protein expression vector incorporating cDNA of an iPS cell establishment efficiency improving factor of the present invention and PTD sequence or CPP sequence is prepared, and recombination expression is performed using the vector. The fused protein is recovered and used for transfer. Transfer can be performed in the same manner as above except that a protein transfer reagent is not added.

Microinjection, a method of placing a protein solution in a glass needle having a tip diameter of about 1 μm, and injecting the solution into a cell, ensures the transfer of the protein into the cell.

Other useful methods of protein transfer include electroporation, the semi-intact cell method [Kano, F. et al. Methods in Molecular Biology, Vol. 322, 357-365 (2006)], transfer using the Wr-t peptide [Kondo, E. et al., Mol. Cancer. Ther. 3(12), 1623-1630 (2004)] and the like.

The protein transferring operation can be performed one or more optionally chosen times (e.g., once or more to 10 times or less, or once or more to 5 times or less and the like). Preferably, the transferring operation can be performed twice or more (e.g., 3 times or 4 times) repeatedly. The time interval for repeated transferring operation is, for example, 6 to 48 hours, preferably 12 to 24 hours.

When iPS cell establishment efficiency is emphasized, it is preferable that an iPS cell establishment efficiency improving factor of the present invention be used not as a protein, but in the form of a nucleic acid that encodes the same. The nucleic acid may be a DNA or RNA, and may be a DNA/RNA chimera, with preference given to a DNA. The nucleic acid may be double-stranded or single-stranded. In the case of a double strand, the same may be a double-stranded DNA, a double-stranded RNA, or a DNA/RNA hybrid. Preferably, the nucleic acid is a double-stranded DNA, particularly a cDNA.

A nucleic acid-based iPS cell establishment efficiency improving factor of the present invention can be cloned from, for example, a cDNA derived from cells or tissues [e.g., cells or tissues of thymus, bone marrow, spleen, brain, spinal cord, heart, skeletal muscle, kidney, lung, liver, pancreas or prostate, corresponding precursor cells, stem cells or cancer cells thereof, and the like] of humans or other mammals (e.g., mouse, rats, monkeys, pigs, dogs and the like), according to a conventional method.

Transfer of an iPS cell establishment efficiency improving factor of the present invention to a somatic cell can be achieved using a method known per se for gene transfer to cells. A nucleic acid that encodes an iPS cell establishment efficiency improving factor of the present invention is inserted into an appropriate expression vector comprising a promoter capable of functioning in a host somatic cell. Useful expression vectors include, for example, viral vectors such as retrovirus, lentivirus, adenovirus, adeno-associated virus, herpesvirus and Sendai virus, plasmids for the expression in animal cells (e.g., pA1-11, pXT1, pRc/CMV, pRc/RSV, pcDNAI/Neo) and the like.

The type of a vector to be used can be chosen as appropriate according to the intended use of the iPS cell to be obtained. Useful vectors include adenovirus vector, plasmid vector, adeno-associated virus vector, retrovirus vector, lentivirus vector, Sendai virus vector and the like.

Examples of promoters used in expression vectors include the EF1α promoter, the CAG promoter, the SRα promoter, the SV40 promoter, the LTR promoter, the CMV (cytomegalovirus) promoter, the RSV (Rous sarcoma virus) promoter, the MoMuLV (Moloney mouse leukemia virus) LTR, the HSV-TK (herpes simplex virus thymidine kinase) promoter and the like, with preference given to the EF1α promoter, the CAG promoter, the MoMuLV LTR, the CMV promoter, the SRα promoter and the like.

The expression vector may contain as desired, in addition to a promoter, an enhancer, a polyadenylation signal, a selectable marker gene, a SV40 replication origin and the like. Examples of selectable marker genes include the dihydrofolate reductase gene, the neomycin resistant gene, the puromycin resistant gene and the like.

Regarding the nucleic acids that encode iPS cell establishment efficiency improving factors of the present invention, any one may be integrated onto an expression vector alone, and some in combination may be integrated onto one expression vector. Furthermore, the nucleic acid(s) may be integrated onto one expression vector along with one or more reprogramming genes.

In the above-described procedure, when genes of iPS cell establishment efficiency improving factors and reprogramming factors of the present invention are integrated in combination into one expression vector, these genes can preferably be integrated into the expression vector via a sequence enabling polycistronic expression. Using a sequence enabling polycistronic expression makes it possible to more efficiently express a plurality of genes integrated in one expression vector. Useful sequences enabling polycistronic expression include, for example, the 2A sequence of foot-and-mouth disease virus (SEQ ID NO:9; PLoS ONE 3, e2532, 2008, Stem Cells 25, 1707, 2007), the IRES sequence (U.S. Pat. No. 4,937,190) and the like, with preference given to the 2A sequence.

An expression vector comprising a nucleic acid that encodes an iPS cell establishment efficiency improving factor of the present invention can be introduced into a cell by a technique known per se according to the choice of vector. In the case of a viral vector, for example, a plasmid containing the nucleic acid is introduced into an appropriate packaging cell (e.g., Plat-E cell) or a complementary cell line (e.g., 293-cells), the viral vector produced in the culture supernatant is recovered, and the vector is infected to the cell by a method suitable for the viral vector. For example, specific means using a retroviral vector are disclosed in WO2007/69666, Cell, 126, 663-676 (2006) and Cell, 131, 861-872 (2007). Specific means using a lentivirus vector is disclosed in Science, 318, 1917-1920 (2007). When iPS cells are utilized as a source of cells for regenerative medicine, the expression (reactivation) of an iPS cell establishment efficiency improving factor of the present invention or the activation of an endogenous gene present in the vicinity of the site where the exogenous gene is integrated potentially increases the risk of carcinogenesis in tissues regenerated from differentiated cells of iPS cell derivation. Therefore, the nucleic acid that encodes an iPS cell establishment efficiency improving factor of the present invention is preferably expressed transiently, without being integrated into the chromosome of the cells. From this viewpoint, use of an adenoviral vector, whose integration into chromosome is rare, is preferred. Specific means using an adenoviral vector is described in Science, 322, 945-949 (2008). Because an adeno-associated viral vector is also low in the frequency of integration into chromosome, and is lower than adenoviral vectors in terms of cytotoxicity and inflammation-inducibility, it can be mentioned as another preferred vector. Because Sendai viral vector is capable of being stably present outside the chromosome, and can be degraded and removed using an siRNA as required, it is preferably utilized as well. Regarding a Sendai viral vector, one described in J. Biol. Chem., 282, 27383-27391 (2007), Proc. Jpn. Acad., Ser. B 85, 348-362 (2009) or JP-B-3602058 can be used.

When a retroviral vector or a lentiviral vector is used, even if silencing of the transgene has occurred, it possibly becomes reactivated. Therefore, for example, a method can be used preferably wherein a nucleic acid encoding an iPS cell establishment efficiency improving factor of the present invention is cut out using the Cre-loxP system, when becoming unnecessary. That is, with loxP sequences arranged on both ends of the nucleic acid in advance, iPS cells are induced, thereafter the Cre recombinase is allowed to act on the cells using a plasmid vector or adenoviral vector, and the region sandwiched by the loxP sequences can be cut out. Because the enhancer-promoter sequence of the LTR U3 region possibly upregulates a host gene in the vicinity thereof by insertion mutation, it is more preferable to avoid the expression regulation of the endogenous gene by the LTR outside of the loxP sequence remaining in the genome without being cut out, using a 3'-self-inactivated (SIN) LTR prepared by deleting the sequence, or substituting the sequence with a polyadenylation sequence such as of SV40. Specific means using the Cre-loxP system and SIN LTR is disclosed in Soldner et al., Cell, 136: 964-977 (2009), Chang et al., Stem Cells, 27: 1042-1049 (2009) and the like.

Meanwhile, being a non-viral vector, a plasmid vector can be transferred into a cell using the lipofection method, liposome method, electroporation method, calcium phosphate co-precipitation method, DEAE dextran method, microinjection method, gene gun method and the like. Specific means using a plasmid as a vector are described in, for example, Science, 322, 949-953 (2008) and the like.

When a plasmid vector, an adenovirus vector and the like are used, the transfection can be performed once or more optionally chosen times (e.g., once to 10 times, once to 5 times or the like). When two or more kinds of expression vectors are introduced into a somatic cell, it is preferable that these all kinds of expression vectors be concurrently introduced into a somatic cell; however, even in this case, the transfection can be performed once or more optionally chosen times (e.g., once to 10 times, once to 5 times or the like), preferably the transfection can be repeatedly performed twice or more (e.g., 3 times or 4 times).

Also when an adenovirus or a plasmid is used, the transgene can get integrated into chromosome; therefore, it is eventually necessary to confirm the absence of insertion of the gene into chromosome by Southern blotting or PCR. For this reason, like the aforementioned Cre-loxP system, it can be advantageous to use a means wherein the transgene is integrated into chromosome, thereafter the gene is removed. In another preferred mode of embodiment, a method can be used wherein the transgene is integrated into chromosome using a transposon, thereafter a transposase is allowed to act on the cell using a plasmid vector or adenoviral vector so as to completely eliminate the transgene from the chromosome. As examples of preferable transposons, piggyBac, a transposon derived from a lepidopterous insect, and the like can be mentioned. Specific means using the piggyBac transposon is disclosed in Kaji, K. et al., *Nature,* 458: 771-775 (2009), Woltjen et al., *Nature,* 458: 766-770 (2009).

Another preferable non-integration type vector is an episomal vector, which is capable of self-replication outside the chromosome. Specific means using an episomal vector is disclosed in Yu et al., *Science,* 324, 797-801 (2009). As required, an expression vector may be constructed by inserting a nucleic acid that encodes an iPS cell establishment efficiency improving factor of the present invention into an episomal vector having loxP sequences placed in the same orientation on the 5' and 3' sides of the vector constituent essential for the replication of the episomal vector, and this can be transferred to a somatic cell.

Examples of the episomal vector include a vector comprising as a vector component a sequence derived from EBV, SV40 and the like necessary for self-replication. The vector component necessary for self-replication is specifically exemplified by a replication origin and a gene that encodes a protein that binds to the replication origin to control the replication; examples include the replication origin oriP and the EBNA-1 gene for EBV, and the replication origin on and the SV40 large T antigen gene for SV40.

The episomal expression vector contains a promoter that controls the transcription of a nucleic acid that encodes an iPS cell establishment efficiency improving factor of the present invention. The promoter used may be as described above. The episomal expression vector may further contain as desired an enhancer, a polyadenylation signal, a selection marker gene and the like, as described above. Examples of the selection marker gene include the dihydrofolate reductase gene, the neomycin resistance gene and the like.

The loxP sequences useful in the present invention include, in addition to the bacteriophage P1-derived wild type loxP sequence (SEQ ID NO:10), optionally chosen mutant loxP sequences capable of deleting the sequence flanked by the loxP sequence by recombination when placed in the same orientation at positions flanking a vector component necessary for the replication of the transgene. Examples of such mutant loxP sequences include lox71 (SEQ ID NO:11), mutated in 5' repeat, lox66 (SEQ ID NO:12), mutated in 3' repeat, and lox2272 and lox511, mutated in spacer portion. Although the two loxP sequences placed on the 5' and 3' sides of the vector component may be identical or not, the two mutant loxP sequences mutated in spacer portion must be identical (e.g., a pair of lox2272 sequences, a pair of lox511 sequences). Preference is given to a combination of a mutant loxP sequence mutated in 5' repeat (e.g., lox71) and a mutant loxP sequence mutated in 3' repeat (e.g., lox66). In this case, the loxP sequences remaining on the chromosome as a result of recombination have double mutations in the repeats on the 5' side and 3' side, and are therefore unlikely to be recognized by Cre recombinase, thus reducing the risk of causing a deletion mutation in the chromosome due to unwanted recombination. When the mutant loxP sequences lox71 and lox66 are used in combination, each may be placed on any of the 5' and 3' sides of the aforementioned vector component, but it is necessary that the mutant loxP sequences be inserted in an orientation such that the mutated sites would be located at the outer ends of the respective loxP sequences.

Each of the two loxP sequences is placed in the same orientation on the 5' and 3' sides of a vector constituent essential for the replication of the transgene (i.e., a replication origin, or a gene sequence that encodes a protein that binds to the replication origin to control the replication). The vector constituent flanked by the loxP sequences may be either the replication origin or a gene sequence that encodes a protein that binds to a replication origin to control the replication, or both.

The episomal vector can be introduced into the cell using, for example, the lipofection method, liposome method, electroporation method, calcium phosphate co-precipitation method, DEAE dextran method, microinjection method, gene gun method and the like. Specifically, for example, methods described in *Science,* 324: 797-801 (2009) and elsewhere can be used.

Whether or not the vector component necessary for the replication of the transgene has been removed from the iPS cell can be confirmed by performing a Southern blot analysis or PCR analysis using a nucleic acid comprising a nucleotide sequence in the vector component and/or in the vicinity of loxP sequence as a probe or primer, with the episome fraction isolated from the iPS cell as a template, and determining the presence or absence of a band or the length of the band detected. The episome fraction can be prepared by a method obvious in the art; for example, methods described in *Science,* 324: 797-801 (2009) and elsewhere can be used.

(c) Nuclear Reprogramming Substances

In the present invention, "a nuclear reprogramming substance" refers to any substance(s) capable of inducing an iPS cell from a somatic cell, which may be composed of any substance such as a proteinous factor or a nucleic acid that encodes the same (including forms integrated in a vector), or a low-molecular compound, when transferred to the somatic cell, or when contacted with the somatic cell along with establishment efficiency improving factors of the present invention [(1) one or more substances selected from the group consisting of members of the GLIS family and nucleic acids that encode the same, and (2) one or more substances selected from the group consisting of members of the Klf family and nucleic acids that encode the same]. As a known nuclear reprogramming substance that is a proteinous factor or a nucleic acid that encodes the same, the following combinations, for example, are preferable (hereinafter, only the names for proteinous factors are shown).

(1) Oct3/4, Klf4, c-Myc
(2) Oct3/4, Klf4, c-Myc, Sox2 (Sox2 is replaceable with Sox1, Sox3, Sox15, Sox17 or Sox18; Klf4 is replaceable with Klf1, Klf2 or Klf5; c-Myc is replaceable with T58A (active mutant), or L-Myc)
(3) Oct3/4, Klf4, c-Myc, Sox2, Fbx15, Nanog, ERas, Tcl1
(4) Oct3/4, Klf4, c-Myc, Sox2, TERT, SV40 Large T antigen (hereinafter SV40LT)
(5) Oct3/4, Klf4, c-Myc, Sox2, TERT, HPV16 E6

(6) Oct3/4, Klf4, c-Myc, Sox2, TERT, HPV16 E7
(7) Oct3/4, Klf4, c-Myc, Sox2, TERT, HPV16 E6, HPV16 E7
(8) Oct3/4, Klf4, c-Myc, Sox2, TERT, Bmil
[For more information on the factors shown above, see WO 2007/069666 (for information on replacement of Sox2 with Sox18 and replacement of Klf4 with Klf1 or Klf5 in the combination (2) above, see *Nature Biotechnology*, 26, 101-106 (2008)); for the combination "Oct3/4, Klf4, c-Myc, Sox2", see also Cell, 126, 663-676 (2006), *Cell,* 131, 861-872 (2007) and the like; for the combination "Oct3/4, Klf2 (or Klf5), c-Myc, Sox2", see also *Nat. Cell Biol.,* 11, 197-203 (2009); for the combination "Oct3/4, Klf4, c-Myc, Sox2, hTERT, SV40 LT", see also *Nature,* 451, 141-146 (2008).]
(9) Oct3/4, Klf4, Sox2 (see *Nature Biotechnology*, 26, 101-106 (2008))
(10) Oct3/4, Sox2, Nanog, Lin28 (see *Science,* 318, 1917-1920 (2007))
(11) Oct3/4, Sox2, Nanog, Lin28, hTERT, SV40LT (see *Stem Cells,* 26, 1998-2005 (2008))
(12) Oct3/4, Klf4, c-Myc, Sox2, Nanog, Lin28 (see *Cell Research* 18 (2008) 600-603)
(13) Oct3/4, Klf4, c-Myc, Sox2, SV40LT (see *Stem Cells,* 26, 1998-2005 (2008))
(14) Oct3/4, Klf4 (see *Nature* 454:646-650 (2008), *Cell Stem Cell,* 2, 525-528 (2008)))
(15) Oct3/4, c-Myc (see *Nature* 454:646-650 (2008))
(16) Oct3/4, Sox2 (see *Nature,* 451, 141-146 (2008), WO2008/118820)
(17) Oct3/4, Sox2, Nanog (see WO2008/118820)
(18) Oct3/4, Sox2, Lin28 (see WO2008/118820)
(19) Oct3/4, Sox2, c-Myc, Esrrb (Here, Esrrb can be substituted by Esrrg, see *Nat. Cell Biol.,* 11, 197-203 (2009))
(20) Oct3/4, Sox2, Esrrb (see *Nat. Cell Biol.,* 11, 197-203 (2009))
(21) Oct3/4, Klf4, L-Myc (see *Proc. Natl. Acad. Sci. USA.,* 107(32), 14152-14157 (2010))
(22) Oct3/4, Klf4, Sox2, L-Myc, Lin28 (see WO2011/016588)
(23) Oct3/4, Nanog
(24) Oct3/4 (*Cell* 136: 411-419 (2009), *Nature,* 08436, doi: 10.1038 published online (2009)
(25) Oct3/4, Klf4, c-Myc, Sox2, Nanog, Lin28, SV40LT (see *Science,* 324: 797-801 (2009))

In (1)-(25) above, Oct3/4 may be replaced with another member of the Oct family, for example, Oct1A, Oct6 or the like. Sox2 (or Sox1, Sox3, Sox15, Sox17, Sox18) may be replaced with another member of the Sox family, for example, Sox7 or the like. Furthermore, provided that c-Myc or Lin28 is included as a nuclear reprogramming substance in the combinations (1)-(25) above, L-Myc or Lin28B can be used in place of c-Myc or Lin28, respectively.

When the combinations of factors (1)-(25) above include members of the Klf family, the "nuclear reprogramming substance" used in combination with an iPS cell establishment efficiency improving factor of the present invention is suitably one containing a factor other than these members of the Klf family. When the combinations (1)-(25) above do not include a member of the Klf family, nuclear reprogramming substances used in combination with iPS cell establishment efficiency improving factors of the present invention may be a combination of the factors.

Combinations further comprising another optionally chosen substance, in addition to the aforementioned nuclear reprogramming substances, are also suitably used as a "nuclear reprogramming substance" in the present invention. Provided that the somatic cell to undergo nuclear reprogramming is endogenously expressing one or more of the constituents of any one of (1) to (25) above at a level sufficient to cause nuclear reprogramming, a combination of only the remaining constituents excluding the one or more constituents can also be included in the scope of "nuclear reprogramming substances" in the present invention.

Of these combinations, one or more substances selected from among members of the Oct family, members of the Sox family, members of the Myc family, members of the Lin28 family and Nanog, for example, are preferable nuclear reprogramming substances, with greater preference given to the combination of Oct3/4 and Sox2, the combination of Oct3/4, Sox2 and c-Myc, the combination of Oct3/4, Sox2 and L-Myc, or the combination of Oct3/4, Sox2, L-Myc and Lin28.

While promoting the establishment of iPS cells, c-Myc also promotes the generation of non-iPS transformed cells (partially reprogrammed cells, nullipotent transformed cells). The present inventors not only demonstrated that co-expressing GLIS1 with Oct3/4, Sox2 and Klf4 dramatically promotes the establishment of iPS cells from mouse and human adult skin fibroblasts, but also revealed that GLIS1, unlike c-Myc, does not promote the aforementioned genesis of non-iPS transformed cells. Therefore, it is particularly preferable to use GLIS1 without using c-Myc.

Information on the mouse and human cDNA sequences of the aforementioned each proteinous factor is available with reference to the NCBI accession numbers mentioned in WO 2007/069666 (in the publication, Nanog is described as ECAT4. Mouse and human cDNA sequence information on Lin28, Lin28b, Esrrb, Esrrg and L-Myc can be acquired by referring to the following NCBI accession numbers, respectively); those skilled in the art are easily able to isolate these cDNAs.

| Name of gene | Mouse | Human |
|---|---|---|
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |
| L-Myc | NM_008506 | NM_001033081 |

A proteinous factor for use as a nuclear reprogramming substance can be prepared by inserting the cDNA obtained into an appropriate expression vector, introducing the vector into a host cell, and recovering the recombinant proteinous factor from the cultured cell or its conditioned medium. Meanwhile, when a nucleic acid that encodes a proteinous factor is used as a nuclear reprogramming substance, the cDNA obtained is inserted into a viral vector, episomal vector or plasmid vector in the same manner as with the above-described case of the nucleic acid-based iPS cell establishment efficiency improving factor of the present invention to construct an expression vector, which is subjected to the nuclear reprogramming step. The aforementioned Cre-loxP system or piggyBac transposon system can also be utilized as required. When two or more nucleic acids that encode two or more proteinous factors are transferred to a cell as nuclear reprogramming substances, the different nucleic acids may be carried by separate vectors, or the plurality of nucleic acids may be joined in tandem to obtain a polycistronic vector. In the latter case, to allow efficient polycistronic expression, it is desirable that the 2A self-cleaving peptide of foot-and-mouth disease virus be inserted between the nucleic acids (see, for example, *Science,* 322, 949-953, 2008).

Contact of a nuclear reprogramming substance with a somatic cell can be achieved (a) in the same manner as with the above-described proteinous iPS cell establishment efficiency improving factor of the present invention when the substance is a proteinous factor, or (b) in the same manner as with the above-described nucleic acid-based iPS cell establishment efficiency improving factor of the present invention when the substance is a nucleic acid that encodes a proteinous factor. (c) When the nuclear reprogramming substance is a low-molecular compound, contacting with somatic cells can be achieved by dissolving the low-molecular compound at an appropriate concentration in an aqueous or non-aqueous solvent, adding the solution to a medium suitable for cultivation of somatic cells isolated from human or the other mammals [e.g., minimal essential medium (MEM) comprising about 5 to 20% fetal bovine serum, Dulbecco's modified Eagle medium (DMEM), RPMI1640 medium, 199 medium, F12 medium, and the like] so that the nuclear reprogramming substance concentration will fall in a range that is sufficient to cause nuclear reprogramming in somatic cells and does not cause cytotoxicity, and culturing the cells for a given period. The nuclear reprogramming substance concentration varies depending on the kind of nuclear reprogramming substance used, and is chosen as appropriate over the range of about 0.1 nM to about 100 nM. Duration of contact is not particularly limited, as far as it is sufficient to cause nuclear reprogramming of the cells; usually, the nuclear reprogramming substance may be allowed to be co-present in the medium until a positive colony emerges.

(d) Other iPS Cell Establishment Efficiency Improvers

In recent years, various substances that improve the efficiency of establishment of iPS cells, which has traditionally been low, have been proposed one after another. When contacted with a somatic cell along with the aforementioned iPS cell establishment efficiency improving factor of the present invention, other iPS cell establishment efficiency improvers are expected to further raise the efficiency of establishment of iPS cells.

Examples of the other iPS cell establishment efficiency improvers include, but are not limited to, histone deacetylase (HDAC) inhibitors except for VPA [e.g., low-molecular inhibitors such as trichostatin A (TSA), sodium butyrate, MC 1293, and M344, nucleic acid-based expression inhibitors such as siRNAs and shRNAs against HDAC (e.g., HDAC1 siRNA Smartpool®(Millipore), HuSH 29mer shRNA Constructs against HDAC1 (OriGene) and the like), and the like], DNA methyltransferase inhibitors [e.g., 5'-azacytidine (5'-azaC) [*Nat. Biotechnol.*, 26(7): 795-797 (2008)], G9a histone methyltransferase inhibitors [e.g., low-molecular inhibitors such as BIX-01294 (*Cell Stem Cell*, 2: 525-528 (2008)), nucleic acid-based expression inhibitors such as siRNAs and shRNAs against G9a [e.g., G9a siRNA (human) (Santa Cruz Biotechnology) and the like) and the like], L-channel calcium agonists (e.g., Bayk8644) [*Cell Stem Cell*, 3, 568-574 (2008)], p53 inhibitors e.g., siRNA, shRNA, dominant negative mutants etc. against p53 (*Cell Stem Cell*, 3, 475-479 (2008)); *Nature* 460, 1132-1135 (2009))], Wnt signaling activator (e.g., soluble Wnt3a) [*Cell Stem Cell*, 3, 132-135 (2008)], 2i/LIF [2i is an inhibitor of mitogen-activated protein kinase signaling and glycogen synthase kinase-3, *PloS Biology*, 6(10), 2237-2247 (2008)], ES cell-specific miRNA [e.g., miR-302-367 cluster (*Mol. Cell. Biol. doi:*10.1128/ MCB.00398-08); miR-302 (*RNA* (2008) 14: 1-10); miR-291-3p, miR-294 and miR-295 (*Nat. Biotechnol.* 27: 459-461 (2009)] and the like. As mentioned above, the nucleic acid-based expression inhibitors may be in the form of expression vectors harboring a DNA that encodes an siRNA or shRNA.

Of the aforementioned constituents of nuclear reprogramming substances, SV40 large T, for example, can also be included in the scope of iPS cell establishment efficiency improvers because they are auxiliary factors unessential for the nuclear reprogramming of somatic cells. While the mechanism of nuclear reprogramming remains unclear, it does not matter whether auxiliary factors, other than the factors essential for nuclear reprogramming, are deemed nuclear reprogramming substances or iPS cell establishment efficiency improvers. Hence, because the somatic cell nuclear reprogramming process is taken as an overall event resulting from contact of nuclear reprogramming substances and an iPS cell establishment efficiency improver with somatic cells, it does not seem always essential for those skilled in the art to distinguish between the two.

Contact of an iPS cell establishment efficiency improver with a somatic cell can be achieved in the same manner as with the above-described iPS cell establishment efficiency improving factor of the present invention and nuclear reprogramming substance when the improver is (a) a proteinous factor, (b) a nucleic acid that encodes the proteinous factor, or (c) a low-molecular compound, respectively.

iPS cell establishment efficiency improvers, including iPS cell establishment efficiency improving factors of the present invention, may be contacted with the somatic cell simultaneously with the nuclear reprogramming substance, and either one may be contacted in advance, as far as the efficiency of iPS cell establishment from a somatic cell improves significantly compared with the efficiency obtained in the absence of the substance. In an embodiment, for example, when the nuclear reprogramming substance is a nucleic acid that encodes a proteinous factor and the iPS cell establishment efficiency improver is a chemical inhibitor, the iPS cell establishment efficiency improver can be added to the medium after the cell is cultured for a given length of time following the gene transfer treatment, because the nuclear reprogramming substance involves a given length of time lag from the gene transfer treatment to the mass-expression of the proteinous factor, whereas the iPS cell establishment efficiency improver is capable of rapidly acting on the cell. In another embodiment, when a nuclear reprogramming substance and an iPS cell establishment efficiency improver are both used in the form of a viral or plasmid vector, for example, both may be simultaneously introduced into the cell.

(e) Improving the Establishment Efficiency by Culture Conditions iPS cell establishment efficiency can further be improved by culturing the cells under hypoxic conditions in the nuclear reprogramming process for somatic cells (see *Cell Stem Cell*, 5, p 237-241 (2009)). As mentioned herein, the term "hypoxic conditions" means that the ambient oxygen concentration as of the time of cell culture is significantly lower than that in the atmosphere. Specifically, conditions involving lower oxygen concentrations than the ambient oxygen concentrations in the 5-10% $CO_2$/95-90% air atmosphere, which is commonly used for ordinary cell culture, can be mentioned; examples include conditions involving an ambient oxygen concentration of 18% or less. Preferably, the ambient oxygen concentration is 15% or less (e.g., 14% or less, 13% or less, 12% or less, 11% or less and the like), 10% or less (e.g., 9% or less, 8% or less, 7% or less, 6% or less and the like), or 5% or less (e.g., 4% or less, 3% or less, 2% or less and the like). The ambient oxygen concentration is preferably 0.1% or more (e.g., 0.2% or more, 0.3% or more, 0.4% or more and the like), 0.5% or more (e.g., 0.6% or more, 0.7% or more, 0.8% or more, 0.95% or more and the like), or 1% or more (e.g., 1.1% or more, 1.2% or more, 1.3% or more, 1.4% or more and the like);

Although any method of creating a hypoxic state in a cellular environment can be used, the easiest way is to culture cells in a $CO_2$ incubator permitting adjustments of oxygen concentration, and this represents a suitable case. $CO_2$ incubators permitting adjustment of oxygen concentration are commercially available from various manufacturers (e.g., $CO_2$ incubators for hypoxic culture manufactured by Thermo scientific, Ikemoto Scientific Technology, Juji Field, Wakenyaku etc.).

The time of starting cell culture under hypoxic conditions is not particularly limited, as far as iPS cell establishment efficiency is not prevented from being improved compared with the normal oxygen concentration (20%). Although the culture may be started before the somatic cell is contacted with an iPS cell establishment efficiency improving factor of the present invention and a nuclear reprogramming substance, or at the same time as the contact, or after the contact, it is preferable, for example, that the culture under hypoxic conditions be started just after the somatic cell is contacted with the iPS cell establishment efficiency improving factor of the present invention and a nuclear reprogramming substance, or after a given time interval after the contact [e.g., 1 to 10 (e.g., 2, 3, 4, 5, 6, 7, 8 or 9) days].

The duration of cultivation of cells under hypoxic conditions is not particularly limited, as far as iPS cell establishment efficiency is not prevented from being improved compared with the normal oxygen concentration (20%); examples include, but are not limited to, periods of 3 days or more, 5 days or more, 7 days or more or 10 days or more, and 50 days or less, 40 days or less, 35 days or less or 30 days or less and the like. Preferred duration of cultivation under hypoxic conditions varies depending on ambient oxygen concentration; those skilled in the art can adjust as appropriate the duration of cultivation according to the oxygen concentration used. In an embodiment of the present invention, if iPS cell candidate colonies are selected with drug resistance as an index, it is preferable that a normal oxygen concentration be restored from hypoxic conditions before starting drug selection.

Furthermore, preferred starting time and preferred duration of cultivation for cell culture under hypoxic conditions also vary depending on the choice of nuclear reprogramming substance used, iPS cell establishment efficiency at normal oxygen concentrations and the like.

(f) Selection and Identification of iPS Cells

After being contacted with an iPS cell establishment efficiency improving factor of the present invention and a nuclear reprogramming substance (and another iPS cell establishment efficiency improver), the cell can, for example, be cultured under conditions suitable for culturing ES cells. In the case of mouse cells, the culture is carried out with the addition of leukemia inhibitory factor (LIF) as a differentiation suppression factor to an ordinary medium. Meanwhile, in the case of human cells, it is desirable that basic fibroblast growth factor (bFGF) and/or stem cell factor (SCF) be added in place of LIF. Usually, the cell is cultured in the co-presence of mouse embryonic fibroblasts (MEF) treated with radiation or an antibiotic to terminate the cell division, as feeder cells. Usually, STO cells and the like are commonly used as MEFs, but for inducing iPS cells, SNL cells [McMahon, A. P. & Bradley, A. *Cell* 62, 1073-1085 (1990)] and the like are commonly used. Co-culture with the feeder cells may be started before contact with the iPS cell establishment efficiency improving factor and nuclear reprogramming substance of the present invention, at the time of the contact, or after the contact (for example, 1-10 days later).

A candidate colony of iPS cells can be selected by a method with drug resistance and reporter activity as indicators, and also by a method based on macroscopic examination of morphology. As an example of the former, a colony positive for drug resistance and/or reporter activity is selected using a recombinant cell wherein a drug resistance gene and/or a reporter gene is targeted to the locus of a gene highly expressed specifically in pluripotent cells (for example, Fbx15, Nanog, Oct3/4 and the like, preferably Nanog or Oct3/4). As examples of such recombinant cells, a mouse-derived MEF and TTF wherein the βgeo (which encodes a fusion protein of β-galactosidase and neomycin phosphotransferase) gene is knocked-in to the Fbx15 gene locus (Takahashi & Yamanaka, *Cell,* 126, 663-676 (2006)), or a transgenic mouse-derived MEF and TTF wherein green fluorescent protein (GFP) gene and the puromycin resistance gene are integrated in the Nanog gene locus (Okita et al., *Nature,* 448, 313-317 (2007)) and the like can be mentioned. Meanwhile, methods for selecting a candidate colony by macroscopic examination of morphology include, for example, the method described by Takahashi et al. in *Cell,* 131, 861-872 (2007). Although methods using reporter cells are convenient and efficient, colony selection by macroscopic examination is desirable from the viewpoint of safety when iPS cells are prepared for the purpose of human treatment.

The identity of the cells of the selected colony as iPS cells can be confirmed by positive responses to Nanog (or Oct3/4) reporters (puromycin resistance, GFP positivity and the like), as well as by the formation of a visible ES cell-like colony, as described above; however, to increase the accuracy, it is possible to perform tests such as alkaline phosphatase staining, analyzing the expression of various ES-cell-specific genes, and transplanting the cells selected to a mouse and confirming teratoma formation.

When a nucleic acid that encodes an iPS cell establishment efficiency improving factor of the present invention is transferred to a somatic cell, the iPS cell obtained is a novel cell that is distinct from conventionally known iPS cells in that the exogenous nucleic acid is contained therein. In particular, if when the exogenous nucleic acid is transferred to the somatic cell using a retrovirus, lentivirus or the like, the exogenous nucleic acid is usually integrated in the genome of the iPS cell obtained, so that the character of containing the exogenous nucleic acid is stably retained.

(g) Use Applications for iPS Cells

The iPS cells thus established can be used for various purposes. For example, by utilizing a method of differentiation induction reported with respect to pluripotent stem cells such as ES cells (e.g., methods of differentiation induction include a method described in JP-A-2002-291469 for nerve stem cells, a method described in JP-A-2004-121165 for pancreatic stem-like cells, and a method described in JP-T-2003-505006 for hematopoietic cells; methods of differentiation induction by formation of embryoid body include a method described in JP-T-2003-523766), differentiation into various cells (e.g., myocardial cells, blood cells, nerve cells, vascular endothelial cells, insulin-secreting cells and the like) from iPS cells can be induced. Therefore, inducing iPS cells using a somatic cell collected from a patient or another person of the same or substantially the same HLA type would enable stem cell therapy by autologous transplantation, wherein the iPS cells are differentiated into desired cells (that is, cells of an affected organ of the patient, cells that have a therapeutic effect on the disease, and the like), which are transplanted to the patient. Furthermore, because functional cells (e.g., hepatocytes) differentiated from iPS cells are thought to better reflect the actual state of the functional cells in vivo than do corresponding existing cell lines, they can also be suitably used for in vitro screening for the effectiveness and toxicity of pharmaceutical candidate compounds and the like.

The present invention is hereinafter described in further detail by means of the following examples, to which, however, the invention is never limited.

EXAMPLES

Reference Example 1

Screening for Novel Reprogramming Factors

Figure 2:
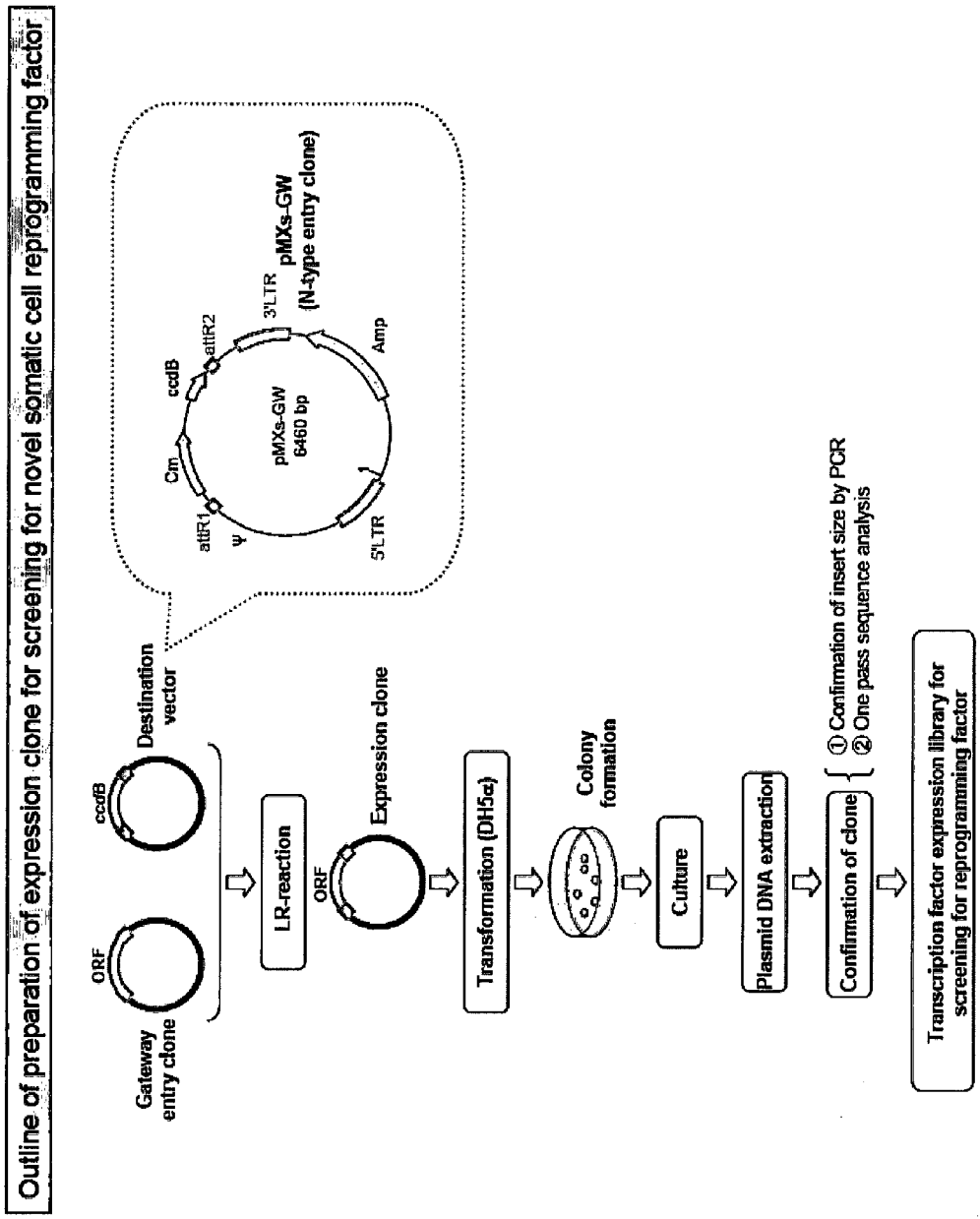
FIG. 2 outlines the procedures used to prepare a transcription factor library for screening for somatic cell reprogramming factor from an entry clone of transcription factor.

Approximately 20000 clones of comprehensive human genes were ordered on the basis of human Gateway® entry clones generated by Goshima et al. (the library described by N. Goshima et al. in *Nature methods*, 2008 was used; database published by Y. Maruyama et al. in *Nucleic Acid Res.*, 2009), by the method shown in FIG. 1. Specifically, about 50000 clones containing a full-length ORF, out of the human Gateway® entry clones, were subjected to BLASTP search against 37900 sequences (24200 genes) registered with the NCBI RefSeq, with the criteria of a coverage of 80% or more and an amino acid identity of 95% or more. A sublibrary consisting of about 20000 entry clones involving no sequence overlap in each of the N-type, which has a stop codon at the 3' end thereof, and the F-type, which lacks the stop codon, was thus constructed. These about 20000 ordered entry clones were classified by a bioinformatics technique into protein kinases, protein phosphatases, transcription factors, GPCRs, and other clones; a sublibrary consisting of entry clones of transcription factors (over 50% of all human transcription factors are covered) was constructed (FIG. 1). An expression clone DNA was prepared for each entry clone from this sublibrary of transcription factors by an LR reaction with the pMXs-GW destination vector, as shown in FIG. 2. This reaction liquor was transferred to *Escherichia coli* DH5α, which was then cloned to construct a transcription factor expression library (transcription factor expression library for reprogramming factor screening). Each of the human Oct3/4, Sox2, Klf4, c-Myc genes was also integrated into the same pMXs-GW to construct respective expression clones. A recombinant retrovirus was generated from this DNA and used in the following experiment.

An experiment to induce iPS cells was performed using dermal fibroblasts from a Nanog-GFP mouse [Okita et al., *Nature*, 448, 313-317 (2007)]. The experiment was conducted using two systems: a system involving retrovirus infection on MSTO (SNL cells treated with mitomycin C to terminate the cell division thereof) used as feeder cells [hereinafter the MSTO method, *Cell*, 126, 663-676 (2006)] and a system involving infection without using feeder cells, followed by cell reseeding and subsequent cultivation on MSTO [hereinafter the Reseed method, *Nature Biotech.*, 26, pp. 101-106 (2008)].

For 1st screening, iPS cells were induced using 24-well plates. Nanog-GFP mouse skin fibroblasts were seeded onto gelatin (Reseed method) or MSTO (MSTO method). The following day, the fibroblasts were infected with retroviruses prepared from various plasmids (Day 0). Specifically, the fibroblasts were infected with the three genes Oct3/4, Sox2 and c-Myc and one gene selected from the above-described transcription factor library in the 1:1:1:1 ratio. For negative control, the fibroblasts were infected with the three genes Oct3/4, Sox2 and c-Myc in the 1:1:1 ratio. For positive control, the fibroblasts were infected with the four genes Oct3/4, Sox2, Klf4 and c-Myc in the 1:1:1:1 ratio.

Figure 3:
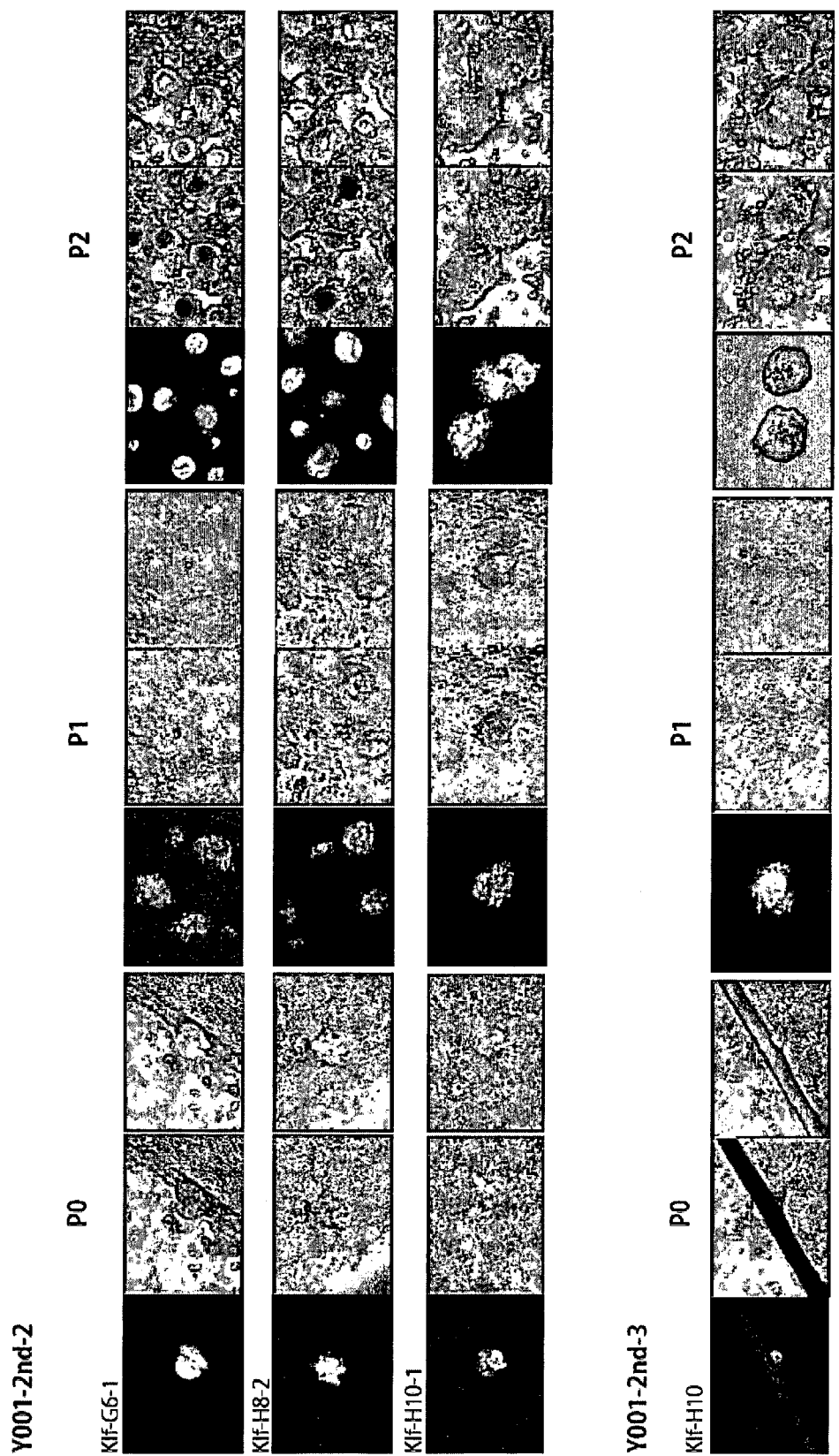
FIG. 3 is a photographic representation of the morphology of GFP-positive colonies obtained by transferring a total of 4 different genes, i.e., 3 genes (Oct3/4, Sox2, c-Myc) and G06 (gene code name: GLIS1), H08 (gene code name: DMRTB1) or H10 (gene code name: PITX2), into Nanog-GFP mouse dermal fibroblasts by means of retrovirus. "Klf-G6-1" indicates an iPS cell clone obtained by transferring G06 (gene code name: GLIS1) along with the 3 genes; "Klf-H8-2" indicates an iPS cell clone obtained by transferring H08 (gene code name: DMRTB1) along with the 3 genes; "Klf-H10-1" and "Klf-H10" indicate iPS cell clones obtained by transferring H10 (gene code name: PITX2) along with the 3 genes. P0 shows photographs taken at the time of colony establishment; P1 shows photographs for the 1st generation (24 wells); P2 shows photographs for the 2nd generation (6 wells). For each set of three photographs, the left panel shows an image of GFP-positive colonies, the central panel shows a phase-contrast image, and the right panel shows a superposed photograph of the GFP-positive colony image and the phase-contrast image. Only Klf-H10-1 was established by the Reseed method, whereas the others were established by the MSTO method.
Figure 4:
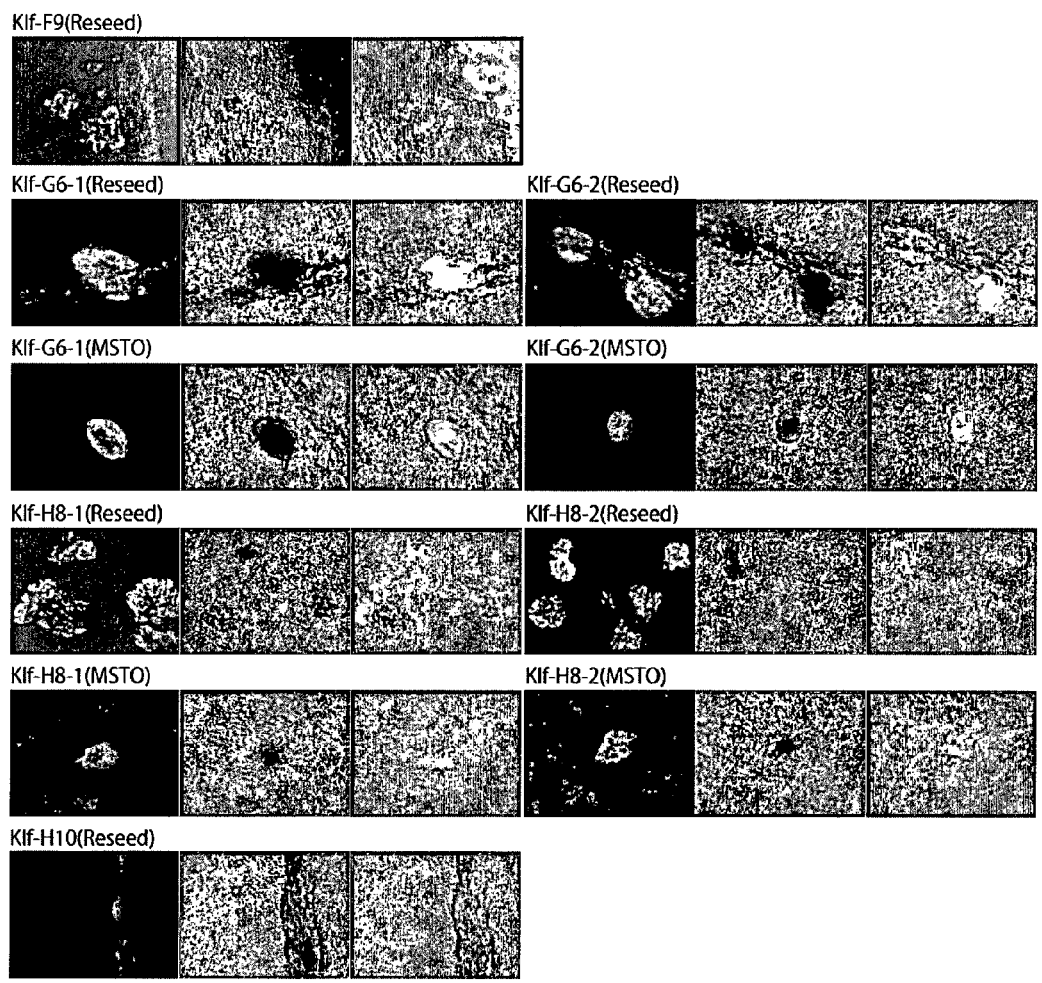
FIG. 4 is a photographic representation of the morphology of GFP-positive colonies obtained by transferring a total of 4 different genes, i.e., 3 genes (Oct3/4, Sox2, c-Myc) and F09 (gene code name: IRX6), G06 (gene code name: GLIS1), H08 (gene code name: DMRTB1) or H10 (gene code name: PITX2), into Nanog-GFP mouse dermal fibroblasts by means of retrovirus, as of the time of establishment of the colonies. "Klf-F9" indicates an iPS cell clone obtained by transferring F09 (gene code name: IRX6) along with the 3 genes; "Klf-G6-1" and "Klf-G6-2" indicate iPS cell clones obtained by transferring G06 (gene code name: GLIS1) along with the 3 genes; "Klf-H8-1" and "Klf-H8-2" indicate iPS cell clones obtained by transferring H08 (gene code name: DMRTB1) along with the 3 genes; "Klf-H10" indicates an iPS cell clone obtained by transferring H10 (gene code name: PITX2) along with the 3 genes. "Reseed" shows the results obtained by the Reseed method; "MSTO" shows the results obtained by the MSTO method.

The fibroblasts were cultured with 10% FBS/DMEM until day 2 after the infection, and with the ES medium [*Cell*, 126, 663-676 (2006)] on day 3 and after. When the fibroblasts were initially seeded onto gelatin (Reseed method), they were reseeded onto MSTO on day 3. Thereafter, while replacing the medium with a fresh supply of the same medium every two days, puromycin selection was started on day 21, and the cells were examined on day 28. As a result, GFP-positive colonies emerged in the wells incorporating each gene [sample F09 (gene code name: IRX6), sample G06 (gene code name: GLIS1), sample H08 (gene code name: DMRTB1), and sample H10 (gene code name: PITX2)] transferred along with the three genes, confirming the establishment of mouse iPS cells. When iPS induction was again attempted using 6-well plates, GFP-positive colonies emerged likewise; reproducibility was obtained. Photographic images and phase-contrast images of GFP-positive iPS cell colonies taken at the time of colony formation and 1st generation and 2nd generation are shown in FIGS. 3 and 4.

These results demonstrate the identify of these four factors as novel reprogramming factors capable of substituting for Klf4. When the same experiment was performed using MEF (mouse embryonic fibroblasts) or HDF (human dermal fibroblasts) in place of adult mouse skin fibroblasts, iPS cells (GFP-positive colonies) were likewise established.

Reference Example 2

Analysis of Established Mouse iPS Cells

Figure 5:
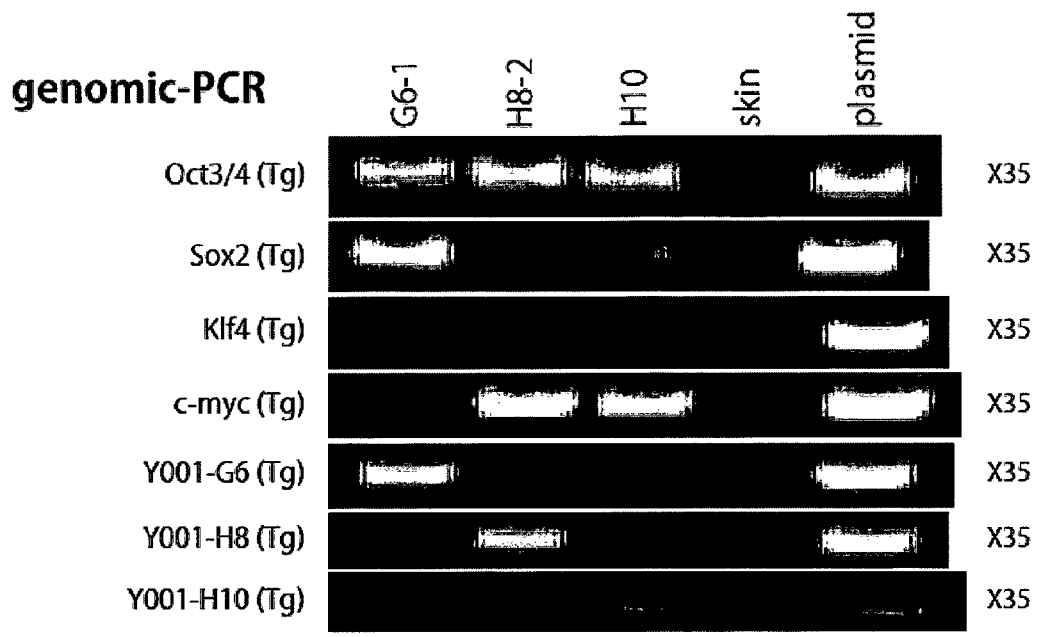
FIG. 5 is a photographic representation of the results of genomic-PCR on the G6-1 (Klf-G6-1), H8-2 (Klf-H8-2) and H10 (Klf-H10) iPS cell clones, wherein "skin" indicates the fibroblast used as a source of somatic cells, and "plasmid" indicates positive controls prepared by amplifying each gene integrated into pMXs.
Figure 6:
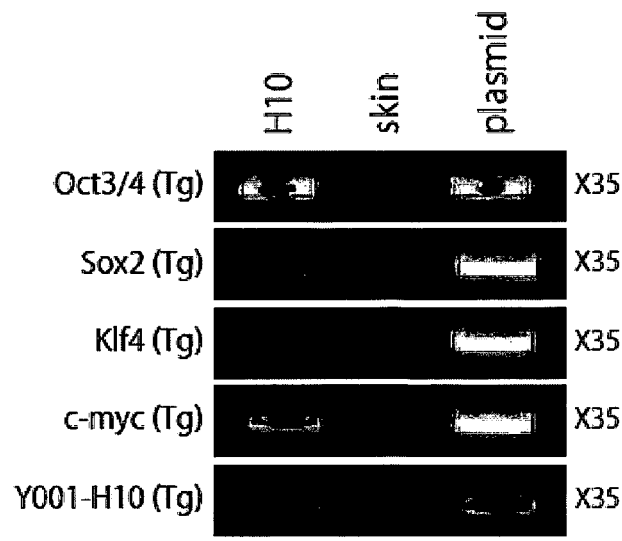
FIG. 6 is a photographic representation of the results of genomic-PCR on an H10 (Klf-H10) iPS cell clone other than that shown in FIG. 5.

The genome was extracted using the Gentra Puregene Cell Kit (QIAGEN), and Genomic-PCR was performed using a PCR enzyme (Takara Ex Taq) and the iPS cells established in Reference Example 1. The results are shown in FIGS. 5 and 6. In all the iPS cells established, the presence of only the transgenes on the genome and the absence of other genes on the genome were confirmed. For the G6-1 clone (gene code name: GLIS1), the c-Myc used for the transfer was not inserted onto the genome (FIG. 5). Because retrovirus vectors are not stably expressed unless inserted onto the genome, this clone G6-1 was thought to have been established with the expression of only the three factors Oct3/4, Sox2 and GLIS1.

Figure 7:
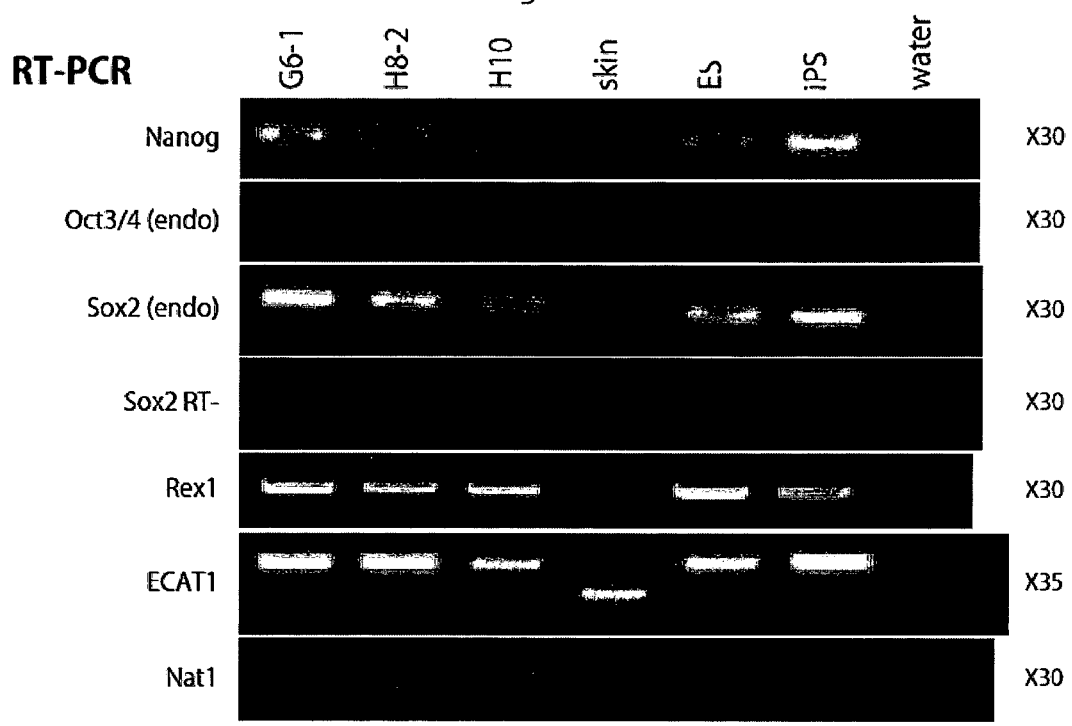
FIG. 7 is a photographic representation of the results of RT-PCR on the G6-1 (Klf-G6-1), H8-2 (Klf-H8-2) and H10 (Klf-H10) iPS cell clones, wherein "skin" indicates the fibroblast used as a source of somatic cells; "ES" and "iPS" indicate mouse ES cells and iPS cells; "Sox2 RT-" is a negative control.
Figure 8:
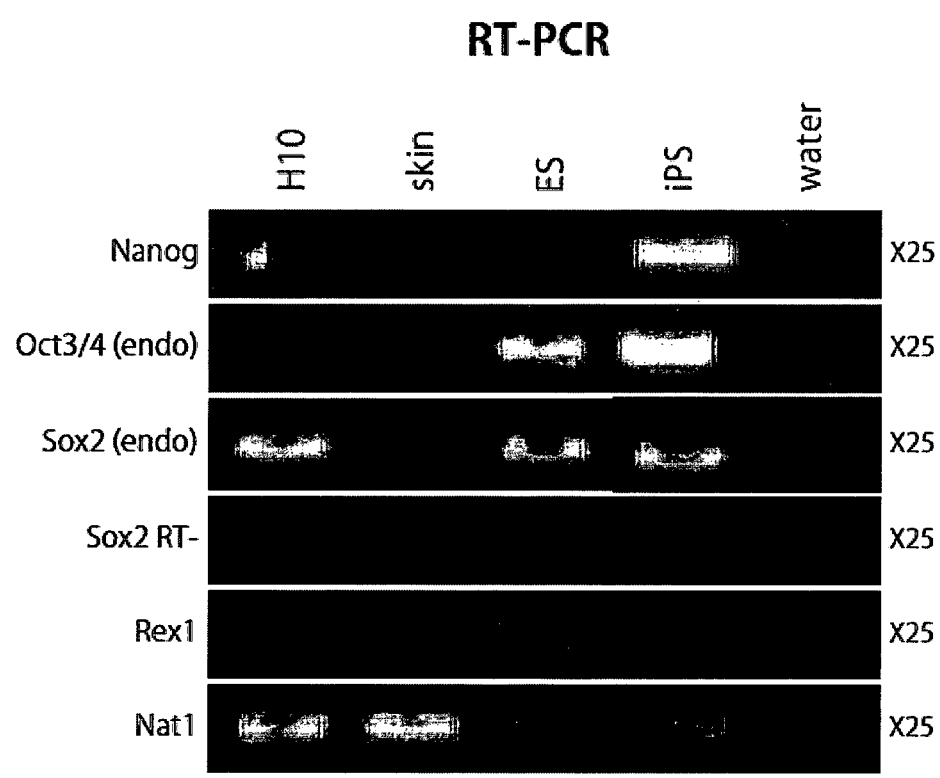
FIG. 8 is a photographic representation of the results of RT-PCR on an H10 (Klf-H10) iPS cell clone other than that in FIG. 7. In this figure, "skin" indicates the fibroblast used as a source of somatic cells; "ES" and "iPS" indicate mouse ES cells and iPS cells; "Sox2 RT-" is a negative control.

Next, RT-PCR analysis was performed using the Rever Tra Ace kit (Takara). The results are shown in FIGS. 7 and 8. All the iPS cells established in Reference Example 1 expressed the ES cell-specific marker genes Nanog, Oct3/4, Sox2, Rex1 and ECAT1. These results confirmed the identity of the cells established using the novel reprogramming factors as iPS cells.

Example 1

Establishment of Mouse iPS Cells with G6 and Klf4 Used in Combination (a) Effects of G6 and Klf4 Used in Combination on the Efficiency of Establishment of Mouse iPS cells An investigation was conducted to determine whether iPS cells could be established when using G6 (gene code name: GLIS1), H8 (gene code name: DMRTB1) and H10 (gene code name: PITX2), which are novel reprogramming factors capable of substituting for Klf4, identified in Reference Example 1, in combination with Klf4. The experiments were conducted by the Reseed method using Nanog-GFP mouse skin fibroblasts as in Reference Example 1. The combinations of genes used for the gene transfer are shown below.

Figure 9:
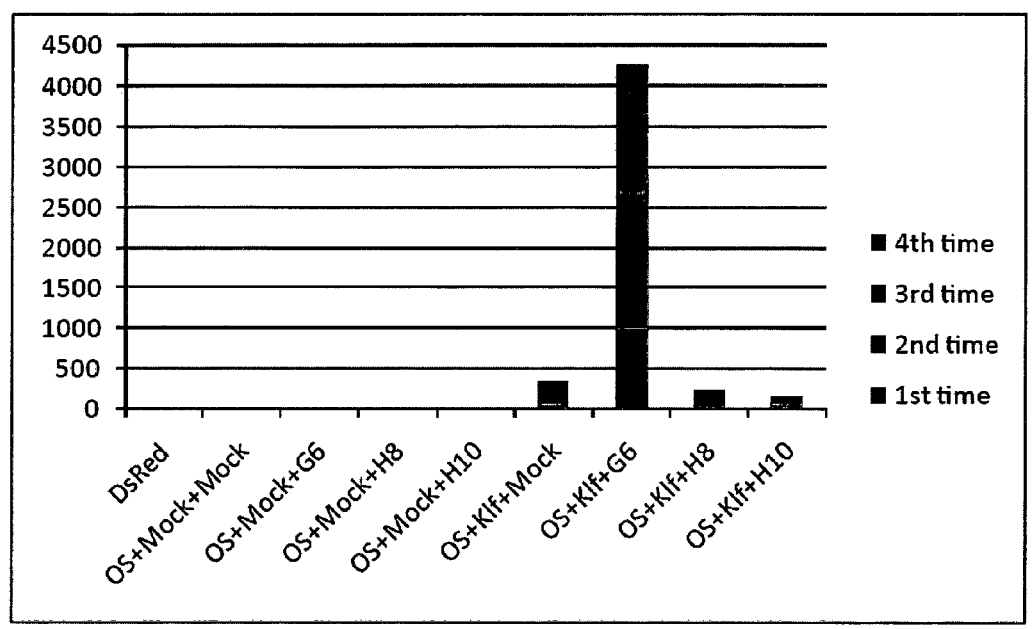
FIG. 9 is a graphic representation of the results of counting colonies of iPS cells (GFP-positive cells) established by transferring a combination of 2 factors (Oct3/4, Sox2) or 3 factors (Oct3/4, Sox2, Klf4) with G6 (GLIS1), H8 (DMRTB1) or H10 (PITX2), into Nanog-GFP mouse dermal fibroblasts. The results of three (four for the control only) independent experiments are summarized.

(1) Oct3/4, Sox2
(2) Oct3/4, Sox2, G6 (gene code name: GLIS1)
(3) Oct3/4, Sox2, H8 (gene code name: DMRTB1)
(4) Oct3/4, Sox2, H10 (gene code name: PITX2)

colonies were counted. The results of three independent experiments are shown in Table 3 and FIG. 9 (FIG. 9 is a graphic representation of the results shown in Table 3; the results of four independent experiments are shown for the control only).

TABLE 3

|  | DsRed | OS + Mock + Mock | OS + Mock + G6 | OS + Mock + H8 | OS + Mock + H10 | OS + Klf + Mock | OS + Klf + G6 | OS + Klf + H8 | OS + Klf + H10 |
|---|---|---|---|---|---|---|---|---|---|
| 1st time | 0 | 0 | 0 |   |   | 4 | 997 |   |   |
| 2nd time | 0 | 0 | 0 | 0 | 0 | 49 | 1680 | 21 | 48 |
| 3rd time | 0 | 0 | 0 | 0 | 0 | 3 | 1590 | 6 | 2 |
| 4th time | 0 | 0 |   | 6 | 0 | 295 |   | 223 | 102 |

(5) Oct3/4, Sox2, Klf4
(6) Oct3/4, Sox2, Klf4, G6
(7) Oct3/4, Sox2, Klf4, H8
(8) Oct3/4, Sox2, Klf4, H10

The retroviruses used for the reprogramming were prepared by separately transferring retrovirus expression vectors (pMXs-Oct3/4, pMXs-Sox2, pMXs-Klf4, pMXs-G6, pMXs-H8, pMXs-H10) to Plat-E cells (Morita, S. et al., Gene Ther. 7, 1063-1066) that had been seeded at $2.5 \times 10^6$ cells per 100 mm culture dish (Falcon) on the previous day. The culture broth used was DMEM/10% FCS [DMEM (Nacalai tesque) supplemented with 10% fetal bovine serum], and the cells were cultured at 37° C., 5% $CO_2$.

To facilitate vector transfer, 27 μL of FuGene6 transfection reagent (Roche) was placed in 300 μL of Opti-MEM I Reduced-Serum Medium (Invitrogen), and the mixture was allowed to stand at room temperature for 5 minutes. Subsequently, 9 μg of each expression vector was added, and the mixture was allowed to further stand at room temperature for 15 minutes, after which they were added to the Plat-E culture broth. On day 2, the Plat-E supernatant was replaced with a fresh supply of the medium. On day 3, the culture supernatant was recovered and filtered through a 0.45 μm sterile filter (Whatman), and polybrene (Nacalai) was added at 4 μg/mL to yield a viral liquid.

The Nanog-GFP mouse skin fibroblasts used were obtained by removing the dermis from a mouse back/abdomen skin, and culturing it on a gelatin-coated dish.

The culture broth used was DMEM/10% FCS, and the fibroblasts were seeded to 100 mm dishes (Falcon) at $8.0 \times 10^5$ cells per dish, and cultured at 37° C., 5% $CO_2$. The following day, each retrovirus liquid [any of the combinations (1) to (8) above] was added to transfer the genes by overnight infection.

On the day after the viral infection, the retrovirus liquid was removed and replaced with DMEM/10% FCS, and the cells were cultured using DMEM/10% FCS until day 3 after the infection. On day 3 after the infection, the medium was removed, and the cells were washed by the addition of 10 mL of PBS. After the PBS was removed, 0.25% trypsin/1 mM EDTA (Invitrogen) was added, and a reaction was allowed to proceed at 37° C. for about 5 minutes. After the cells floated up, they were suspended by the addition of an ES cell culture medium [DMEM (Nacalai Tesque) supplemented with 15% fetal bovine serum, 2 mM L-glutamine (Invitrogen), 100 μM non-essential amino acids (Invitrogen), 100 μM 2-mercaptoethanol (Invitrogen), 50 U/mL penicillin (Invitrogen) and 50 μg/mL streptomycin (Invitrogen)], and seeded to a 100 mm dish having feeder cells seeded thereto previously. The feeder cells used were SNL cells treated with mitomycin C to terminate the cell division thereof [McMahon, A. P. & Bradley, A. Cell, 62, 1073-1085 (1990)]. Cultivation was continued while replacing the ES cell culture medium with a fresh supply of the same medium every two days until a visible colony emerged; 26 to 28 days after infection, GFP-positive Even with the addition of G6, H8 or H10 to Oct3/4 and Sox2, iPS cells could not be established, or only a very few iPS cells could be established, under these conditions. When H8 or H10 was added to Oct3/4, Sox2 and Klf4, the iPS colony count did not rise, compared with the absence of the addition (Oct3/4, Sox2 and Klf4). By contrast, when G6 was added to Oct3/4, Sox2 and Klf4, the iPS colony count rose dramatically, at a level much higher than the sum of the colony count obtained with the addition of G6 to Oct3/4 and Sox2 and the colony count obtained with the addition of Klf4 to Oct3/4 and Sox2. Using Klf4 and G6 in combination was shown to be synergistically effective on the efficiency of establishment of iPS cells.

(b) Comparison of the Improving Effects of GLIS1 and c-Myc on the Establishment of Mouse iPS Cells Using Three Reprogramming Factors (OSK)

Figure 10:
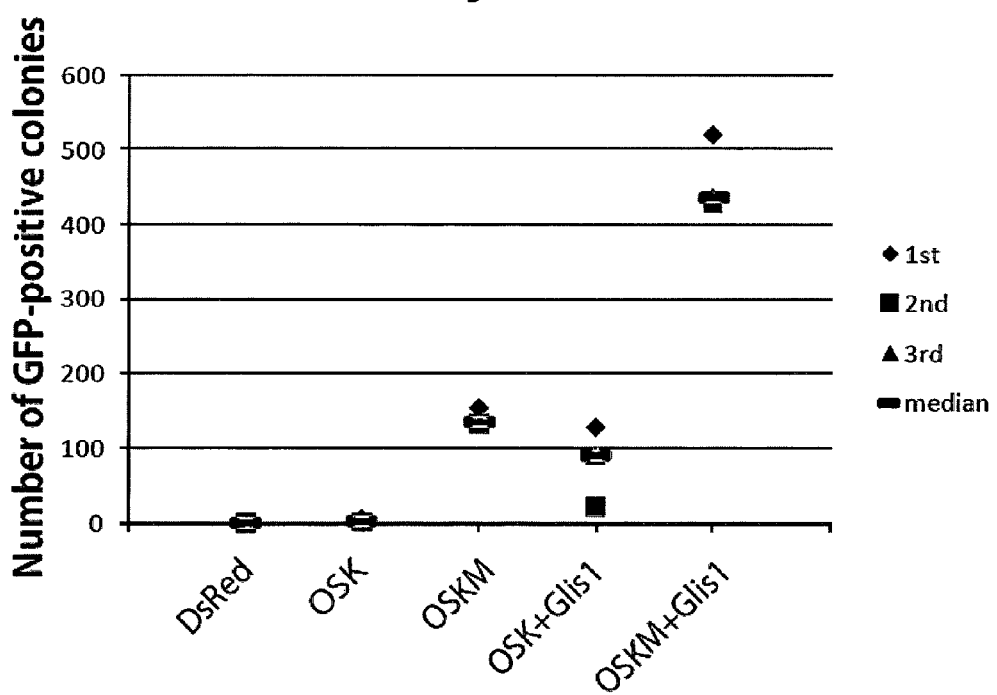
FIG. 10 shows the number of Nanog-GFP-positive colonies from indicated factor-transduced skin fibroblasts 22 days after infection.

We then compared the ability of GLIS1 and c-Myc to promote iPSC generation with OSK. In adult mouse skin fibroblasts, the effect of GLIS1 is comparable to that of c-Myc, as judged by the number of GFP-positive colonies that were formed (FIG. 10). We also observed a synergistic increase in the number of GFP-positive colonies when both GLIS1 and c-Myc were co-introduced with OSK (FIG. 10).

Figure 11:
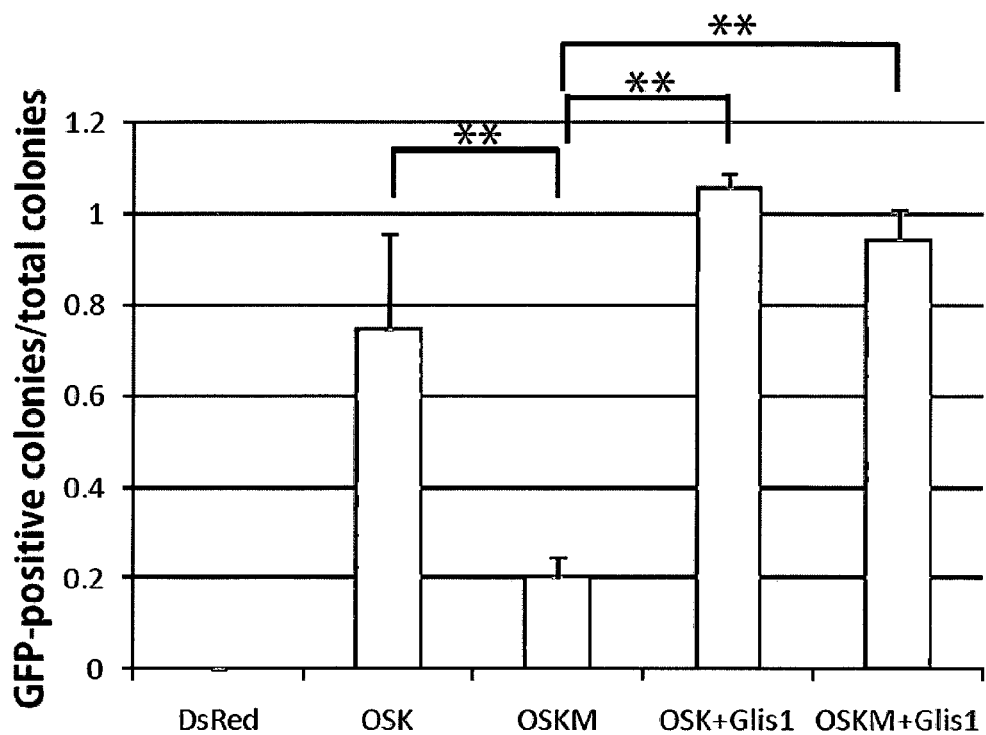
FIG. 11 shows the ratio of Nanog-GFP-positive colonies from indicated factor-transduced skin fibroblasts 22 days after infection. The graph shows the mean of three independent experiments with standard deviation (error bar). **:$p<0.01$
Figure 12:
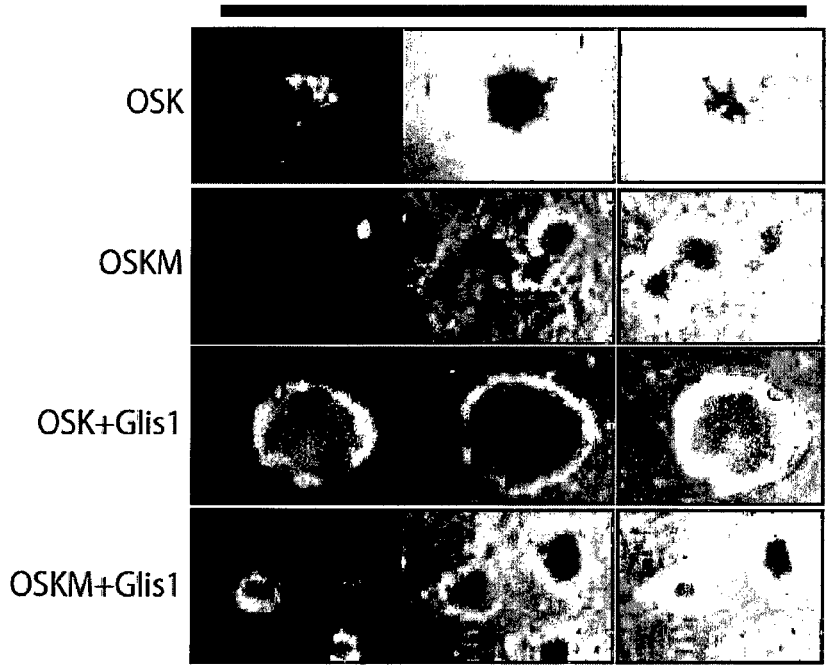
FIG. 12 shows Nanog-GFP-positive colonies from skin fibroblasts (P0; passage 0). Fluorescent images (left); Phase-contrast images (middle); Marged images (right)
Figure 13:
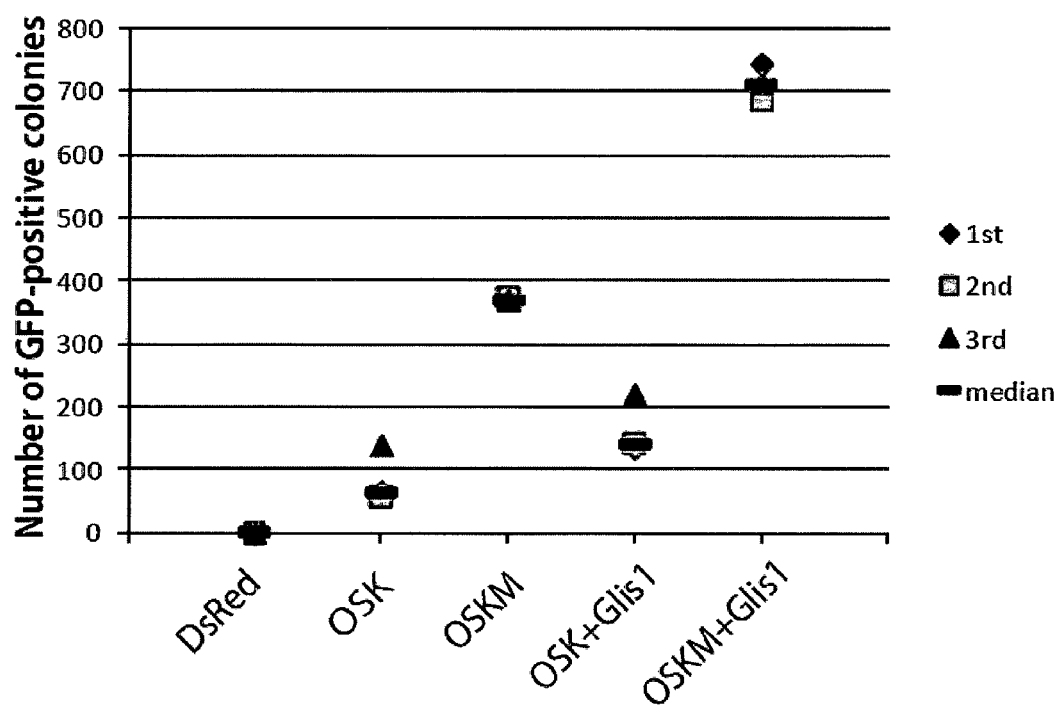
FIG. 13 shows the number of Nanog-GFP-positive colonies from the indicated factor-transduced MEFs 20 days after infection. After 3 days of infection, fibroblasts were reseeded on feeder cells.
Figure 14:
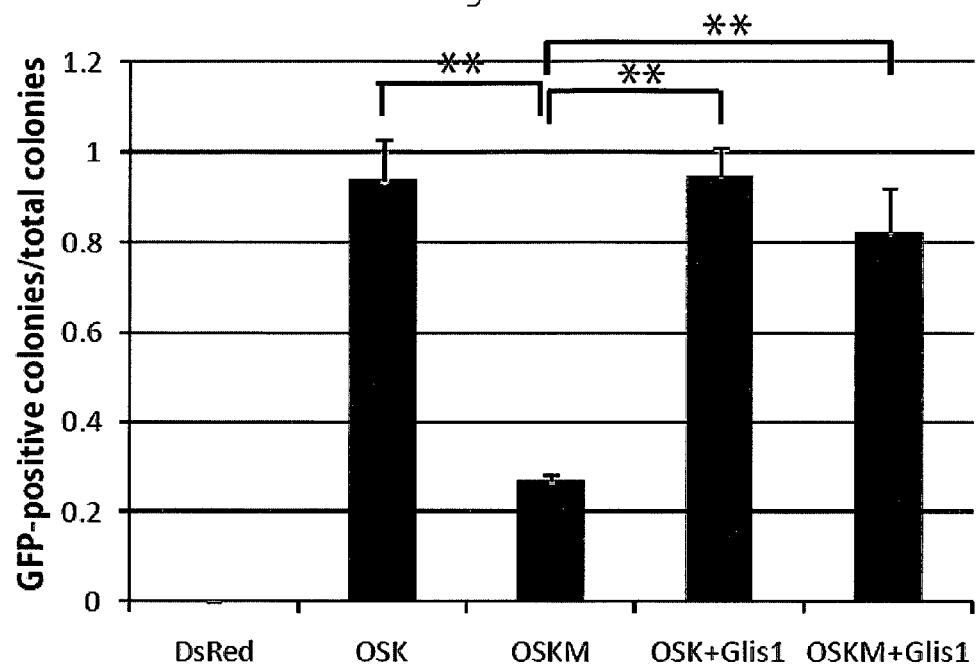
FIG. 14 shows the ratio of Nanog-GFP-positive colonies from indicated factor-transduced MEFs 20 days after infection. The graph represents the mean of three independent experiments with standard deviation (error bar). **:$p<0.01$
Figure 15:
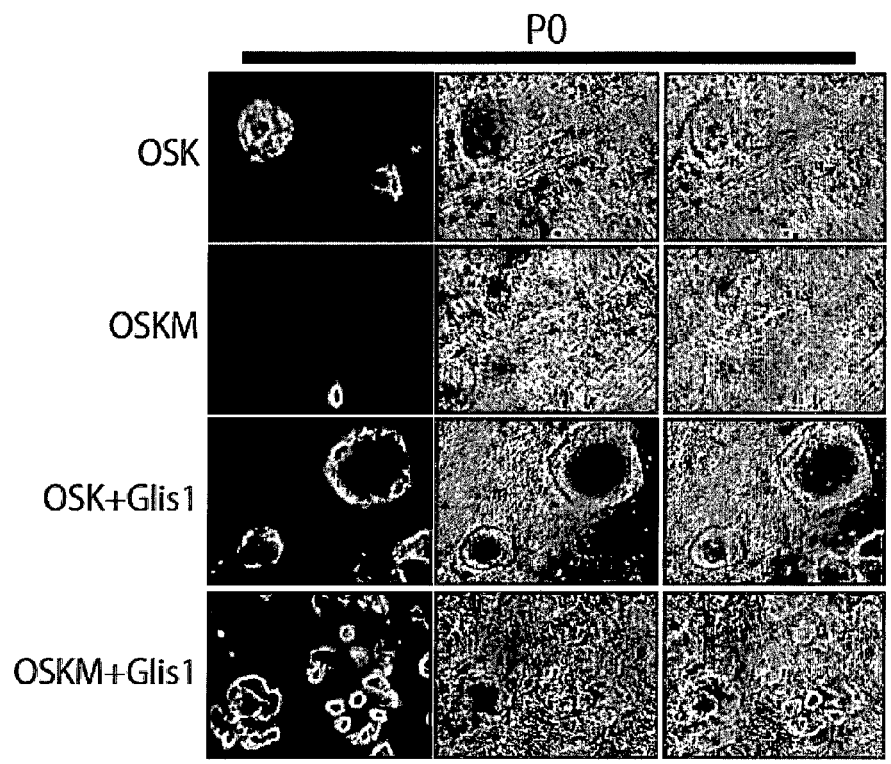
FIG. 15 shows Nanog-GFP-positive colonies from MEFs (P0; passage 0). Fluorescent images (left); Phase-contrast images (middle); Marged images (right)

We next analyzed the ratio of GFP positive colonies to total colonies that emerged after transduction. An one-way repeated-measures ANOVA test and a post-hoc Bonferroni test were used for the analyses. Differences were considered to be statistically significant for P-values of less than 0.05 (*) or 0.01 (**). The results are shown in FIG. 11. Importantly, GLIS1 specifically promoted the generation of GFP-positive colonies, but not GFP-negative colonies, which represent either partially reprogrammed cells or transformed cells (FIG. 11). In contrast, c-Myc increased the number of GFP-negative colonies more prominently than GFP-positive colonies (FIG. 11). This undesirable effect of c-Myc was counteracted when GLIS1 was co-expressed. Similar results were obtained with mouse embryonic fibroblasts (MEF) (FIG. 13 and FIG. 14). GFP-positive colonies are shown in FIG. 12 and FIG. 15.

We also confirmed the iPS cells established with OSK+GLIS1 from MEF are germline-competent.

Example 2

Establishment of Human iPS Cells with G6 and Klf4 Used in Combination (a) Effects of G6 and Klf4 Used in Combination on the Efficiency of Establishment of Human iPS Cells An investigation was conducted using adult human dermal fibroblasts (HDF) to determine whether the synergistic effect of Klf4 and G6 (GLIS1) used in combination is also noted in human cells. The combinations of genes used for the gene transfer are shown below.

(1) Oct3/4, Sox2, c-Myc
(2) Oct3/4, Sox2, c-Myc, Klf4
(3) Oct3/4, Sox2, c-Myc, G6 (gene code name: GLIS1)
(4) Oct3/4, Sox2, c-Myc, Klf4, G6

Figure 16:
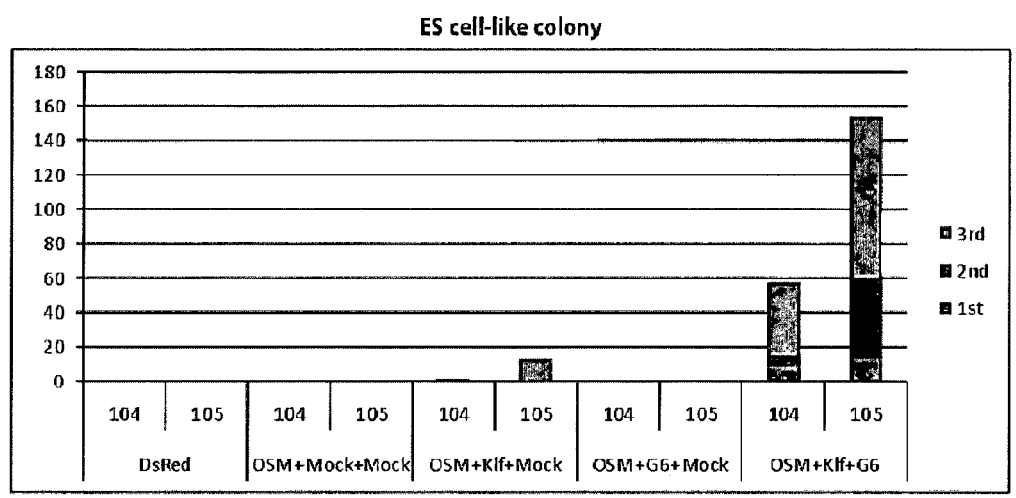
FIG. 16 is a graphic representation of the results of counting colonies of iPS cells (ES-like cells) established by transferring a combination of 3 factors (Oct3/4, Sox2, c-Myc) with Klf4 and/or G6 (GLIS1) into adult human dermal fibroblasts (HDF), wherein "104" and "105" indicate the results for $5\times10^4$ cells/100 mm dish reseeded onto feeder cells, and for $5\times10^5$ cells/100 mm dish, respectively. The results of three independent experiments are summarized.
Figure 17:
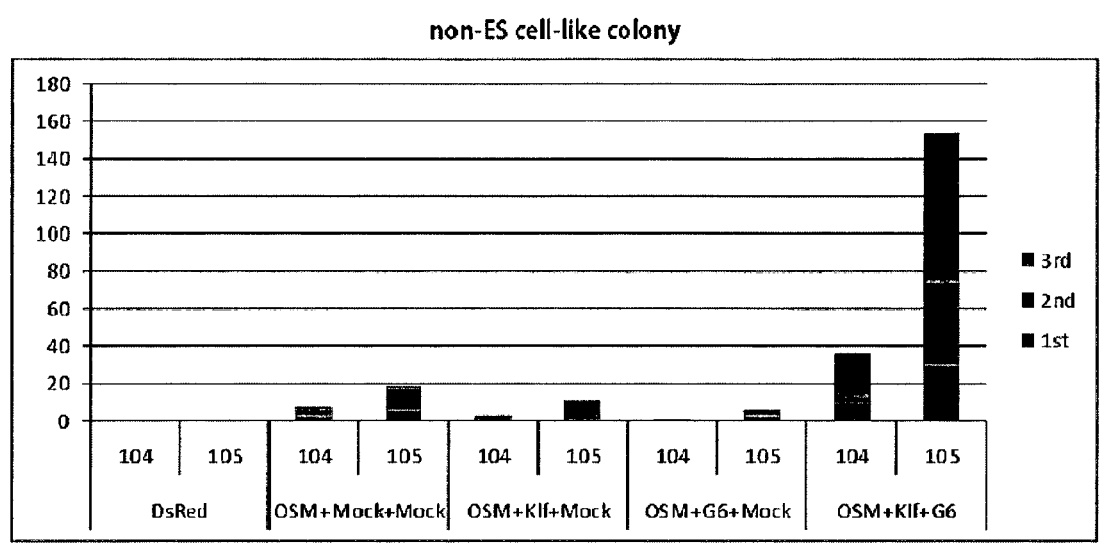
FIG. 17 is a graphic representation of the results of counting colonies of non-iPS cells (non-ES-like cells) established by transferring a combination of 3 factors (Oct3/4, Sox2, c-Myc) with Klf4 and/or G6 (GLIS1) into adult human dermal fibroblasts (HDF), wherein "104" and "105" indicate the results for $5\times10^4$ cells/100 mm dish reseeded onto feeder cells, and for $5\times10^5$ cells/100 mm dish, respectively. The results of three independent experiments are summarized.
Figure 18:
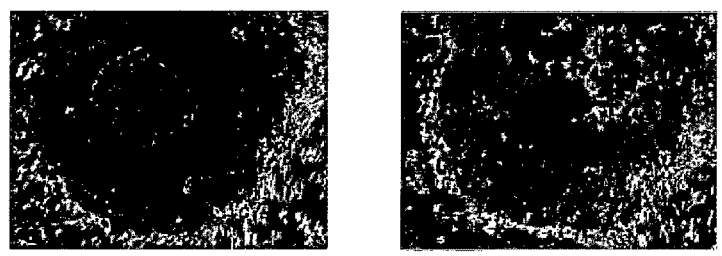
FIG. 18 is a photographic representation of phase-contrast images of iPS colonies (ES-like colonies) established with Oct3/4, Sox2, c-Myc, Klf4 and G6.

HDF was forced to express the mouse ecotropic virus receptor Slc7a1 gene using lentivirus (pLenti6/UbC-Slc7a1) as described by Takahashi, K. et al. in *Cell*, 131: 861-872 (2007). These cells (2.6×10⁵ cells/60 mm dish) were transfected with genes in the combinations (1) to (4) above using retrovirus as described by Takahashi, K. et al. in *Cell*, 131: 861-872 (2007). Six days after the viral infection, the cells were recovered and re-seeded onto feeder cells (5×10⁴ cells or 5×10⁵ cells/100 mm dish). The feeder cells used were SNL cells treated with mitomycin C to terminate the cell division thereof [McMahon, A. P. & Bradley, A. *Cell*, 62, 1073-1085 (1990)]. Starting seven days after the infection, the cells were cultured in a primate ES cell culture medium (ReproCELL) supplemented with 4 ng/mL recombinant human bFGF (WAKO). 30 to 35 days after the infection, ES cell-like colonies were counted. The results of three independent experiments are shown in FIG. 16 (ES-like colonies) and FIG. 17 (non-ES-like colonies). Phase-contrast images of iPS colonies established with Oct3/4, Sox2, c-Myc, Klf4 and G6 are shown in FIG. 18. Compared with adding Klf4 to Oct3/4, Sox2 and c-Myc and adding G6 (GLIS1) to Oct3/4, Sox2 and c-Myc, adding both Klf4 and G6 to Oct3/4, Sox2 and c-Myc resulted in the emergence of a much larger number of ES cell-like colonies (FIG. 16). These colonies exhibited an ES cell-like morphology (FIG. 18). In short, in human cells as well, a synergistic effect on the efficiency of establishment of iPS cells was noted when Klf4 and G6 were used in combination.

(b) Comparison of the Improving Effects of GLIS1 and c-Myc on the Establishment of Human iPS Cells Using Three Reprogramming Factors (OSK)

Figure 21:
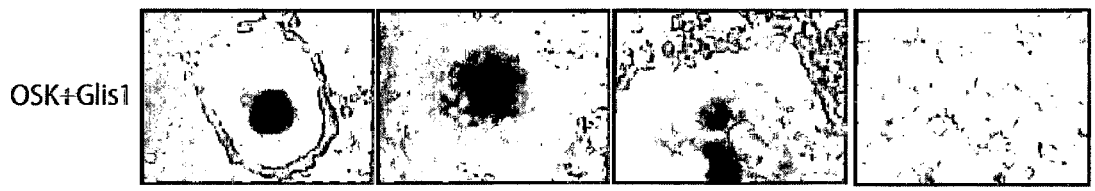
FIG. 21 shows human ESC-like colonies generated by OSK+GLIS1.

We then compared the ability of GLIS1 and c-Myc to promote iPSC generation with OSK in the same manner as described in Example 1(b). In human adult fibroblasts, GLIS1 showed a similar effect to a comparable degree to c-Myc and promoted the generation of ESC-like colonies when co-introduced with OSK (FIG. 19). Significantly, GLIS1 specifically promoted the generation of ESC-like colonies, but not non-ESC-like colonies. In contrast, c-Myc increased the number of non-ESC-like colonies more prominently than ESC-like colonies (FIG. 20). Human ESC-like colonies generated by OSK+GLIS1 are shown in FIG. 21.

Figure 22:
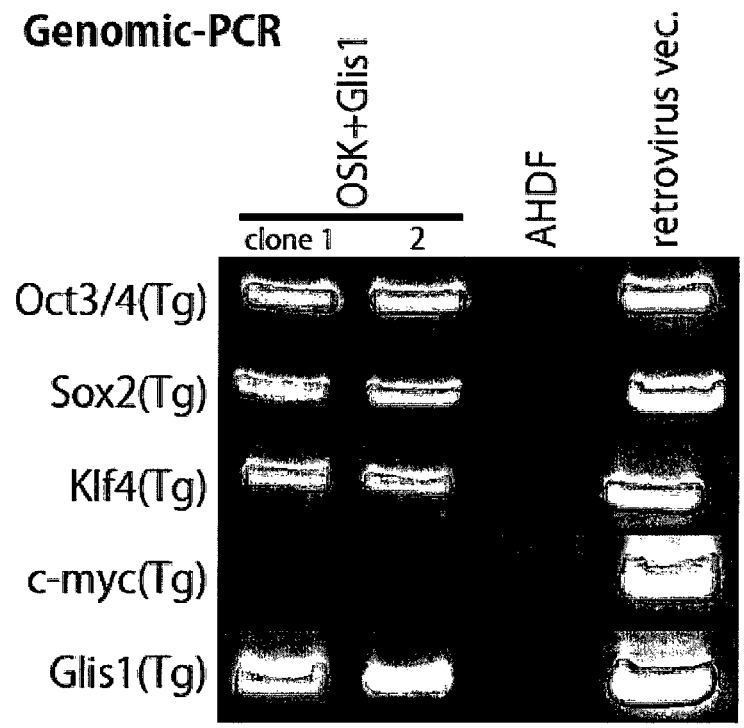
FIG. 22 shows the genomic-PCR analyses of transduced genes in established human iPS clones. AHDF: adult human dermal fibroblast
Figure 23:
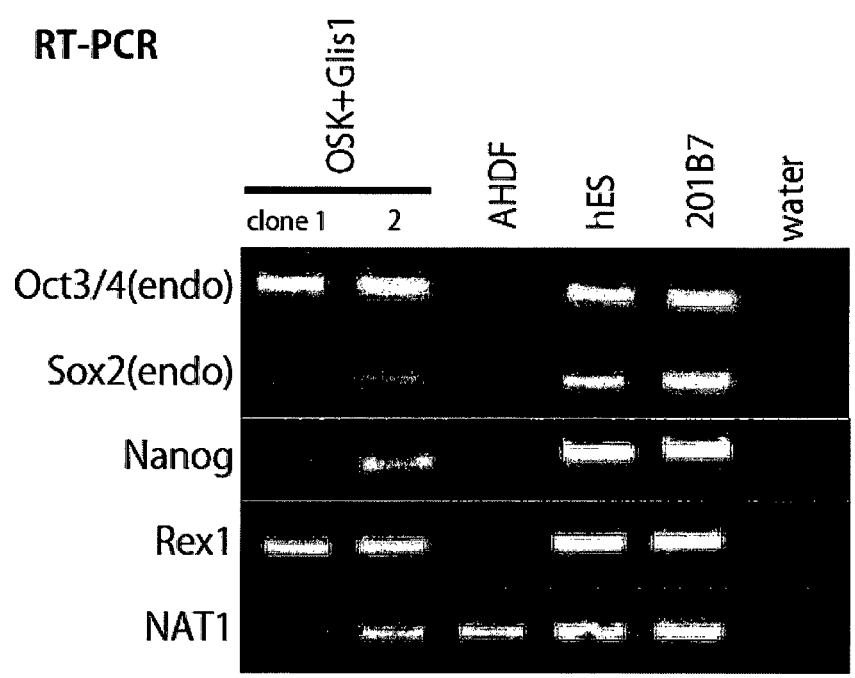
FIG. 23 shows the RT-PCR analyses of ESC-marker genes in human iPSCs generated by OSK+GLIS1. AHDF: adult human dermal fibroblast; 201B7: human iPS clone generated by OSKM
Figure 24:
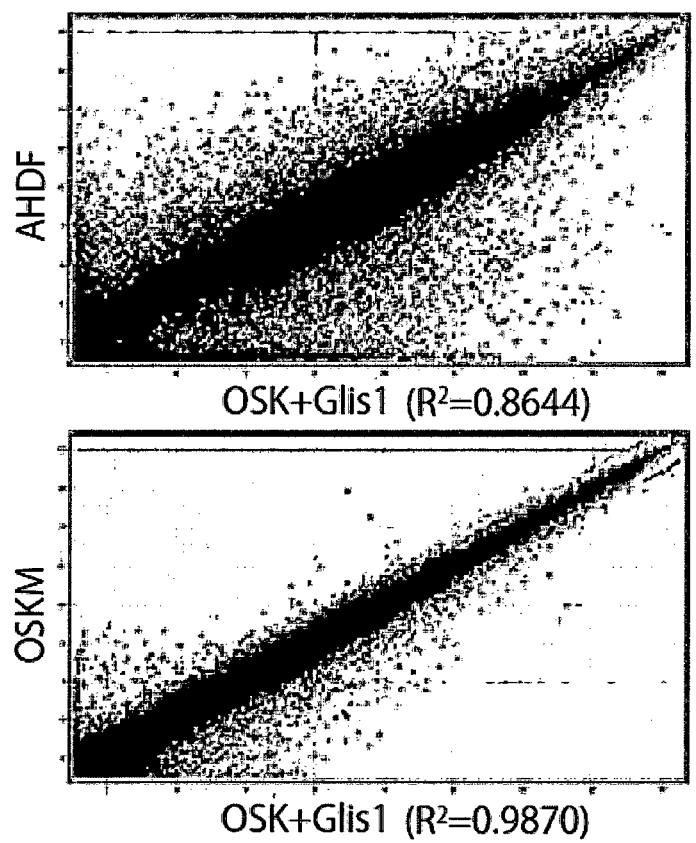
FIG. 24 shows scatter plots comparing global gene expression between iPSCs generated with OSK+GLIS1 and adult HDFs (upper), and between OSK+GLIS1-transduced iPSCs and OSKM-transduced iPSCs (lower), as determined by DNA microarray. The correlation coefficient ($R^2$) was calculated.
Figure 25:
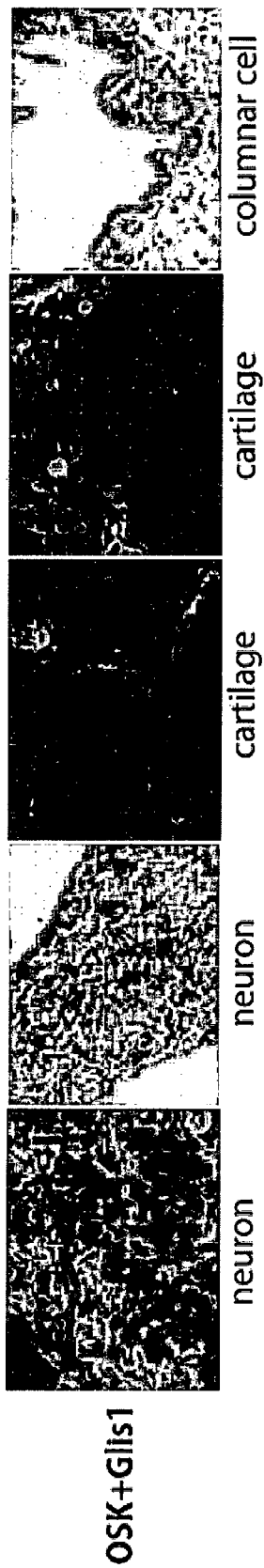
FIG. 25 shows teratoma formation of human iPSCs generated with OSK+GLIS1.

Then, genome was extracted using QIAGEN "Gentra Puregene Cell Kit", and genomic-PCR was performed using a PCR enzyme (Takara Ex Taq). The results are shown in FIG. 22. We confirmed the presence of transgenes in the established human iPSC lines (FIG. 22). RT-PCR analysis was performed using Rever Tra Ace kit (Takara). The results are shown in FIG. 23. Cells generated by OSK+GLIS1 expressed undifferentiated ESC marker genes including Oct3/4, Sox2, Nanog, and Rex1 (FIG. 23). We next performed DNA microarray analyses. Total RNAs were labelled with Cy3 and were hybridized to a Whole Human Genome Microarray (Agilent) according to the manufacturer's protocol. Arrays were scanned using the G2505C Microarray Scanner System (Agilent). Data were analysed using the GeneSpring GX11.0.1 software program (Agilent). The results are shown in FIG. 24. Cells established with OSK+GLIS1 were similar in global gene expression to iPSCs generated with OSKM (FIG. 24). We then performed teratoma formation as previously described (*Cell*, 131(5), 861-872 (2007)). Cells generated by OSK+GLIS1 produced teratomas containing various tissues of all three germ layers (FIG. 25). These results demonstrated that GLIS1 strongly and specifically promoted the generation of human iPSCs by OSK.

Example 3

Expression and Functional Analysis of GLIS1

Figure 26:
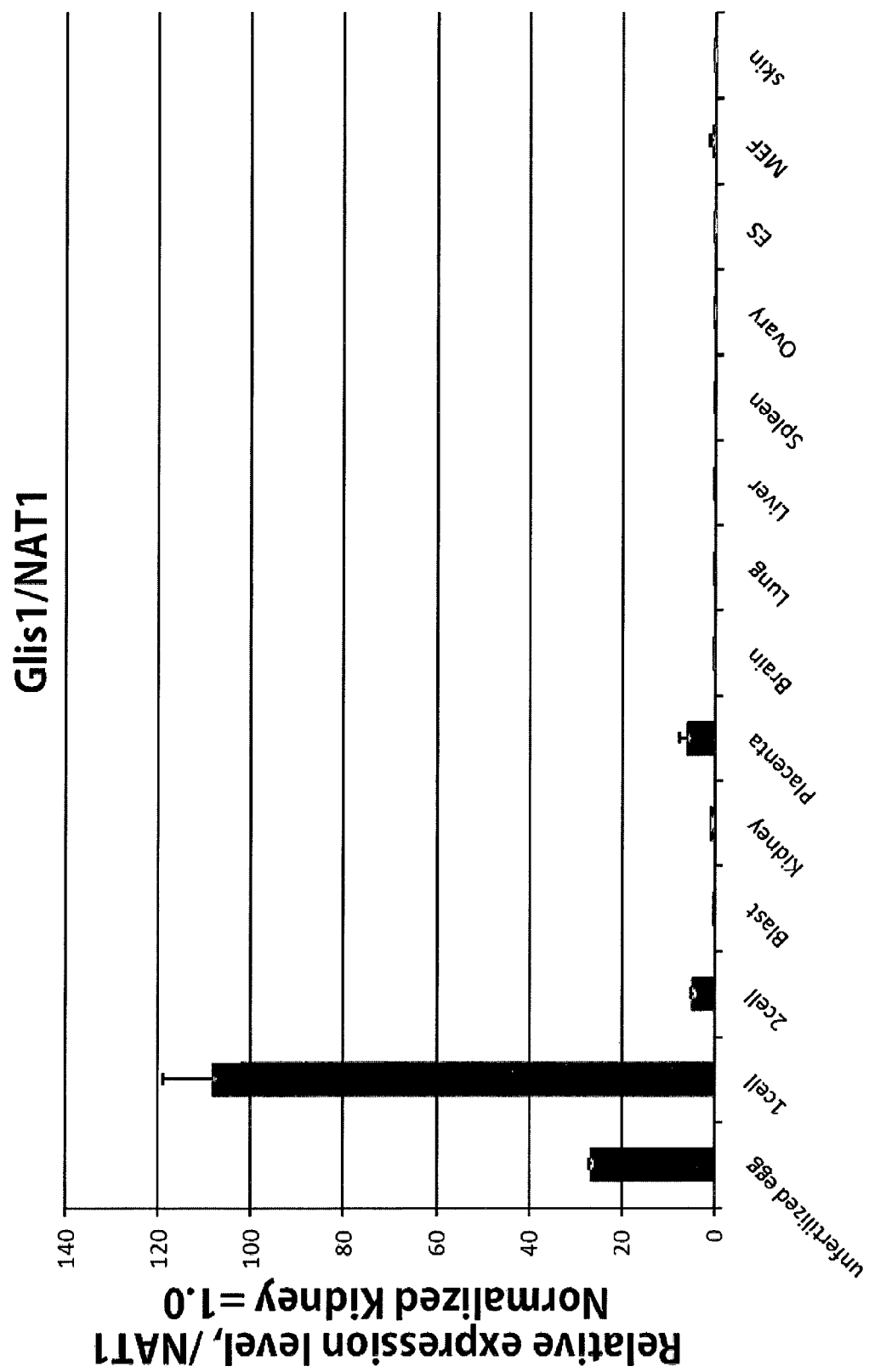
FIG. 26 shows the expression of GLIS1 in various mouse tissues. The total RNA isolated from each mouse tissue was examined by quantitative RT-PCR. The graph shows the mean of four independent experiments with standard deviation (error bar).

We then examined the expression pattern of GLIS1. The analyses of mouse expressed sequence tag (EST) databases predicted that GLIS1 representation was biased towards the zygote, especially in the fertilized ovum (http://www.ncbi.nlm.nih.gov/UniGene/ESTProfileViewer.cgi?ugli st=Mm.331757; as of Apr. 24, 2010). In addition, the Gene Expression Data provided by the MGI showed moderate GLIS1 expression in metaphase II oocytes and weak expression in the 2-cell embryo, and no expression was detected in the 8-cell to E4.5 embryos (http://www.informatics.jax.org/searches/expression.cgi?32989; as of Apr. 24, 2010). These web-based analyses strongly indicated the specific expression of GLIS1 in oocytes and one-cell embryos. To experimentally confirm these findings, we isolated total RNAs from unfertilized eggs, 1-cell embryos, 2-cell embryos, and blastocysts, as well as from several adult mouse tissues including the kidney, placenta, brain, lung, liver, spleen, and ovary. In addition, we used total RNAs isolated from mouse ESCs, MEFs, and adult skin fibroblasts. The real-time PCR analyses detected the highest expression of GLIS1 in the one-cell embryos and unfertilized eggs (FIG. 26). Modest expression levels were detected in 2-cell embryos and placental tissues (FIG. 26). Weak expression was present in several tissues including the kidney, ovary, ESCs, MEFs and skin fibroblasts (FIG. 26). These data confirmed that GLIS1 RNA is enriched in unfertilized eggs and one-cell embryos.

Figure 27:
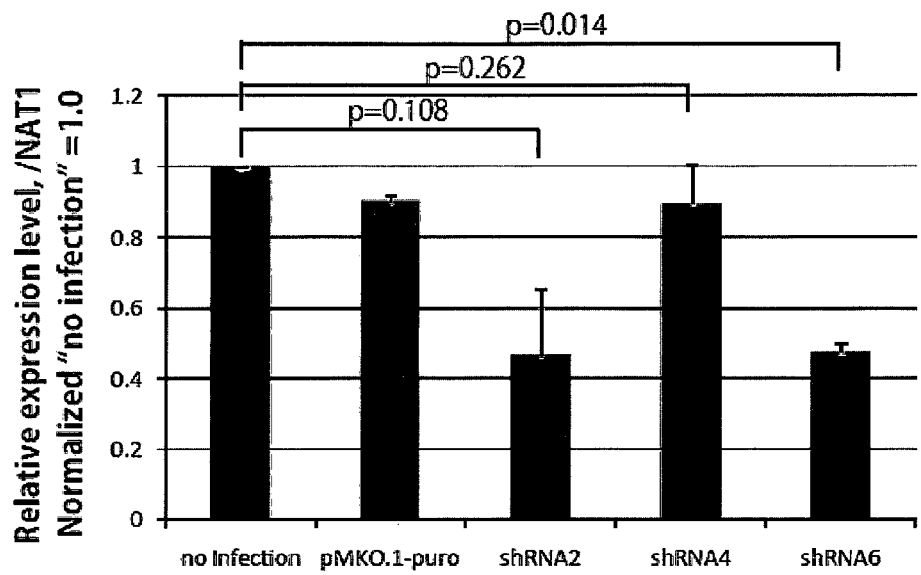
FIG. 27 shows the quantitative RT-PCR analyses of endogenous GLIS1 in skin fibroblasts exposed to GLIS1 shRNAs. The graph represents the mean of two independent experiments with average error (error bar).
Figure 28:
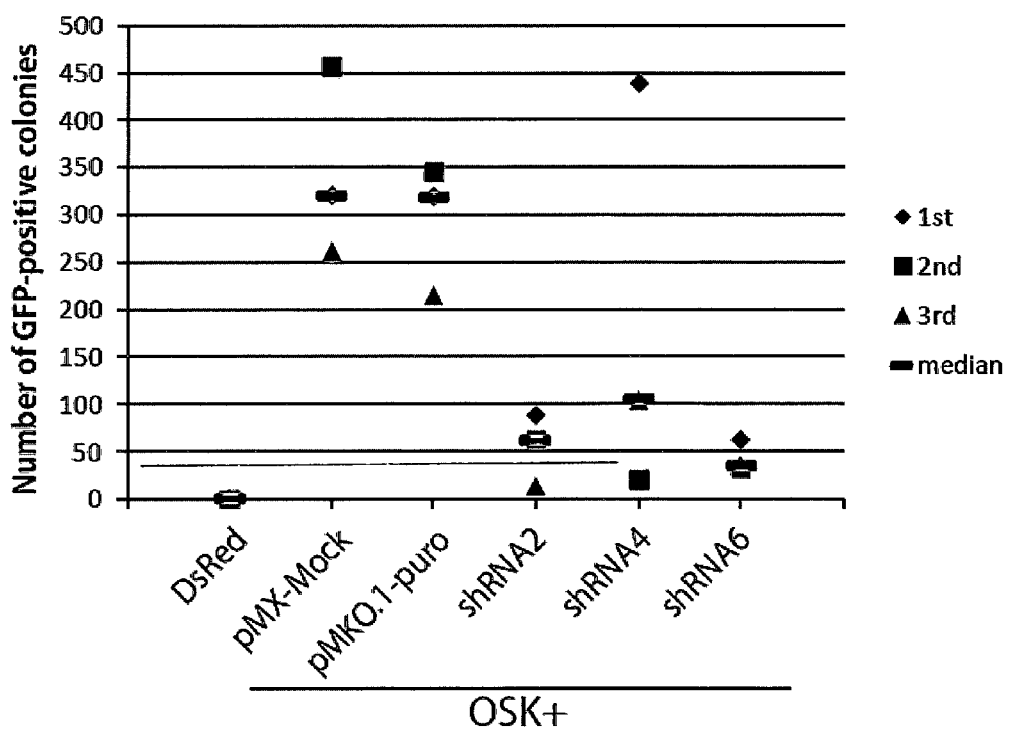
FIG. 28 shows the effect of GLIS1 shRNAs on iPSC establishment efficiency by 3 reprogramming factors (OSK). Four weeks after transduction of OSK into skin fibroblasts with or without GLIS1 shRNA, the numbers of Nanog-GFP-positive colonies were counted.

We next examined whether the endogenous GLIS1 in fibroblasts, although expressed at low levels, plays a role during iPSC generation by OSK. To this end, we constructed several retroviral vectors to express GLIS1 shRNA. The shRNA-mediated knockdown was performed as previously described (*Nature*, 460(7259), 1132-1135 (2009)). We found that shRNA2 (target sequence (positions 822-842 of SEQ ID NO:3): ggcctcaccaaccctgcacct; SEQ ID NO:13) and shRNA6 (target sequence (positions 1457-1477 of SEQ ID NO:3): gcccttcaatgcccgctacaa; SEQ ID NO:14) effectively suppressed GLIS1 when transfected into adult mouse skin fibroblasts, whereas shRNA4 (target sequence (positions 857-877 of SEQ ID NO:3): gggcaatgaacccatctcaga; SEQ ID NO:15) was less effective (FIG. 27, A paired t-test was used for the statistical analyses). We then introduced each of these shRNAs together with OSK into fibroblasts containing the Nanog-GFP reporter. We found that shRNA2 and shRNA6 significantly decreased the number of GFP-positive colonies (FIG. 28). A weaker effect was observed with shRNA4. This result suggests that the endogenous GLIS1 plays a supportive role during iPSC generation by OSK.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

In addition, the contents disclosed in any publication cited herein, including patents and patent applications, are hereby incorporated in their entireties by reference, to the extent that they have been disclosed herein.

This application is based on U.S. provisional patent applications Nos. 61/305,107 and 61/379,949, the contents of which are hereby incorporated by reference.

The invention claimed is:

1. A method of producing an iPS cell, comprising culturing a somatic cell transfected with nucleic acids that encode the following (1), (2), (3), and (4):
   (1) GLIS1,
   (2) Oct3/4,
   (3) a member of the Klf family selected from the group consisting of Klf1, Klf2, Klf4, and Klf5,
   (4) a member of the Sox family selected from the group consisting of Sox1, Sox2, Sox3, Sox15, and Sox17,
   thereby producing an iPS cell.

2. The method according to claim 1, wherein the member of the Klf family is Klf4.

3. The method according to claim 1, wherein the somatic cell has been transfected with a further nucleic acid that encodes a reprogramming substance selected from the group consisting of a member of the Myc family, a member of the Lin28 family, and Nanog,
   wherein the member of the Myc family is selected from the group consisting of c-Myc, L-Myc and N-Myc, and
   wherein the member of the Lin28 family is selected from the group consisting of Lin28 and Lin28b.

4. The method according to claim 1, wherein the member of the Sox family is Sox2.

5. The method according to claim 1, wherein the member of the Myc family is c-Myc.

6. A method of producing a somatic cell, comprising the following (1) and (2):
   (1) the step of producing an iPS cell by the method according to claim 1, and
   (2) the step of treating the iPS cell obtained through the step (1) above to induce it to differentiate into a somatic cell.

* * * * *

SEQUENCE LISTING

<160> NUMBER OF SEQ ID NOS: 15

<210> SEQ ID NO 1
<211> LENGTH: 2816
<212> TYPE: DNA
<213> ORGANISM: Homo sapiens
<220> FEATURE:
<221> NAME/KEY: CDS
<222> LOCATION: (568)..(2430)

<400> SEQUENCE: 1

```
cactgtgtac tgagactgga tgcatccttg caataaaaaa gaggttgatc acgacaaatg      60 tgaacccgc cgttataaaa acagccatca tggctgtaaa tgccaaaaag cagtcagtct      120
tgtaacttga aaaaaaaaa aaaggaattg tagattgtgc gcatggactc ggagtggggg      180
cggtggacag taagtcatga tgttttggtg gtaccacctg gttgaatttc ttcatctgaa     240
taagaagctc ctgtgatgtt ctggggaggc cttggaaggc tagcgcatcc ctcatagaaa     300
gtgaatggga gctacggaca ccgtaccccg ggctcagaga agagcctgct ggacctggac     360
cttgctgagg gccctggccc cacctgctgc cagggcctgt ttctccctgc aggaagccca     420
ccgccccggg ctcacccca agcttgtgag aggctgctgc atttccccca ccctgacagg     480
tcacctagac cccaggccac gtatgtgaac ggcagcctcc caaccacaca acacatcaaa     540
caggagtcct tgcccgacta ccaagcc atg gca gag gcc cgc aca tcc ctg tct    594
                                Met Ala Glu Ala Arg Thr Ser Leu Ser
                                  1               5 gcc cac tgt cgg ggc ccg ctg gcc act ggc ctg cac cca gac ctg gac      642
Ala His Cys Arg Gly Pro Leu Ala Thr Gly Leu His Pro Asp Leu Asp
 10                  15                  20                  25 ctc ccg ggc cga agc ctc gcc acc cct gcg cct tcc tgc tac ctt ctg      690
Leu Pro Gly Arg Ser Leu Ala Thr Pro Ala Pro Ser Cys Tyr Leu Leu
                 30                  35                  40 ggc agc gaa ccc agc tct ggc ctg ggc ctc cag ccc gag acc cac ctc      738
Gly Ser Glu Pro Ser Ser Gly Leu Gly Leu Gln Pro Glu Thr His Leu
             45                  50                  55 ccc gag ggc agc ctg aag cgg tgc tgc gtc ttg ggc cta ccc ccc acc      786
Pro Glu Gly Ser Leu Lys Arg Cys Cys Val Leu Gly Leu Pro Pro Thr
         60                  65                  70 tcc cca gcc tcc tcc tca ccc tgt gcc tcc tcc gac gtc acc tcc atc      834
Ser Pro Ala Ser Ser Ser Pro Cys Ala Ser Ser Asp Val Thr Ser Ile
     75                  80                  85 atc cgc tcc tcc cag acg tct ctg gtc acc tgt gta aat gga ctc cgg      882
Ile Arg Ser Ser Gln Thr Ser Leu Val Thr Cys Val Asn Gly Leu Arg
 90                  95                 100                 105 agc ccc cct ctg acg gga gat ctg ggg ggc cct tcc aag cgg gcc cgg      930
Ser Pro Pro Leu Thr Gly Asp Leu Gly Gly Pro Ser Lys Arg Ala Arg
                110                 115                 120 cct ggc cct gca tcg acg gac agc cat gag ggc agc ttg caa ctt gaa      978
Pro Gly Pro Ala Ser Thr Asp Ser His Glu Gly Ser Leu Gln Leu Glu
            125                 130                 135 gcc tgc cgg aag gcg agc ttc ctg aag cag gaa ccc gcg gat gag ttt     1026
Ala Cys Arg Lys Ala Ser Phe Leu Lys Gln Glu Pro Ala Asp Glu Phe
        140                 145                 150 tca gag ctc ttt ggg cct cac cag cag ggc ctg ccg ccc ccc tat ccc     1074
Ser Glu Leu Phe Gly Pro His Gln Gln Gly Leu Pro Pro Pro Tyr Pro
    155                 160                 165 ctg tct cag ttg ccg cct ggc cca agc ctt gga ggc ctg ggg ctg ggc     1122
Leu Ser Gln Leu Pro Pro Gly Pro Ser Leu Gly Gly Leu Gly Leu Gly
170                 175                 180                 185
```

-continued

| | |
|---|---|
| ctg gca ggc agg gtg gtg gcc ggg cgg cag gcg tgc cgc tgg gtg gac<br>Leu Ala Gly Arg Val Val Ala Gly Arg Gln Ala Cys Arg Trp Val Asp<br>190                   195                    200 | 1170 |
| tgc tgt gca gcc tat gag cag cag gag gag ctg gtg cgg cac atc gag<br>Cys Cys Ala Ala Tyr Glu Gln Gln Glu Glu Leu Val Arg His Ile Glu<br>205                   210                   215 | 1218 |
| aag agc cac atc gac cag cgc aag ggc gag gac ttc acc tgc ttc tgg<br>Lys Ser His Ile Asp Gln Arg Lys Gly Glu Asp Phe Thr Cys Phe Trp<br>220                   225                   230 | 1266 |
| gct ggc tgc gtg cgc cgc tac aag ccc ttc aac gcc cgc tac aag ctg<br>Ala Gly Cys Val Arg Arg Tyr Lys Pro Phe Asn Ala Arg Tyr Lys Leu<br>235                   240                   245 | 1314 |
| ctc atc cac atg cga gtg cac tcg ggc gag aag ccc aac aag tgc atg<br>Leu Ile His Met Arg Val His Ser Gly Glu Lys Pro Asn Lys Cys Met<br>250                   255                   260                   265 | 1362 |
| ttt gaa ggc tgc agc aag gcc ttc tca cgg ctg gag aac ctc aag atc<br>Phe Glu Gly Cys Ser Lys Ala Phe Ser Arg Leu Glu Asn Leu Lys Ile<br>270                   275                   280 | 1410 |
| cac ctg agg agc cac acg ggc gag aag ccg tac ctg tgc cag cac ccg<br>His Leu Arg Ser His Thr Gly Glu Lys Pro Tyr Leu Cys Gln His Pro<br>285                   290                   295 | 1458 |
| ggt tgc cag aag gcc ttc agc aac tcc agc gac cgc gcc aag cac cag<br>Gly Cys Gln Lys Ala Phe Ser Asn Ser Ser Asp Arg Ala Lys His Gln<br>300                   305                   310 | 1506 |
| cgc acc cac cta gac acg aag ccg tac gcc tgt cag atc cct ggc tgc<br>Arg Thr His Leu Asp Thr Lys Pro Tyr Ala Cys Gln Ile Pro Gly Cys<br>315                   320                   325 | 1554 |
| tcc aag cgc tac aca gac ccc agc tcc ctc cgc aag cac gtc aag gcc<br>Ser Lys Arg Tyr Thr Asp Pro Ser Ser Leu Arg Lys His Val Lys Ala<br>330                   335                   340                   345 | 1602 |
| cat tca gcc aaa gag cag cag gtg cgt aag aag ctg cat gcg ggc cct<br>His Ser Ala Lys Glu Gln Gln Val Arg Lys Lys Leu His Ala Gly Pro<br>350                   355                   360 | 1650 |
| gac acc gag gcc gac gtc ctg acc gag tgt ctg gtc ctg cag cag ctc<br>Asp Thr Glu Ala Asp Val Leu Thr Glu Cys Leu Val Leu Gln Gln Leu<br>365                   370                   375 | 1698 |
| cac acg tcc aca cag ctg gct gcc agc gac ggc aag ggt ggt tgt ggc<br>His Thr Ser Thr Gln Leu Ala Ala Ser Asp Gly Lys Gly Gly Cys Gly<br>380                   385                   390 | 1746 |
| ctg ggc cag gag ctg ctc cca ggt gtg tat cct ggc tcc atc acc ccc<br>Leu Gly Gln Glu Leu Leu Pro Gly Val Tyr Pro Gly Ser Ile Thr Pro<br>395                   400                   405 | 1794 |
| cat aac gga ctt gca tcg ggc ctc ctg ccc cca gcg cac gac gta cct<br>His Asn Gly Leu Ala Ser Gly Leu Leu Pro Pro Ala His Asp Val Pro<br>410                   415                   420                   425 | 1842 |
| tcc agg cac cac ccg ctg gat gcc acc acc agt cca cac cat ctg<br>Ser Arg His His Pro Leu Asp Ala Thr Thr Ser Ser His His His Leu<br>430                   435                   440 | 1890 |
| tcc cct ctg ccc atg gct gag agc acc cgg gat ggg ttg ggg ccc ggc<br>Ser Pro Leu Pro Met Ala Glu Ser Thr Arg Asp Gly Leu Gly Pro Gly<br>445                   450                   455 | 1938 |
| ctc ctc tca cca ata gtc agc ccc ctg aag ggg ctg ggg cca ccg ccg<br>Leu Leu Ser Pro Ile Val Ser Pro Leu Lys Gly Leu Gly Pro Pro Pro<br>460                   465                   470 | 1986 |
| ctg ccc cca tcc tct cag agc cat tct ccg ggg ggc cag ccc ttc ccc<br>Leu Pro Pro Ser Ser Gln Ser His Ser Pro Gly Gly Gln Pro Phe Pro<br>475                   480                   485 | 2034 |
| aca ctc ccc agc aag ccg tcc tac cca ccc ttc cag agc cct cca ccc<br>Thr Leu Pro Ser Lys Pro Ser Tyr Pro Pro Phe Gln Ser Pro Pro Pro<br>490                   495                   500                   505 | 2082 |

```
ccg cct ctg ccc agc cca caa ggt tac cag ggc agt ttc cac tcc atc      2130
Pro Pro Leu Pro Ser Pro Gln Gly Tyr Gln Gly Ser Phe His Ser Ile
            510                 515                 520 cag agt tgc ttc ccc tat ggc gac tgc tac cgg atg gct gaa cca gca      2178
Gln Ser Cys Phe Pro Tyr Gly Asp Cys Tyr Arg Met Ala Glu Pro Ala
            525                 530                 535 gcc ggt ggg gac gga ctg gtc ggg gag acc cac ggt ttc aac ccc ctg      2226
Ala Gly Gly Asp Gly Leu Val Gly Glu Thr His Gly Phe Asn Pro Leu
            540                 545                 550 cgg ccc aat ggc tac cac agc ctc agc acg ccc ttg cct gcc aca ggc      2274
Arg Pro Asn Gly Tyr His Ser Leu Ser Thr Pro Leu Pro Ala Thr Gly
            555                 560                 565 tat gag gcc ctg gct gag gcc tca tgc ccc aca gcg ctg cca cag cag      2322
Tyr Glu Ala Leu Ala Glu Ala Ser Cys Pro Thr Ala Leu Pro Gln Gln
570                 575                 580                 585 cca tct gaa gat gtg gtg tcc agc ggc ccc gag gac tgt ggc ttc ttc      2370
Pro Ser Glu Asp Val Val Ser Ser Gly Pro Glu Asp Cys Gly Phe Phe
                590                 595                 600 ccc aat gga gcc ttt gac cac tgc ctg ggc cac atc ccc tcc atc tac      2418
Pro Asn Gly Ala Phe Asp His Cys Leu Gly His Ile Pro Ser Ile Tyr
                605                 610                 615 aca gac acc tga aggagccccc acatgcgcct gcccatccag cactgcagat          2470
Thr Asp Thr
        620 gccacctcgc ccacctgctg tcgctcccac cctccgtgca cctagcagga gtgccaggcc    2530 acagccggaa cagccaggcc atgacccagg ggagccagcg ctgccacccc acccagcgct    2590 gccagggagc cgccatccga gcttgagctg ggcgcacaga ggtgcccgcc aggatctgtg    2650 gccctgtaac attccctcga tcttgtcttc ccgttcctcc ccgcagtggt tttgaaatca    2710 cagacctcgt gtatataaaa tatgcagaac ttgttttccg ttcccctgcc agttttatat    2770 ttttggtttt acaagaaaaa acattaaaaa ctggaaagga gatgtg                   2816

<210> SEQ ID NO 2
<211> LENGTH: 620
<212> TYPE: PRT
<213> ORGANISM: Homo sapiens

<400> SEQUENCE: 2

Met Ala Glu Ala Arg Thr Ser Leu Ser Ala His Cys Arg Gly Pro Leu
1               5                   10                  15

Ala Thr Gly Leu His Pro Asp Leu Asp Leu Pro Gly Arg Ser Leu Ala
            20                  25                  30

Thr Pro Ala Pro Ser Cys Tyr Leu Leu Gly Ser Glu Pro Ser Ser Gly
        35                  40                  45

Leu Gly Leu Gln Pro Glu Thr His Leu Pro Glu Gly Ser Leu Lys Arg
    50                  55                  60

Cys Cys Val Leu Gly Leu Pro Pro Thr Ser Pro Ala Ser Ser Ser Pro
65                  70                  75                  80

Cys Ala Ser Ser Asp Val Thr Ser Ile Ile Arg Ser Ser Gln Thr Ser
                85                  90                  95

Leu Val Thr Cys Val Asn Gly Leu Arg Ser Pro Leu Thr Gly Asp
            100                 105                 110

Leu Gly Gly Pro Ser Lys Arg Ala Arg Pro Gly Pro Ala Ser Thr Asp
        115                 120                 125

Ser His Glu Gly Ser Leu Gln Leu Glu Ala Cys Arg Lys Ala Ser Phe
    130                 135                 140
```

```
Leu Lys Gln Glu Pro Ala Asp Glu Phe Ser Glu Leu Phe Gly Pro His
145                 150                 155                 160

Gln Gln Gly Leu Pro Pro Tyr Pro Leu Ser Gln Leu Pro Pro Gly
            165                 170                 175

Pro Ser Leu Gly Gly Leu Gly Leu Gly Leu Ala Gly Arg Val Val Ala
                180                 185                 190

Gly Arg Gln Ala Cys Arg Trp Val Asp Cys Cys Ala Ala Tyr Glu Gln
        195                 200                 205

Gln Glu Glu Leu Val Arg His Ile Glu Lys Ser His Ile Asp Gln Arg
        210                 215                 220

Lys Gly Glu Asp Phe Thr Cys Phe Trp Ala Gly Cys Val Arg Arg Tyr
225                 230                 235                 240

Lys Pro Phe Asn Ala Arg Tyr Lys Leu Leu Ile His Met Arg Val His
                245                 250                 255

Ser Gly Glu Lys Pro Asn Lys Cys Met Phe Glu Gly Cys Ser Lys Ala
                260                 265                 270

Phe Ser Arg Leu Glu Asn Leu Lys Ile His Leu Arg Ser His Thr Gly
        275                 280                 285

Glu Lys Pro Tyr Leu Cys Gln His Pro Gly Cys Gln Lys Ala Phe Ser
290                 295                 300

Asn Ser Ser Asp Arg Ala Lys His Gln Arg Thr His Leu Asp Thr Lys
305                 310                 315                 320

Pro Tyr Ala Cys Gln Ile Pro Gly Cys Ser Lys Arg Tyr Thr Asp Pro
                325                 330                 335

Ser Ser Leu Arg Lys His Val Lys Ala His Ser Ala Lys Glu Gln Gln
            340                 345                 350

Val Arg Lys Lys Leu His Ala Gly Pro Asp Thr Glu Ala Asp Val Leu
            355                 360                 365

Thr Glu Cys Leu Val Leu Gln Gln Leu His Thr Ser Thr Gln Leu Ala
    370                 375                 380

Ala Ser Asp Gly Lys Gly Gly Cys Gly Leu Gly Gln Glu Leu Leu Pro
385                 390                 395                 400

Gly Val Tyr Pro Gly Ser Ile Thr Pro His Asn Gly Leu Ala Ser Gly
                405                 410                 415

Leu Leu Pro Pro Ala His Asp Val Pro Ser Arg His His Pro Leu Asp
            420                 425                 430

Ala Thr Thr Ser Ser His His His Leu Ser Pro Leu Pro Met Ala Glu
        435                 440                 445

Ser Thr Arg Asp Gly Leu Gly Pro Gly Leu Leu Ser Pro Ile Val Ser
    450                 455                 460

Pro Leu Lys Gly Leu Gly Pro Pro Leu Pro Pro Ser Ser Gln Ser
465                 470                 475                 480

His Ser Pro Gly Gly Gln Pro Phe Pro Thr Leu Pro Ser Lys Pro Ser
                485                 490                 495

Tyr Pro Pro Phe Gln Ser Pro Pro Pro Leu Pro Ser Pro Gln
                500                 505                 510

Gly Tyr Gln Gly Ser Phe His Ser Ile Gln Ser Cys Phe Pro Tyr Gly
            515                 520                 525

Asp Cys Tyr Arg Met Ala Glu Pro Ala Ala Gly Gly Asp Gly Leu Val
        530                 535                 540

Gly Glu Thr His Gly Phe Asn Pro Leu Arg Pro Asn Gly Tyr His Ser
545                 550                 555                 560
```

```
Leu Ser Thr Pro Leu Pro Ala Thr Gly Tyr Glu Ala Leu Ala Glu Ala
                565                 570                 575

Ser Cys Pro Thr Ala Leu Pro Gln Gln Pro Ser Glu Asp Val Val Ser
            580                 585                 590

Ser Gly Pro Glu Asp Cys Gly Phe Phe Pro Asn Gly Ala Phe Asp His
        595                 600                 605

Cys Leu Gly His Ile Pro Ser Ile Tyr Thr Asp Thr
610                 615                 620

<210> SEQ ID NO 3
<211> LENGTH: 2904
<212> TYPE: DNA
<213> ORGANISM: Mus musculus
<220> FEATURE:
<221> NAME/KEY: CDS
<222> LOCATION: (222)..(2591)

<400> SEQUENCE: 3
ggggacccag tggcgtccga atccgggagc tctggggtgg cgcggggctc gccgaggggc      60
gaggcgaatt tgggggccct gaggcctcgc tctcgcggga atgatgctgg aaatgatgct     120
gaggctccgg cgtgagactt gcggctgccg gcggagcgga gtgtgagccg gtgaatgggg     180
agcctggcgc gaccccagc cgtgcgcccc gccccggcgc c atg cat tgc gag gtg      236
                                             Met His Cys Glu Val
                                               1               5 gcc gag gca ctt tcg gac aag agg cca aag gag gcc cct ggt gct cct       284
Ala Glu Ala Leu Ser Asp Lys Arg Pro Lys Glu Ala Pro Gly Ala Pro
             10                  15                  20 ggc cag ggc cgc ggg cct gtc agc ctg gga gcg cac atg gcc ttc agg       332
Gly Gln Gly Arg Gly Pro Val Ser Leu Gly Ala His Met Ala Phe Arg
         25                  30                  35 att gct gtg agt ggt ggc ggc tgc ggg gac ggg aac ccg cta gac ctg       380
Ile Ala Val Ser Gly Gly Gly Cys Gly Asp Gly Asn Pro Leu Asp Leu
     40                  45                  50 ctg cct cgg cta ccg gtg cca cca cca cgt gcc cac gat ctc ctt cgg       428
Leu Pro Arg Leu Pro Val Pro Pro Pro Arg Ala His Asp Leu Leu Arg
 55                  60                  65 ccc cgg agc cct cga gac tat ggt gtg tcc aag acc ggc agc ggg aag       476
Pro Arg Ser Pro Arg Asp Tyr Gly Val Ser Lys Thr Gly Ser Gly Lys
70                  75                  80                  85 gtg aac ggg agc tac ggg cac agc tca gag aag agc ctg ctg gac ctg       524
Val Asn Gly Ser Tyr Gly His Ser Ser Glu Lys Ser Leu Leu Asp Leu
                 90                  95                 100 gac ctg gcc gag ggt ccc agc ccc tcc tgc cac cag ggt ctg ttt ctt       572
Asp Leu Ala Glu Gly Pro Ser Pro Ser Cys His Gln Gly Leu Phe Leu
            105                 110                 115 cct gca ggg acc cca cca ccc cgg ggt cac ccc cct gtc tgt gag aag       620
Pro Ala Gly Thr Pro Pro Pro Arg Gly His Pro Pro Val Cys Glu Lys
        120                 125                 130 ctg ctg cac ttc ccc cac cca aac agg tca ccc aga cct cag gct acg       668
Leu Leu His Phe Pro His Pro Asn Arg Ser Pro Arg Pro Gln Ala Thr
    135                 140                 145 ttt gtg aac ggc agc ctc cca gcc gct cag cac atc aag caa gaa gcc       716
Phe Val Asn Gly Ser Leu Pro Ala Ala Gln His Ile Lys Gln Glu Ala
150                 155                 160                 165 cta ccg gac tac cag gcc atg gtc agc gcc cac aca ccc ctg ccc acc       764
Leu Pro Asp Tyr Gln Ala Met Val Ser Ala His Thr Pro Leu Pro Thr
                170                 175                 180 cac tgc cga gcc cca tcg tcc atg ggt ctg ccc tca gac ctg gac ttt       812
His Cys Arg Ala Pro Ser Ser Met Gly Leu Pro Ser Asp Leu Asp Phe
```

-continued

|     |     |     | 185 |     |     |     | 190 |     |     |     | 195 |     |     |     |      |
| --- | --- | --- | --- | --- | --- | --- | --- | --- | --- | --- | --- | --- | --- | --- | ---- |
| cca | gac | cga | ggc | ctc | acc | aac | cct | gca | cct | tcc | tgc | tac | ctt | ctg | ggc  | 860
| Pro | Asp | Arg | Gly | Leu | Thr | Asn | Pro | Ala | Pro | Ser | Cys | Tyr | Leu | Leu | Gly  |
|     |     | 200 |     |     |     |     | 205 |     |     |     |     | 210 |     |     |      |

| aat | gaa | ccc | atc | tca | gac | ctg | ggt | ccc | caa | ccc | gag | gcc | cac | ctc | ccc  | 908
| Asn | Glu | Pro | Ile | Ser | Asp | Leu | Gly | Pro | Gln | Pro | Glu | Ala | His | Leu | Pro  |
|     | 215 |     |     |     |     | 220 |     |     |     |     | 225 |     |     |     |      |

| gag | ggc | agc | ctg | aaa | cgc | tgc | tgc | ctc | ctg | ggc | ctg | ccc | ccc | acc | tct  | 956
| Glu | Gly | Ser | Leu | Lys | Arg | Cys | Cys | Leu | Leu | Gly | Leu | Pro | Pro | Thr | Ser  |
| 230 |     |     |     |     | 235 |     |     |     |     | 240 |     |     |     |     | 245  |

| tca | gcc | tcc | tcc | tca | ccc | tgt | gcc | tcc | tca | gat | atc | aat | cct | gtc | atc  | 1004
| Ser | Ala | Ser | Ser | Ser | Pro | Cys | Ala | Ser | Ser | Asp | Ile | Asn | Pro | Val | Ile  |
|     |     |     |     | 250 |     |     |     |     | 255 |     |     |     |     | 260 |      |

| cac | tcc | tcc | cag | aca | gct | cta | gtt | agc | tgt | gta | aat | gga | ctc | cga | agc  | 1052
| His | Ser | Ser | Gln | Thr | Ala | Leu | Val | Ser | Cys | Val | Asn | Gly | Leu | Arg | Ser  |
|     |     |     | 265 |     |     |     |     | 270 |     |     |     |     | 275 |     |      |

| cca | cct | ctg | ccg | gga | gac | ctg | ggg | ggc | cct | ccc | aag | cgg | tca | cgg | ccc  | 1100
| Pro | Pro | Leu | Pro | Gly | Asp | Leu | Gly | Gly | Pro | Pro | Lys | Arg | Ser | Arg | Pro  |
|     |     | 280 |     |     |     |     | 285 |     |     |     |     | 290 |     |     |      |

| ggg | cct | gca | tcc | agt | gac | ggc | cag | gag | ggc | agc | ttg | cag | ctt | gaa | gca  | 1148
| Gly | Pro | Ala | Ser | Ser | Asp | Gly | Gln | Glu | Gly | Ser | Leu | Gln | Leu | Glu | Ala  |
|     | 295 |     |     |     |     | 300 |     |     |     |     | 305 |     |     |     |      |

| tgc | cgg | aag | tca | ggc | ttc | ctg | aag | cag | gag | ccc | atg | gac | gag | ttt | tca  | 1196
| Cys | Arg | Lys | Ser | Gly | Phe | Leu | Lys | Gln | Glu | Pro | Met | Asp | Glu | Phe | Ser  |
| 310 |     |     |     |     | 315 |     |     |     |     | 320 |     |     |     |     | 325  |

| gag | ctt | ttt | gct | cca | cac | cac | cag | ggt | ttg | cca | ccc | cct | tac | ccc | ttg  | 1244
| Glu | Leu | Phe | Ala | Pro | His | His | Gln | Gly | Leu | Pro | Pro | Pro | Tyr | Pro | Leu  |
|     |     |     |     | 330 |     |     |     |     | 335 |     |     |     |     | 340 |      |

| cct | cag | ttg | cca | act | ggc | ccc | ggc | ctc | gga | ggc | cta | ggg | ctg | ggc | ctg  | 1292
| Pro | Gln | Leu | Pro | Thr | Gly | Pro | Gly | Leu | Gly | Gly | Leu | Gly | Leu | Gly | Leu  |
|     |     |     | 345 |     |     |     |     | 350 |     |     |     |     | 355 |     |      |

| gca | ggt | agg | atg | gtt | gcc | ggt | cgg | cag | gca | tgc | cgc | tgg | gtg | gac | tgc  | 1340
| Ala | Gly | Arg | Met | Val | Ala | Gly | Arg | Gln | Ala | Cys | Arg | Trp | Val | Asp | Cys  |
|     |     | 360 |     |     |     |     | 365 |     |     |     |     | 370 |     |     |      |

| tgc | gca | gcc | tac | gag | cag | cag | gag | gag | ctg | gtg | cgg | cac | atc | gag | aag  | 1388
| Cys | Ala | Ala | Tyr | Glu | Gln | Gln | Glu | Glu | Leu | Val | Arg | His | Ile | Glu | Lys  |
|     | 375 |     |     |     |     | 380 |     |     |     |     | 385 |     |     |     |      |

| agc | cac | atc | gac | cag | cgc | aag | ggc | gaa | gac | ttc | acc | tgc | ttc | tgg | gcc  | 1436
| Ser | His | Ile | Asp | Gln | Arg | Lys | Gly | Glu | Asp | Phe | Thr | Cys | Phe | Trp | Ala  |
| 390 |     |     |     |     | 395 |     |     |     |     | 400 |     |     |     |     | 405  |

| ggg | tgt | gtg | cgg | cgc | tac | aag | ccc | ttc | aat | gcc | cgc | tac | aag | ctg | ctc  | 1484
| Gly | Cys | Val | Arg | Arg | Tyr | Lys | Pro | Phe | Asn | Ala | Arg | Tyr | Lys | Leu | Leu  |
|     |     |     |     | 410 |     |     |     |     | 415 |     |     |     |     | 420 |      |

| atc | cac | atg | agg | gta | cac | tca | ggc | gag | aag | ccc | aac | aag | tgc | atg | ttc  | 1532
| Ile | His | Met | Arg | Val | His | Ser | Gly | Glu | Lys | Pro | Asn | Lys | Cys | Met | Phe  |
|     |     |     | 425 |     |     |     |     | 430 |     |     |     |     | 435 |     |      |

| gaa | ggc | tgc | agt | aaa | gcc | ttt | tcc | cgt | ctg | gag | aac | ctg | aag | atc | cat  | 1580
| Glu | Gly | Cys | Ser | Lys | Ala | Phe | Ser | Arg | Leu | Glu | Asn | Leu | Lys | Ile | His  |
|     |     | 440 |     |     |     |     | 445 |     |     |     |     | 450 |     |     |      |

| ctg | cgg | agc | cac | aca | ggc | gag | aaa | cca | tac | ctg | tgc | cag | cac | cca | ggc  | 1628
| Leu | Arg | Ser | His | Thr | Gly | Glu | Lys | Pro | Tyr | Leu | Cys | Gln | His | Pro | Gly  |
|     | 455 |     |     |     |     | 460 |     |     |     |     | 465 |     |     |     |      |

| tgc | cag | aag | gcc | ttc | agc | aac | tcc | agc | gac | cgt | gcc | aag | cac | caa | cgc  | 1676
| Cys | Gln | Lys | Ala | Phe | Ser | Asn | Ser | Ser | Asp | Arg | Ala | Lys | His | Gln | Arg  |
| 470 |     |     |     |     | 475 |     |     |     |     | 480 |     |     |     |     | 485  |

| acc | cac | ctc | gac | acg | aag | cca | tat | gct | tgt | cag | atc | cct | ggc | tgc | tcc  | 1724
| Thr | His | Leu | Asp | Thr | Lys | Pro | Tyr | Ala | Cys | Gln | Ile | Pro | Gly | Cys | Ser  |
|     |     |     |     | 490 |     |     |     |     | 495 |     |     |     |     | 500 |      |

| aag | cgc | tac | acg | gac | ccc | agc | tcc | ctc | cgc | aag | cac | gtg | aag | gcc | cac  | 1772

```
                    -continued

Lys Arg Tyr Thr Asp Pro Ser Ser Leu Arg Lys His Val Lys Ala His
            505                 510                 515 tca gcc aaa gag cag cag gtg cgt aag aag ctg cac aca ggt gcc gac    1820
Ser Ala Lys Glu Gln Gln Val Arg Lys Lys Leu His Thr Gly Ala Asp
        520                 525                 530 cca gag gct gat gtt ctg tcc gag tgt ctg tcc ctg cag cag ctc caa    1868
Pro Glu Ala Asp Val Leu Ser Glu Cys Leu Ser Leu Gln Gln Leu Gln
535                 540                 545 gca tcc aca ctg ttg ccg gcc agc aga ggg aag ggc agc caa acc ctg    1916
Ala Ser Thr Leu Leu Pro Ala Ser Arg Gly Lys Gly Ser Gln Thr Leu
550                 555                 560                 565 agc cag gag ctc ctc cca ggt gtg tat cct ggc tcc gtc acc cca caa    1964
Ser Gln Glu Leu Leu Pro Gly Val Tyr Pro Gly Ser Val Thr Pro Gln
            570                 575                 580 aac ggg ctt gct tca ggc atc ctg tcc ccc tcc cac gat gtc cct tcc    2012
Asn Gly Leu Ala Ser Gly Ile Leu Ser Pro Ser His Asp Val Pro Ser
        585                 590                 595 agg cac cac cca ctg gag gtc ccc act ggt tcc cac cac cac ctg tcc    2060
Arg His His Pro Leu Glu Val Pro Thr Gly Ser His His His Leu Ser
    600                 605                 610 cct ctg ccc aca gct gag agc acc agg gat ggc ctg ggg ccc agt ctc    2108
Pro Leu Pro Thr Ala Glu Ser Thr Arg Asp Gly Leu Gly Pro Ser Leu
615                 620                 625 ctt tca ccc atg gtc agc cca ctg aag ggg ctt ggt ccc cca ccg cta    2156
Leu Ser Pro Met Val Ser Pro Leu Lys Gly Leu Gly Pro Pro Pro Leu
630                 635                 640                 645 cca cca gcc tcc cag agt cag tct cca ggg gga cag tca ttc tct aca    2204
Pro Pro Ala Ser Gln Ser Gln Ser Pro Gly Gly Gln Ser Phe Ser Thr
            650                 655                 660 gtc ccc agc aag cct acc tac cca tcc ttc caa agc cca cca cct ctg    2252
Val Pro Ser Lys Pro Thr Tyr Pro Ser Phe Gln Ser Pro Pro Pro Leu
        665                 670                 675 ccc agc ccc caa ggc tac caa ggc agt ttc cat tcc atc cag aac tgc    2300
Pro Ser Pro Gln Gly Tyr Gln Gly Ser Phe His Ser Ile Gln Asn Cys
    680                 685                 690 ttc ccc tac gct gac tgc tac cgg gcc act gag cca gca gcc tcc agg    2348
Phe Pro Tyr Ala Asp Cys Tyr Arg Ala Thr Glu Pro Ala Ala Ser Arg
695                 700                 705 gat gga ctg gtg ggt gat gcc cac ggt ttc aac ccc ttg cga ccc agc    2396
Asp Gly Leu Val Gly Asp Ala His Gly Phe Asn Pro Leu Arg Pro Ser
710                 715                 720                 725 aca tac tcc agc ctc agc aca cct tta tcc gca cca ggc tac gag acc    2444
Thr Tyr Ser Ser Leu Ser Thr Pro Leu Ser Ala Pro Gly Tyr Glu Thr
            730                 735                 740 ctg gca gaa acg ccg tgt ccc cca gcg ctg cag cca cag cca gct gaa    2492
Leu Ala Glu Thr Pro Cys Pro Pro Ala Leu Gln Pro Gln Pro Ala Glu
        745                 750                 755 gac ctg gta cct agt ggt cct gag gac tgt ggc ttc ttc ccc aat ggg    2540
Asp Leu Val Pro Ser Gly Pro Glu Asp Cys Gly Phe Phe Pro Asn Gly
    760                 765                 770 gcc ttt gac cac tgt ctg agt cac atc ccg tcc atc tac act gac acc    2588
Ala Phe Asp His Cys Leu Ser His Ile Pro Ser Ile Tyr Thr Asp Thr
775                 780                 785 tga aggaaggggc gctgctctgc ctgcctgcct ggctcctgag ctacttcacc         2641
tacctgccat ctgctggtgc ttcccacacg gggcagcaag ccacaccac agggtacttc   2701 cctacctgga gggctgtctg gtccagagct gcctgccagg agctatggcc ctctgacagc  2761
cccatggctg tgtcttcctc tctctccata aggttctcaa atcacagacc tcgtgtatat  2821
```

-continued

```
acaatgtaca ggacctcttt tccgccgccc tgcaagtttt atattttttgg ttttacaaga    2881 aaaacattaa aaactggaaa cta                                             2904
```

<210> SEQ ID NO 4
<211> LENGTH: 789
<212> TYPE: PRT
<213> ORGANISM: Mus musculus

<400> SEQUENCE: 4

```
Met His Cys Glu Val Ala Glu Ala Leu Ser Asp Lys Arg Pro Lys Glu
1               5                   10                  15

Ala Pro Gly Ala Pro Gly Gln Gly Arg Gly Pro Val Ser Leu Gly Ala
            20                  25                  30

His Met Ala Phe Arg Ile Ala Val Ser Gly Gly Cys Gly Asp Gly
        35                  40                  45

Asn Pro Leu Asp Leu Pro Arg Leu Pro Val Pro Pro Arg Ala
    50                  55                  60

His Asp Leu Leu Arg Pro Arg Ser Pro Arg Asp Tyr Gly Val Ser Lys
65                  70                  75                  80

Thr Gly Ser Gly Lys Val Asn Gly Ser Tyr Gly His Ser Ser Glu Lys
                85                  90                  95

Ser Leu Leu Asp Leu Asp Leu Ala Glu Gly Pro Ser Pro Ser Cys His
            100                 105                 110

Gln Gly Leu Phe Leu Pro Ala Gly Thr Pro Pro Arg Gly His Pro
        115                 120                 125

Pro Val Cys Glu Lys Leu Leu His Phe Pro His Pro Asn Arg Ser Pro
    130                 135                 140

Arg Pro Gln Ala Thr Phe Val Asn Gly Ser Leu Pro Ala Ala Gln His
145                 150                 155                 160

Ile Lys Gln Glu Ala Leu Pro Asp Tyr Gln Ala Met Val Ser Ala His
                165                 170                 175

Thr Pro Leu Pro Thr His Cys Arg Ala Pro Ser Ser Met Gly Leu Pro
            180                 185                 190

Ser Asp Leu Asp Phe Pro Asp Arg Gly Leu Thr Asn Pro Ala Pro Ser
        195                 200                 205

Cys Tyr Leu Leu Gly Asn Glu Pro Ile Ser Asp Leu Gly Pro Gln Pro
    210                 215                 220

Glu Ala His Leu Pro Glu Gly Ser Leu Lys Arg Cys Cys Leu Leu Gly
225                 230                 235                 240

Leu Pro Pro Thr Ser Ser Ala Ser Ser Ser Pro Cys Ala Ser Ser Asp
                245                 250                 255

Ile Asn Pro Val Ile His Ser Ser Gln Thr Ala Leu Val Ser Cys Val
            260                 265                 270

Asn Gly Leu Arg Ser Pro Pro Leu Pro Gly Asp Leu Gly Gly Pro Pro
        275                 280                 285

Lys Arg Ser Arg Pro Gly Pro Ala Ser Ser Asp Gln Glu Gly Ser
    290                 295                 300

Leu Gln Leu Glu Ala Cys Arg Lys Ser Gly Phe Leu Lys Gln Glu Pro
305                 310                 315                 320

Met Asp Glu Phe Ser Glu Leu Phe Ala Pro His Gln Gly Leu Pro
                325                 330                 335

Pro Pro Tyr Pro Leu Pro Gln Leu Pro Thr Gly Pro Gly Leu Gly Gly
            340                 345                 350

Leu Gly Leu Gly Leu Ala Gly Arg Met Val Ala Gly Arg Gln Ala Cys
```

-continued

```
            355                 360                 365
Arg Trp Val Asp Cys Cys Ala Ala Tyr Glu Gln Gln Glu Glu Leu Val
370                 375                 380
Arg His Ile Glu Lys Ser His Ile Asp Gln Arg Lys Gly Glu Asp Phe
385                 390                 395                 400
Thr Cys Phe Trp Ala Gly Cys Val Arg Arg Tyr Lys Pro Phe Asn Ala
                    405                 410                 415
Arg Tyr Lys Leu Leu Ile His Met Arg Val His Ser Gly Glu Lys Pro
            420                 425                 430
Asn Lys Cys Met Phe Glu Gly Cys Ser Lys Ala Phe Ser Arg Leu Glu
            435                 440                 445
Asn Leu Lys Ile His Leu Arg Ser His Thr Gly Glu Lys Pro Tyr Leu
450                 455                 460
Cys Gln His Pro Gly Cys Gln Lys Ala Phe Ser Asn Ser Ser Asp Arg
465                 470                 475                 480
Ala Lys His Gln Arg Thr His Leu Asp Thr Lys Pro Tyr Ala Cys Gln
                    485                 490                 495
Ile Pro Gly Cys Ser Lys Arg Tyr Thr Asp Pro Ser Ser Leu Arg Lys
            500                 505                 510
His Val Lys Ala His Ser Ala Lys Glu Gln Gln Val Arg Lys Lys Leu
            515                 520                 525
His Thr Gly Ala Asp Pro Glu Ala Asp Val Leu Ser Glu Cys Leu Ser
530                 535                 540
Leu Gln Gln Leu Gln Ala Ser Thr Leu Leu Pro Ala Ser Arg Gly Lys
545                 550                 555                 560
Gly Ser Gln Thr Leu Ser Gln Glu Leu Leu Pro Gly Val Tyr Pro Gly
                    565                 570                 575
Ser Val Thr Pro Gln Asn Gly Leu Ala Ser Gly Ile Leu Ser Pro Ser
            580                 585                 590
His Asp Val Pro Ser Arg His His Pro Leu Glu Val Pro Thr Gly Ser
            595                 600                 605
His His His Leu Ser Pro Leu Pro Thr Ala Glu Ser Thr Arg Asp Gly
610                 615                 620
Leu Gly Pro Ser Leu Leu Ser Pro Met Val Ser Pro Leu Lys Gly Leu
625                 630                 635                 640
Gly Pro Pro Pro Leu Pro Ala Ser Gln Ser Gln Ser Pro Gly Gly
                    645                 650                 655
Gln Ser Phe Ser Thr Val Pro Ser Lys Pro Thr Tyr Pro Ser Phe Gln
                    660                 665                 670
Ser Pro Pro Pro Leu Pro Ser Pro Gln Gly Tyr Gln Gly Ser Phe His
            675                 680                 685
Ser Ile Gln Asn Cys Phe Pro Tyr Ala Asp Cys Tyr Arg Ala Thr Glu
            690                 695                 700
Pro Ala Ala Ser Arg Asp Gly Leu Val Gly Asp Ala His Gly Phe Asn
705                 710                 715                 720
Pro Leu Arg Pro Ser Thr Tyr Ser Ser Leu Ser Thr Pro Leu Ser Ala
                    725                 730                 735
Pro Gly Tyr Glu Thr Leu Ala Glu Thr Pro Cys Pro Pro Ala Leu Gln
                    740                 745                 750
Pro Gln Pro Ala Glu Asp Leu Val Pro Ser Gly Pro Glu Asp Cys Gly
            755                 760                 765
Phe Phe Pro Asn Gly Ala Phe Asp His Cys Leu Ser His Ile Pro Ser
770                 775                 780
```

Ile Tyr Thr Asp Thr
785

<210> SEQ ID NO 5
<211> LENGTH: 2949
<212> TYPE: DNA
<213> ORGANISM: Homo sapiens
<220> FEATURE:
<221> NAME/KEY: CDS
<222> LOCATION: (595)..(2034)

<400> SEQUENCE: 5

| | |
|---|---|
| agtttcccga ccagagagaa cgaacgtgtc tgcgggcgcg cggggagcag aggcggtggc | 60 |
| gggcggcggc ggcaccggga ccgccgagt gaccctcccc cgcccctctg gcccccacc | 120 |
| ctcccacccg cccgtggccc gcgcccatgg ccgcgcgcgc tccacacaac tcaccggagt | 180 |
| ccgcgccttg cgccgccgac cagttcgcag ctccgcgcca cggcagccag tctcacctgg | 240 |
| cggcaccgcc cgcccaccgc ccggccaca gccctgcgc ccacggcagc actcgaggcg | 300 |
| accgcgacag tggtggggga cgctgctgag tggaagagag cgcagccgg ccaccggacc | 360 |
| tacttactcg ccttgctgat tgtctatttt tgcgtttaca acttttctaa gaacttttgt | 420 |
| atacaaagga acttttaaa aaagacgctt ccaagttata tttaatccaa agaagaagga | 480 |
| tctcggccaa tttggggttt tgggttttgg cttcgtttct tctcttcgtt gactttgggg | 540 |
| ttcaggtgcc ccagctgctt cgggctgccg aggaccttct gggcccccac atta atg | 597 |
|                                                          Met<br>                                                         1 |
| agg cag cca cct ggc gag tct gac atg gct gtc agc gac gcg ctg ctc<br>Arg Gln Pro Pro Gly Glu Ser Asp Met Ala Val Ser Asp Ala Leu Leu<br>     5           10           15 | 645 |
| cca tct ttc tcc acg ttc gcg tct ggc ccg gcg gga agg gag aag aca<br>Pro Ser Phe Ser Thr Phe Ala Ser Gly Pro Ala Gly Arg Glu Lys Thr<br>  20          25           30 | 693 |
| ctg cgt caa gca ggt gcc ccg aat aac cgc tgg cgg gag gag ctc tcc<br>Leu Arg Gln Ala Gly Ala Pro Asn Asn Arg Trp Arg Glu Glu Leu Ser<br>35           40           45 | 741 |
| cac atg aag cga ctt ccc cca gtg ctt ccc ggc cgc ccc tat gac ctg<br>His Met Lys Arg Leu Pro Pro Val Leu Pro Gly Arg Pro Tyr Asp Leu<br>50           55          60          65 | 789 |
| gcg gcg gcg acc gtg gcc aca gac ctg gag agc ggc gga gcc ggt gcg<br>Ala Ala Ala Thr Val Ala Thr Asp Leu Glu Ser Gly Gly Ala Gly Ala<br>          70            75           80 | 837 |
| gct tgc ggc ggt agc aac ctg gcg ccc cta cct cgg aga gag acc gag<br>Ala Cys Gly Gly Ser Asn Leu Ala Pro Leu Pro Arg Arg Glu Thr Glu<br>       85           90          95 | 885 |
| gag ttc aac gat ctc ctg gac ctg gac ttt att ctc tcc aat tcg ctg<br>Glu Phe Asn Asp Leu Leu Asp Leu Asp Phe Ile Leu Ser Asn Ser Leu<br>100           105          110 | 933 |
| acc cat cct ccg gag tca gtg gcc gcc acc gtg tcc tcg tca gcg tca<br>Thr His Pro Pro Glu Ser Val Ala Ala Thr Val Ser Ser Ser Ala Ser<br>  115          120          125 | 981 |
| gcc tcc tct tcg tcg tcg ccg tcg agc agc ggc cct gcc agc gcg ccc<br>Ala Ser Ser Ser Ser Pro Ser Ser Gly Pro Ala Ser Ala Pro<br>130          135          140          145 | 1029 |
| tcc acc tgc agc ttc acc tat ccg atc cgg gcc ggg aac gac ccg ggc<br>Ser Thr Cys Ser Phe Thr Tyr Pro Ile Arg Ala Gly Asn Asp Pro Gly<br>          150           155          160 | 1077 |
| gtg gcg ccg ggc ggc acg ggc gga ggc ctc ctc tat ggc agg gag tcc<br>Val Ala Pro Gly Gly Thr Gly Gly Gly Leu Leu Tyr Gly Arg Glu Ser | 1125 |

```
                    165                 170                 175
gct ccc cct ccg acg gct ccc ttc aac ctg gcg gac atc aac gac gtg    1173
Ala Pro Pro Thr Ala Pro Phe Asn Leu Ala Asp Ile Asn Asp Val
            180                 185                 190 agc ccc tcg ggc ggc ttc gtg gcc gag ctc ctg cgg cca gaa ttg gac    1221
Ser Pro Ser Gly Gly Phe Val Ala Glu Leu Leu Arg Pro Glu Leu Asp
    195                 200                 205 ccg gtg tac att ccg ccg cag cag ccg cag ccg cca ggt ggc ggg ctg    1269
Pro Val Tyr Ile Pro Pro Gln Gln Pro Gln Pro Pro Gly Gly Gly Leu
210                 215                 220                 225 atg ggc aag ttc gtg ctg aag gcg tcg ctg agc gcc cct ggc agc gag    1317
Met Gly Lys Phe Val Leu Lys Ala Ser Leu Ser Ala Pro Gly Ser Glu
                230                 235                 240 tac ggc agc ccg tcg gtc atc agc gtc agc aaa ggc agc cct gac ggc    1365
Tyr Gly Ser Pro Ser Val Ile Ser Val Ser Lys Gly Ser Pro Asp Gly
            245                 250                 255 agc cac ccg gtg gtg gtg gcg ccc tac aac ggc ggg ccg ccg cgc acg    1413
Ser His Pro Val Val Val Ala Pro Tyr Asn Gly Gly Pro Pro Arg Thr
    260                 265                 270 tgc ccc aag atc aag cag gag gcg gtc tct tcg tgc acc cac ttg ggc    1461
Cys Pro Lys Ile Lys Gln Glu Ala Val Ser Ser Cys Thr His Leu Gly
275                 280                 285 gct gga ccc cct ctc agc aat ggc cac cgg ccg gct gca cac gac ttc    1509
Ala Gly Pro Pro Leu Ser Asn Gly His Arg Pro Ala Ala His Asp Phe
290                 295                 300                 305 ccc ctg ggg cgg cag ctc ccc agc agg act acc ccg acc ctg ggt ctt    1557
Pro Leu Gly Arg Gln Leu Pro Ser Arg Thr Thr Pro Thr Leu Gly Leu
                310                 315                 320 gag gaa gtg ctg agc agc agg gac tgt cac cct gcc ctg ccg ctt cct    1605
Glu Glu Val Leu Ser Ser Arg Asp Cys His Pro Ala Leu Pro Leu Pro
            325                 330                 335 ccc ggc ttc cat ccc cac ccg ggg ccc aat tac cca tcc ttc ctg ccc    1653
Pro Gly Phe His Pro His Pro Gly Pro Asn Tyr Pro Ser Phe Leu Pro
    340                 345                 350 gat cag atg cag ccg caa gtc ccg ccg ctc cat tac caa gag ctc atg    1701
Asp Gln Met Gln Pro Gln Val Pro Pro Leu His Tyr Gln Glu Leu Met
355                 360                 365 cca ccc ggt tcc tgc atg cca gag gag ccc aag cca aag agg gga aga    1749
Pro Pro Gly Ser Cys Met Pro Glu Glu Pro Lys Pro Lys Arg Gly Arg
370                 375                 380                 385 cga tcg tgg ccc cgg aaa agg acc gcc acc cac act tgt gat tac gcg    1797
Arg Ser Trp Pro Arg Lys Arg Thr Ala Thr His Thr Cys Asp Tyr Ala
                390                 395                 400 ggc tgc ggc aaa acc tac aca aag agt tcc cat ctc aag gca cac ctg    1845
Gly Cys Gly Lys Thr Tyr Thr Lys Ser Ser His Leu Lys Ala His Leu
            405                 410                 415 cga acc cac aca ggt gag aaa cct tac cac tgt gac tgg gac ggc tgt    1893
Arg Thr His Thr Gly Glu Lys Pro Tyr His Cys Asp Trp Asp Gly Cys
    420                 425                 430 gga tgg aaa ttc gcc cgc tca gat gaa ctg acc agg cac tac cgt aaa    1941
Gly Trp Lys Phe Ala Arg Ser Asp Glu Leu Thr Arg His Tyr Arg Lys
435                 440                 445 cac acg ggg cac cgc ccg ttc cag tgc caa aaa tgc gac cga gca ttt    1989
His Thr Gly His Arg Pro Phe Gln Cys Gln Lys Cys Asp Arg Ala Phe
450                 455                 460                 465 tcc agg tcg gac cac ctc gcc tta cac atg aag agg cat ttt taa       2034
Ser Arg Ser Asp His Leu Ala Leu His Met Lys Arg His Phe
                470                 475 atcccagaca gtggatatga cccacactgc cagaagagaa ttcagtattt tttactttc  2094
```

| | |
|---|---|
| acactgtctt cccgatgagg aaggagccc agccagaaag cactacaatc atggtcaagt | 2154 |
| tcccaactga gtcatcttgt gagtggataa tcaggaaaaa tgaggaatcc aaaagacaaa | 2214 |
| aatcaaagaa cagatggggt ctgtgactgg atcttctatc attccaattc taaatccgac | 2274 |
| ttgaatattc ctggacttac aaaatgccaa gggggtgact ggaagttgtg atatcaggg | 2334 |
| tataaattat atccgtgagt tgggggaggg aagaccagaa ttcccttgaa ttgtgtattg | 2394 |
| atgcaatata agcataaaag atcaccttgt attctcttta ccttctaaaa gccattatta | 2454 |
| tgatgttaga agaagaggaa gaaattcagg tacagaaaac atgtttaaat agcctaaatg | 2514 |
| atggtgcttg gtgagtcttg gttctaaagg taccaaacaa ggaagccaaa gttttcaaac | 2574 |
| tgctgcatac tttgacaagg aaaatctata tttgtcttcc gatcaacatt tatgacctaa | 2634 |
| gtcaggtaat atacctggtt tacttcttta gcatttttat gcagacagtc tgttatgcac | 2694 |
| tgtggtttca gatgtgcaat aatttgtaca atggtttatt cccaagtatg ccttaagcag | 2754 |
| aacaaatgtg tttttctata tagttccttg ccttaataaa tatgtaatat aaatttaagc | 2814 |
| aaacgtctat tttgtatatt tgtaaactac aaagtaaaat gaacattttg tggagtttgt | 2874 |
| attttgcata ctcaaggtga gaattaagtt ttaaataaac ctataatatt ttatctgaaa | 2934 |
| aaaaaaaaaa aaaaa | 2949 |

<210> SEQ ID NO 6
<211> LENGTH: 479
<212> TYPE: PRT
<213> ORGANISM: Homo sapiens

<400> SEQUENCE: 6

Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
            20                  25                  30

Thr Leu Arg Gln Ala Gly Ala Pro Asn Asn Arg Trp Arg Glu Glu Leu
        35                  40                  45

Ser His Met Lys Arg Leu Pro Pro Val Leu Pro Gly Arg Pro Tyr Asp
    50                  55                  60

Leu Ala Ala Ala Thr Val Ala Thr Asp Leu Glu Ser Gly Gly Ala Gly
65                  70                  75                  80

Ala Ala Cys Gly Gly Ser Asn Leu Ala Pro Leu Pro Arg Arg Glu Thr
                85                  90                  95

Glu Glu Phe Asn Asp Leu Leu Asp Leu Asp Phe Ile Leu Ser Asn Ser
            100                 105                 110

Leu Thr His Pro Pro Glu Ser Val Ala Ala Thr Val Ser Ser Ser Ala
        115                 120                 125

Ser Ala Ser Ser Ser Ser Ser Pro Ser Ser Gly Pro Ala Ser Ala
    130                 135                 140

Pro Ser Thr Cys Ser Phe Thr Tyr Pro Ile Arg Ala Gly Asn Asp Pro
145                 150                 155                 160

Gly Val Ala Pro Gly Gly Thr Gly Gly Gly Leu Leu Tyr Gly Arg Glu
                165                 170                 175

Ser Ala Pro Pro Pro Thr Ala Pro Phe Asn Leu Ala Asp Ile Asn Asp
            180                 185                 190

Val Ser Pro Ser Gly Gly Phe Val Ala Glu Leu Leu Arg Pro Glu Leu
        195                 200                 205

Asp Pro Val Tyr Ile Pro Pro Gln Gln Pro Gln Pro Pro Gly Gly Gly

```
            210                 215                 220
Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
                245                 250                 255

Gly Ser His Pro Val Val Ala Pro Tyr Asn Gly Gly Pro Pro Arg
                260                 265                 270

Thr Cys Pro Lys Ile Lys Gln Glu Ala Val Ser Ser Cys Thr His Leu
            275                 280                 285

Gly Ala Gly Pro Pro Leu Ser Asn Gly His Arg Pro Ala Ala His Asp
        290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
                325                 330                 335

Pro Pro Gly Phe His Pro His Pro Gly Pro Asn Tyr Pro Ser Phe Leu
                340                 345                 350

Pro Asp Gln Met Gln Pro Gln Val Pro Pro Leu His Tyr Gln Glu Leu
            355                 360                 365

Met Pro Pro Gly Ser Cys Met Pro Glu Glu Pro Lys Pro Lys Arg Gly
        370                 375                 380

Arg Arg Ser Trp Pro Arg Lys Arg Thr Ala Thr His Thr Cys Asp Tyr
385                 390                 395                 400

Ala Gly Cys Gly Lys Thr Tyr Thr Lys Ser Ser His Leu Lys Ala His
                405                 410                 415

Leu Arg Thr His Thr Gly Glu Lys Pro Tyr His Cys Asp Trp Asp Gly
            420                 425                 430

Cys Gly Trp Lys Phe Ala Arg Ser Asp Glu Leu Thr Arg His Tyr Arg
        435                 440                 445

Lys His Thr Gly His Arg Pro Phe Gln Cys Gln Lys Cys Asp Arg Ala
    450                 455                 460

Phe Ser Arg Ser Asp His Leu Ala Leu His Met Lys Arg His Phe
465                 470                 475

<210> SEQ ID NO 7
<211> LENGTH: 3057
<212> TYPE: DNA
<213> ORGANISM: Mus musculus
<220> FEATURE:
<221> NAME/KEY: CDS
<222> LOCATION: (605)..(2056)

<400> SEQUENCE: 7
agttccccgg ccaagagagc gagcgcggct ccgggcgcgc ggggagcaga ggcggtggcg      60
ggcggcggcg gcacccggag ccgccgagtg cccctccccg ccctccagc ccccacccca     120 gcaacccgcc cgtgacccgc gcccatggcc gcgcgcaccc ggcacagtcc ccaggactcc     180
gcaccccgcg ccaccgccca gctcgcagtt ccgcgccacc gcggccattc tcacctggcg     240
gcgccgcccg cccaccgccc ggaccacagc ccccgcgccg ccgacagcca cagtggccgc     300
gacaacggtg ggggacactg ctgagtccaa gagcgtgcag cctggccatc ggacctactt     360
atctgccttg ctgattgtct atttttataa gagtttacaa cttttctaag aattttttgta    420 tacaaaggaa ctttttttaaa gacatcgccg gtttatattg aatccaaaga agaaggatct    480
cgggcaatct gggggttttg gtttgaggtt ttgtttctaa agtttttaat cttcgttgac     540
```

```
tttggggctc aggtacccct ctctcttctt cggactccgg aggaccttct gggcccccac        600 atta atg agg cag cca cct ggc gag tct gac atg gct gtc agc gac gct        649
     Met Arg Gln Pro Pro Gly Glu Ser Asp Met Ala Val Ser Asp Ala
     1               5                   10                  15 ctg ctc ccg tcc ttc tcc acg ttc gcg tcc ggc ccg gcg gga agg gag        697
Leu Leu Pro Ser Phe Ser Thr Phe Ala Ser Gly Pro Ala Gly Arg Glu
                20                  25                  30 aag aca ctg cgt cca gca ggt gcc ccg act aac cgt tgg cgt gag gaa        745
Lys Thr Leu Arg Pro Ala Gly Ala Pro Thr Asn Arg Trp Arg Glu Glu
            35                  40                  45 ctc tct cac atg aag cga ctt ccc cca ctt ccc ggc cgc ccc tac gac        793
Leu Ser His Met Lys Arg Leu Pro Pro Leu Pro Gly Arg Pro Tyr Asp
        50                  55                  60 ctg gcg gcg acg gtg gcc aca gac ctg gag agt ggc gga gct ggt gca        841
Leu Ala Ala Thr Val Ala Thr Asp Leu Glu Ser Gly Gly Ala Gly Ala
    65                  70                  75 gct tgc agc agt aac aac ccg gcc ctc cta gcc cgg agg gag acc gag        889
Ala Cys Ser Ser Asn Asn Pro Ala Leu Leu Ala Arg Arg Glu Thr Glu
80                  85                  90                  95 gag ttc aac gac ctc ctg gac cta gac ttt atc ctt tcc aac tcg cta        937
Glu Phe Asn Asp Leu Leu Asp Leu Asp Phe Ile Leu Ser Asn Ser Leu
                100                 105                 110 acc cac cag gaa tcg gtg gcc gcc acc gtg acc acc tcg gcg tca gct        985
Thr His Gln Glu Ser Val Ala Ala Thr Val Thr Thr Ser Ala Ser Ala
            115                 120                 125 tca tcc tcg tct tcc ccg gcg agc agc ggc cct gcc agc gcg ccc tcc       1033
Ser Ser Ser Ser Ser Pro Ala Ser Ser Gly Pro Ala Ser Ala Pro Ser
        130                 135                 140 acc tgc agc ttc agc tat ccg atc cgg gcc ggg ggt gac ccg ggc gtg       1081
Thr Cys Ser Phe Ser Tyr Pro Ile Arg Ala Gly Gly Asp Pro Gly Val
    145                 150                 155 gct gcc agc aac aca ggt gga ggg ctc ctc tac agc cga gaa tct gcg       1129
Ala Ala Ser Asn Thr Gly Gly Gly Leu Leu Tyr Ser Arg Glu Ser Ala
160                 165                 170                 175 cca cct ccc acg gcc ccc ttc aac ctg gcg gac atc aat gac gtg agc       1177
Pro Pro Pro Thr Ala Pro Phe Asn Leu Ala Asp Ile Asn Asp Val Ser
                180                 185                 190 ccc tcg ggc ggc ttc gtg gct gag ctc ctg cgg ccg gag ttg gac cca       1225
Pro Ser Gly Gly Phe Val Ala Glu Leu Leu Arg Pro Glu Leu Asp Pro
            195                 200                 205 gta tac att ccg cca cag cag cct cag ccg cca ggt ggc ggg ctg atg       1273
Val Tyr Ile Pro Pro Gln Gln Pro Gln Pro Pro Gly Gly Gly Leu Met
        210                 215                 220 ggc aag ttt gtg ctg aag gcg tct ctg acc acc cct ggc agc gag tac       1321
Gly Lys Phe Val Leu Lys Ala Ser Leu Thr Thr Pro Gly Ser Glu Tyr
    225                 230                 235 agc agc cct tcg gtc atc agt gtt agc aaa gga agc cca gac ggc agc       1369
Ser Ser Pro Ser Val Ile Ser Val Ser Lys Gly Ser Pro Asp Gly Ser
240                 245                 250                 255 cac ccc gtg gta gtg gcg ccc tac agc ggt ggc ccg ccg cgc atg tgc       1417
His Pro Val Val Val Ala Pro Tyr Ser Gly Gly Pro Pro Arg Met Cys
                260                 265                 270 ccc aag att aag caa gag gcg gtc ccg tcc tgc acg gtc agc cgg tcc       1465
Pro Lys Ile Lys Gln Glu Ala Val Pro Ser Cys Thr Val Ser Arg Ser
            275                 280                 285 cta gag gcc cat ttg agc gct gga ccc cag ctc agc aac ggc cac cgg       1513
Leu Glu Ala His Leu Ser Ala Gly Pro Gln Leu Ser Asn Gly His Arg
        290                 295                 300 ccc aac aca cac gac ttc ccc ctg ggg cgg cag ctc ccc acc agg act       1561
```

```
Pro Asn Thr His Asp Phe Pro Leu Gly Arg Gln Leu Pro Thr Arg Thr
    305                 310                 315 acc cct aca ctg agt ccc gag gaa ctg ctg aac agc agg gac tgt cac      1609
Thr Pro Thr Leu Ser Pro Glu Glu Leu Leu Asn Ser Arg Asp Cys His
320                 325                 330                 335 cct ggc ctg cct ctt ccc cca gga ttc cat ccc cat ccg ggg ccc aac      1657
Pro Gly Leu Pro Leu Pro Pro Gly Phe His Pro His Pro Gly Pro Asn
                340                 345                 350 tac cct cct ttc ctg cca gac cag atg cag tca caa gtc ccc tct ctc      1705
Tyr Pro Pro Phe Leu Pro Asp Gln Met Gln Ser Gln Val Pro Ser Leu
            355                 360                 365 cat tat caa gag ctc atg cca ccg ggt tcc tgc ctg cca gag gag ccc      1753
His Tyr Gln Glu Leu Met Pro Pro Gly Ser Cys Leu Pro Glu Glu Pro
        370                 375                 380 aag cca aag agg gga aga agg tcg tgg ccc cgg aaa aga aca gcc acc      1801
Lys Pro Lys Arg Gly Arg Arg Ser Trp Pro Arg Lys Arg Thr Ala Thr
    385                 390                 395 cac act tgt gac tat gca ggc tgt ggc aaa acc tat acc aag agt tct      1849
His Thr Cys Asp Tyr Ala Gly Cys Gly Lys Thr Tyr Thr Lys Ser Ser
400                 405                 410                 415 cat ctc aag gca cac ctg cga act cac aca ggc gag aaa cct tac cac      1897
His Leu Lys Ala His Leu Arg Thr His Thr Gly Glu Lys Pro Tyr His
                420                 425                 430 tgt gac tgg gac ggc tgt ggg tgg aaa ttc gcc cgc tcc gat gaa ctg      1945
Cys Asp Trp Asp Gly Cys Gly Trp Lys Phe Ala Arg Ser Asp Glu Leu
            435                 440                 445 acc agg cac tac cgc aaa cac aca ggg cac cgg ccc ttt cag tgc cag      1993
Thr Arg His Tyr Arg Lys His Thr Gly His Arg Pro Phe Gln Cys Gln
        450                 455                 460 aag tgt gac agg gcc ttt tcc agg tcg gac cac ctt gcc tta cac atg      2041
Lys Cys Asp Arg Ala Phe Ser Arg Ser Asp His Leu Ala Leu His Met
    465                 470                 475 aag agg cac ttt taa atcccacgta gtggatgtga cccacactgc caggagagag      2096
Lys Arg His Phe
480 agttcagtat tttttttct aacctttcac actgtcttcc cacgagggga ggagcccagc    2156 tggcaagcgc tacaatcatg gtcaagttcc cagcaagtca gcttgtgaat ggataatcag    2216 gagaaaggaa gagttcaaga gacaaaacag aaatactaaa aacaaacaaa caaaaaaaca    2276 aacaaaaaaa acaagaaaaa aaaatcacag aacagatggg gtctgatact ggatggatct    2336 tctatcattc caataccaaa tccaacttga acatgcccgg acttacaaaa tgccaagggg    2396 tgactggaag tttgtggata tcagggtata cactaaatca gtgagcttgg ggggagggaa    2456 gaccaggatt cccttgaatt gtgtttcgat gatgcaatac acacgtaaag atcaccttgt    2516 atgctctttg ccttcttaaa aaaaaaaaaa gccattattg tgtcggagga agaggaagcg    2576 attcaggtac agaacatgtt ctaacagcct aaatgatggt gcttggtgag tcgtggttct    2636 aaaggtacca aacggggggag ccaaagttct ccaactgctg catactttg acaaggaaaa    2696 tctagttttg tcttccgatc tacattgatg acctaagcca ggtaaataag cctggtttat    2756 ttctgtaaca ttttatgca gacagtctgt tatgcactgt ggtttcagat gtgcaataat    2816 ttgtacaatg gttattccc aagtatgcct ttaagcagaa caaatgtgtt tttctatata    2876 gttccttgcc ttaataaata tgtaatataa atttaagcaa acttctattt tgtatatttg    2936 taaactacaa agtaaaaaaa aatgaacatt ttgtggagtt tgtattttgc atactcaagg    2996 tgagaaataa gttttaaata aacctataat atttttatctg aacgacaaaa aaaaaaaaaa    3056
```

<210> SEQ ID NO 8
<211> LENGTH: 483
<212> TYPE: PRT
<213> ORGANISM: Mus musculus

<400> SEQUENCE: 8

```
Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
            20                  25                  30

Thr Leu Arg Pro Ala Gly Ala Pro Thr Asn Arg Trp Arg Glu Glu Leu
        35                  40                  45

Ser His Met Lys Arg Leu Pro Pro Leu Pro Gly Arg Pro Tyr Asp Leu
    50                  55                  60

Ala Ala Thr Val Ala Thr Asp Leu Glu Ser Gly Gly Ala Gly Ala Ala
65                  70                  75                  80

Cys Ser Ser Asn Asn Pro Ala Leu Leu Ala Arg Arg Glu Thr Glu Glu
                85                  90                  95

Phe Asn Asp Leu Leu Asp Leu Asp Phe Ile Leu Ser Asn Ser Leu Thr
            100                 105                 110

His Gln Glu Ser Val Ala Ala Thr Val Thr Thr Ser Ala Ser Ala Ser
        115                 120                 125

Ser Ser Ser Ser Pro Ala Ser Ser Gly Pro Ala Ser Ala Pro Ser Thr
    130                 135                 140

Cys Ser Phe Ser Tyr Pro Ile Arg Ala Gly Gly Asp Pro Gly Val Ala
145                 150                 155                 160

Ala Ser Asn Thr Gly Gly Gly Leu Leu Tyr Ser Arg Glu Ser Ala Pro
                165                 170                 175

Pro Pro Thr Ala Pro Phe Asn Leu Ala Asp Ile Asn Asp Val Ser Pro
            180                 185                 190

Ser Gly Gly Phe Val Ala Glu Leu Leu Arg Pro Glu Leu Asp Pro Val
        195                 200                 205

Tyr Ile Pro Pro Gln Gln Pro Gln Pro Gly Gly Gly Leu Met Gly
    210                 215                 220

Lys Phe Val Leu Lys Ala Ser Leu Thr Thr Pro Gly Ser Glu Tyr Ser
225                 230                 235                 240

Ser Pro Ser Val Ile Ser Val Ser Lys Gly Ser Pro Asp Gly Ser His
                245                 250                 255

Pro Val Val Val Ala Pro Tyr Ser Gly Pro Pro Arg Met Cys Pro
            260                 265                 270

Lys Ile Lys Gln Glu Ala Val Pro Ser Cys Thr Val Ser Arg Ser Leu
        275                 280                 285

Glu Ala His Leu Ser Ala Gly Pro Gln Leu Ser Asn Gly His Arg Pro
    290                 295                 300

Asn Thr His Asp Phe Pro Leu Gly Arg Gln Leu Pro Thr Arg Thr Thr
305                 310                 315                 320

Pro Thr Leu Ser Pro Glu Glu Leu Leu Asn Ser Arg Asp Cys His Pro
                325                 330                 335

Gly Leu Pro Leu Pro Gly Phe His Pro His Pro Gly Pro Asn Tyr
            340                 345                 350

Pro Pro Phe Leu Pro Asp Gln Met Gln Ser Gln Val Pro Ser Leu His
        355                 360                 365
```

-continued

Tyr Gln Glu Leu Met Pro Pro Gly Ser Cys Leu Pro Glu Glu Pro Lys
370             375                 380

Pro Lys Arg Gly Arg Arg Ser Trp Pro Arg Lys Arg Thr Ala Thr His
385                 390                 395                 400

Thr Cys Asp Tyr Ala Gly Cys Gly Lys Thr Tyr Thr Lys Ser Ser His
                405                 410                 415

Leu Lys Ala His Leu Arg Thr His Thr Gly Glu Lys Pro Tyr His Cys
            420                 425                 430

Asp Trp Asp Gly Cys Gly Trp Lys Phe Ala Arg Ser Asp Glu Leu Thr
        435                 440                 445

Arg His Tyr Arg Lys His Thr Gly His Arg Pro Phe Gln Cys Gln Lys
450                 455                 460

Cys Asp Arg Ala Phe Ser Arg Ser Asp His Leu Ala Leu His Met Lys
465                 470                 475                 480

Arg His Phe

<210> SEQ ID NO 9
<211> LENGTH: 81
<212> TYPE: DNA
<213> ORGANISM: Foot-and-mouth disease virus

<400> SEQUENCE: 9
aaaattgtcg ctcctgtcaa acaaactctt aactttgatt tactcaaact ggctggggat    60
gtagaaagca atccaggtcc a                                              81

<210> SEQ ID NO 10
<211> LENGTH: 34
<212> TYPE: DNA
<213> ORGANISM: Bacteriophage P1

<400> SEQUENCE: 10
ataacttcgt atagcataca ttatacgaag ttat                                34

<210> SEQ ID NO 11
<211> LENGTH: 34
<212> TYPE: DNA
<213> ORGANISM: Artificial Sequence
<220> FEATURE:
<223> OTHER INFORMATION: Synthetic mutant loxP (lox71) sequence

<400> SEQUENCE: 11
taccgttcgt atagcataca ttatacgaag ttat                                34

<210> SEQ ID NO 12
<211> LENGTH: 34
<212> TYPE: DNA
<213> ORGANISM: Artificial Sequence
<220> FEATURE:
<223> OTHER INFORMATION: Synthetic mutant loxP (lox66) sequence

<400> SEQUENCE: 12
ataacttcgt atagcataca ttatacgaac ggta                                34

<210> SEQ ID NO 13
<211> LENGTH: 21
<212> TYPE: DNA
<213> ORGANISM: Artificial Sequence
<220> FEATURE:
<223> OTHER INFORMATION: Synthetic shRNA

```
<400> SEQUENCE: 13
ggcctcacca accctgcacc t                                              21

<210> SEQ ID NO 14
<211> LENGTH: 21
<212> TYPE: DNA
<213> ORGANISM: Artificial Sequence
<220> FEATURE:
<223> OTHER INFORMATION: Synthetic shRNA

<400> SEQUENCE: 14
gcccttcaat gcccgctaca a                                              21

<210> SEQ ID NO 15
<211> LENGTH: 21
<212> TYPE: DNA
<213> ORGANISM: Artificial Sequence
<220> FEATURE:
<223> OTHER INFORMATION: Synthetic shRNA

<400> SEQUENCE: 15
gggcaatgaa cccatctcag a                                              21
```